United States Patent

Hirai et al.

[11] Patent Number: 5,883,049
[45] Date of Patent: Mar. 16, 1999

[54] HYDANTOIN DERIVATIVES AND HERBICIDES CONTAINING SAID DERIVATIVES AS ACTIVE INGREDIENT

[75] Inventors: Kenji Hirai; Tomoyuki Yano; Natsuko Okano, all of Kanagawa-ken; Sadayuki Ugai; Osamu Yamada, both of Shizuoka-ken, all of Japan

[73] Assignees: Sagami Chemical Research Center, Kanagawa; Kaken Pharmaceutical Co., Ltd., Tokyo, both of Japan

[21] Appl. No.: 836,154

[22] PCT Filed: Dec. 26, 1995

[86] PCT No.: PCT/JP95/02683

§ 371 Date: Aug. 18, 1997

§ 102(e) Date: Aug. 18, 1997

[87] PCT Pub. No.: WO96/20195

PCT Pub. Date: Jul. 4, 1996

[30] Foreign Application Priority Data

Dec. 27, 1994 [JP] Japan .................................. 6-3245536
May 22, 1995 [JP] Japan .................................. 7-122054

[51] Int. Cl.$^6$ .......................... A01N 43/90; C07D 471/04
[52] U.S. Cl. .......................... 504/246; 504/221; 504/225; 544/52; 544/105; 546/121
[58] Field of Search ................ 546/121; 504/246

[56] References Cited

U.S. PATENT DOCUMENTS

| | | | |
|---|---|---|---|
| 4,437,877 | 3/1984 | Nagano et al. | 71/90 |
| 5,362,706 | 11/1994 | Seckinger et al. | 504/221 |

FOREIGN PATENT DOCUMENTS

| | | |
|---|---|---|
| 0070389 | 1/1983 | European Pat. Off. |
| 0263299 | 4/1988 | European Pat. Off. |
| 0384973 | 9/1990 | European Pat. Off. |
| 0468930 | 1/1992 | European Pat. Off. |

OTHER PUBLICATIONS

Cram and Hammond, "Organic Chemistry" McGraw Hill Book Co., NY (1964) 2nd Editon, pp. 565–567, 1964.

*Primary Examiner*—Patricia L. Morris
*Attorney, Agent, or Firm*—Nixon & Vanderhye P.C.

[57] ABSTRACT

This invention provides with novel hydantoin derivatives, processes for preparing them, and herbicides containing said derivatives as active ingredient.

The hydantoin derivative of this invention represented by the general formula (1):

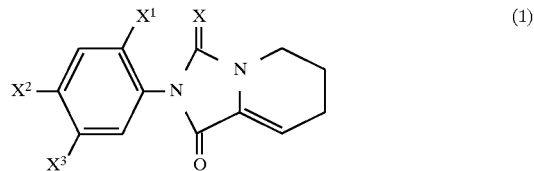

is produced by reacting an arylisocyanate derivative or an arylisothiocyanate derivative represented by the general formula (2):

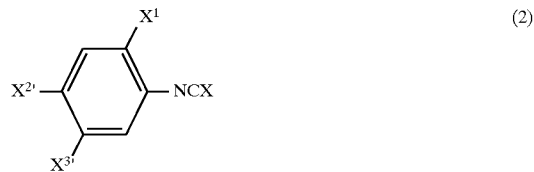

with a dehydropipecolic acid derivative represented by the general formula (3):

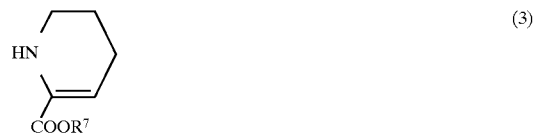

2 Claims, No Drawings

HYDANTOIN DERIVATIVES AND HERBICIDES CONTAINING SAID DERIVATIVES AS ACTIVE INGREDIENT

FIELD OF THE INVENTION

This invention relates to novel hydantoin derivatives, processes for preparing them, and herbicides containing said derivatives as active ingredient.

DESCRIPTION OF THE PRIOR ART

Although it has been known that hydantoin derivatives having a substituted aryl group on the 3-position nitrogen atom have a herbicidal activity (for example, EP-0070389-A, EP-0468930-A), nothing has been reported about the synthesis of derivatives having a double bond at the 5-position of a hydantoin ring as represented by the general formula (1) of this invention.

DISCLOSURE OF THE INVENTION

After profound studies to seek for an excellent herbicide, the inventors found processes for easily preparing hydantoin derivatives represented by the following general formula (1) of this invention which had not at all been known before and also found that these derivatives have an excellent herbicidal activity, thus finally accomplished this invention.

Accordingly, this invention relates to a hydantoin derivative represented by the general formula (1):

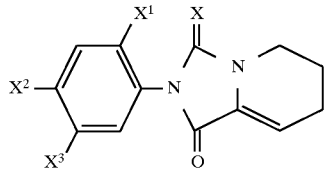

wherein X represents an oxygen atom or a sulfur atom, $X^1$ represents a hydrogen atom, a halogen atom or a C1–8 alkyl group, $X^2$ represents a hydrogen atom, a halogen atom, a C1–8 alkyl group or a group represented by the formula: $—Y—CH(R^1)C(=O)OR^2$, $X^3$ represents a hydrogen atom, a halogen atom, a C1–8 alkyl group, $ZR^3$, a nitro group or $NR^4R^5$, or $X^2$ and $X^3$ may be combined together to form a group represented by the formula: $—Y—CH(R^1)C(=O)NR^6—$, wherein Y and Z represent an oxygen atom or a sulfur atom, $R^1$ represents a hydrogen atom or a C1–4 alkyl group, $R^2$ represents a C1–6 alkyl group or an aralkyl group, $R^3$ represents a hydrogen atom, a C1–11 alkyl group, a C3–8 cycloalkyl group, a C3–12 alkenyl group, a C3–12 alkynyl group, a C1–8 alkoxycarbonylmethyl group, a C1–8 alkoxycarbonyl group or a C7–11 aralkyloxycarbonyl group, $R^4$ and $R^5$ independently represent a hydrogen atom, a C1–6 alkyl group, a C2–6 acyl group, a C1–6 alkylsulfonyl group or an arylsulfonyl group, $R^6$ represents a hydrogen atom, a C1–11 alkyl group, a C3–8 cycloalkyl group, a C3–12 alkenyl group or a C3–12 alkynyl group.

This invention also relates to a process for preparing a hydantoin derivative represented by the general formula (4):

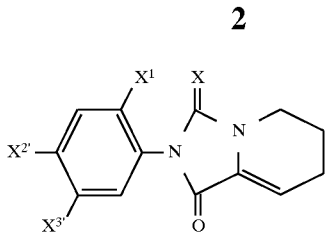

wherein X represents an oxygen atom or a sulfur atom, $X^1$ represents a hydrogen atom, a halogen atom or a C1–8 alkyl group, $X^{2'}$ represents a hydrogen atom, a halogen atom or a C1–8 alkyl group and $X^{3'}$ represents a hydrogen atom, a halogen atom, a C1–8 alkyl group, $ZR^{3'}$, a nitro group or $NR^{4'}R^{5'}$, wherein Y and Z represent an oxygen atom or a sulfur atom, $R^1$ represents a hydrogen atom or a C1–4 alkyl group, $R^{3'}$ represents a C1–11 alkyl group, a C3–8 cycloalkyl group, a C3–12 alkenyl group, a C3–12 alkynyl group, a C1–8 alkoxycarbonylmethyl group, a C1–8 alkoxycarbonyl group or a C7–11 aralkyloxycarbonyl group, $R^{4'}$ and $R^{5'}$ independently represent a C1–6 alkyl group, a C2–6 acyl group, a C1–6 alkylsulfonyl group or an arylsulfonyl group, and $R^6$ represents a hydrogen atom, a C1–11 alkyl group, a C3–8 cycloalkyl group, a C3–12 alkenyl group or a C3–12 alkynyl group, which comprises reacting an aryliso-cyanate derivative or an arylisothiocyanate derivative represented by the general formula (2):

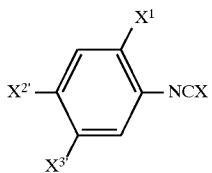

wherein X, $X^1$, $X^{2'}$ and $X^{3'}$ have the same meanings as defined above, with a dehydropipecolic acid derivative represented by the general formula (3):

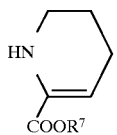

wherein $R^7$ represents a hydrogen atom or a C1–6 alkyl group.

This invention also relates to a process for preparing a hydantoin derivative represented by the general formula (6):

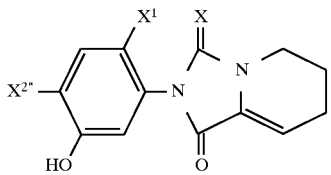

wherein X represents an oxygen atom or a sulfur atom, and $X^1$ and $X^{2''}$ independently represent a hydrogen atom, a halogen atom or a C1–8 alkyl group, which comprises hydrolyzing a hydantoin derivative represented by the general formula (5):

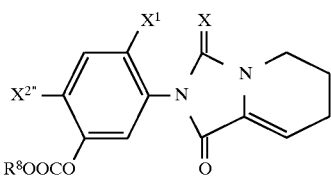

wherein X, $X^1$ and $X^{2''}$ have the same meanings as defined above, and R8 represents a C1–8 alkyl group or a C7–11 aralkyl group.

This invention also relates to a process for preparing a hydantoin derivative represented by the general formula (8):

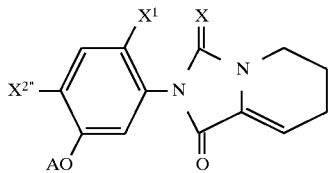

wherein X, $X^1$ and $X^{2''}$ have the same meanings as defined above, and A represents a C1–11 alkyl group, a C3–8 cyclo-alkyl group, a C3–12 alkenyl group, a C3–12 alkynyl group, a C1–8 alkoxycarbonylmethyl group, a C1–8 alkoxycarbonyl group or a C7–11 aralkyloxycarbonyl group, which comprises reacting a hydantoin derivative represented by the general formula (6):

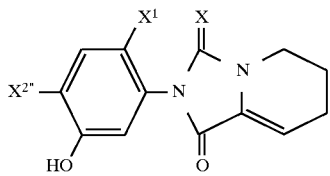

wherein X, $X^1$ and $X^{2''}$ have the same meanings as defined above, with a compound represented by the general formula (7):

A—L    (7)

wherein A has the same meaning as defined above and L represents a leaving group, in the presence of a base.

This invention also relates to a process for preparing a hydantoin derivative represented by the general formula (10):

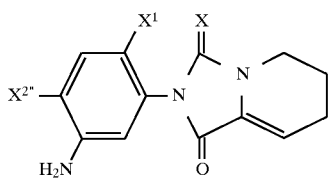

wherein X, $X^1$ and $X^{2''}$ have the same meanings as defined above, which comprises reducing a hydantoin derivative represented by the general formula (9):

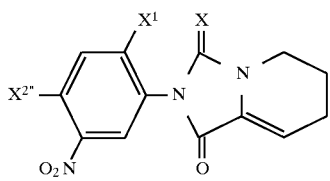

wherein X, $X^1$ and $X^{2''}$ have the same meanings as defined above.

This invention also relates to a process for preparing a hydantoin derivative represented by the general formula (12):

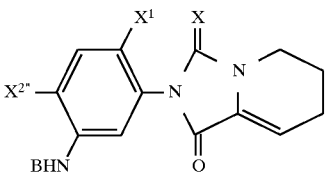

wherein X, $X^1$ and $X^{2''}$ have the same meanings as defined above, and B represents a C2–6 acyl group, a C1–6 alkylsufonyl group or an arylsulfonyl group, which comprises reacting a hydantoin derivative represented by the general formula (10):

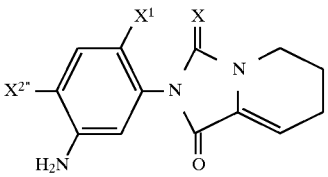

wherein X, $X^1$ and $X^{2''}$ have the same meanings as defined above, with a derivative represented by the general formula (11):

B—L    (11)

wherein B has the same meaning as defined above and L represents a leaving group, in the presence of a base.

This invention also relates to a process for preparing a bicyclic hydantoin derivative represented by the general formula (15):

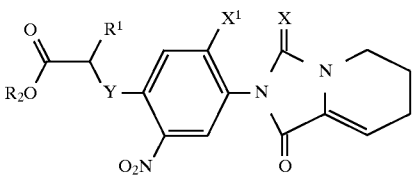

wherein X represents an oxygen atom or a sulfur atom, $X^1$ represents a hydrogen atom, a halogen atom or a C1–4 alkyl group, Y represents an oxygen atom or a sulfur atom, $R^1$ represents a hydrogen atom or a C1–4 alkyl group, and $R^2$ represents a C1–6 alkyl group or an aralkyl group, which comprises reacting a bicyclic hydantoin derivative represented by the general formula (13):

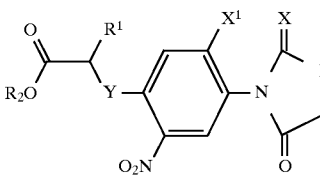

wherein X and $X^1$ have the same meanings as defined above and $X^4$ represents a halogen atom, with a glycolic acid derivative or a thioglycolic acid derivative represented by the general formula (14):

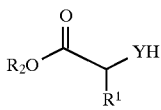

wherein $R^1$, $R^2$ and Y have the same meanings as defined above in the presence of a base.

This invention also relates to a process for preparing a bicyclic hydantoin derivative represented by the general formula (17):

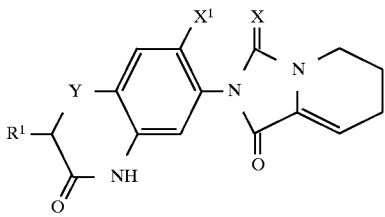

wherein X, $X^1$, Y and $R^1$ have the same meanings as defined above, which comprises reducing the nitro group of a bicyclic hydantoin derivative represented by the general formula (15):

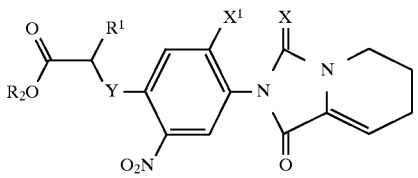

wherein X, $X^1$, Y, $R^1$ and $R^2$ have the same meanings as defined above, and intramolecularly amidating the thus obtained bicyclic hydantoin derivative represented by the general formula (16):

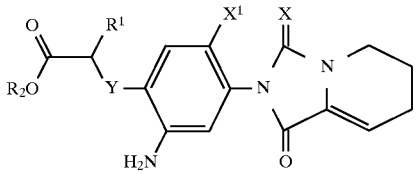

wherein X, $X^1$, Y, $R^1$ and $R^2$ have the same meanings as defined above.

This invention also relates to a process for preparing a bicyclic hydantoin derivative represented by the general formula (19):

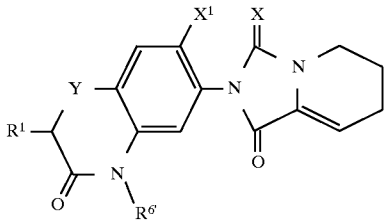

wherein X, $X^1$, Y and $R^1$ have the same meanings as defined above and $R^{6'}$ represents a C1–11 alkyl group, a C3–8 cycloalkyl group, C3–12 alkenyl group or a C3–12 alkynyl group, which comprises reacting a bicyclic hydantoin derivative represented by the general formula (17):

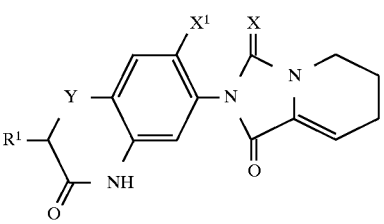

wherein X, $X^1$, Y and $R^1$ have the same meanings as defined above, with a derivative represented by the general formula (18):

$$R^{6'}—L \qquad (18)$$

wherein $R^{6'}$ has the same meaning as defined above and L represents a leaving group in the presence of a base.

This invention also relates to a process for preparing a dehydropipecolic acid derivative represented by the general formula (3):

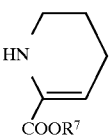

wherein $R^7$ has the same meaning as defined above, which comprises reacting a pipecolic acid derivative represented by the general formula (20):

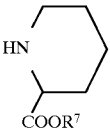

wherein $R^7$ has the same meaning as defined above, with an N-chlorinating agent, and then treating the reaction product with a base.

Finally, this invention relates to a herbicide containing as an active ingredient a hydantoin derivative represented by the general formula (1):

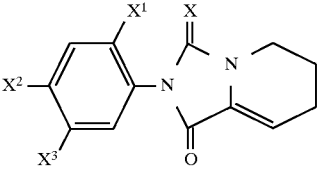

wherein X represents an oxygen atom or a sulfur atom, $X^1$ represents a hydrogen atom, a halogen atom or a C1–8 alkyl group, $X^2$ represents a hydrogen atom, a halogen atom, a C1–8 alkyl group or a group represented by the formula: —Y—CH($R^1$)C(=O)O$R^2$, $X^3$ represents a hydrogen atom, a halogen atom, a C1–8 alkyl group, $ZR^3$, a nitro group or $NR^4R^5$, or $X^2$ and $X^3$ may be combined together to form a group represented by the formula: —Y—CH($R^1$)C(=O)N$R^6$—, wherein Y and Z represent an oxygen atom or a sulfur atom, $R^1$ represents a hydrogen atom or a C1–4 alkyl group, $R^2$ represents a C1–6 alkyl group or an aralkyl group, $R^3$ represents a hydrogen atom, a C1–11 alkyl group, a C3–8 cycloalkyl group, a C3–12 alkenyl group, a C3–12 alkynyl group, a C1–8 alkoxycarbonylmethyl group, a C1–8 alkoxycarbonyl group or a C7–11 aralkyloxycarbonyl group, $R^4$ and $R^5$ independently represent a hydrogen atom, a C1–6 alkyl group, a C2–6 acyl group, a C1–6 alkylsulfonyl group or an arylsulfonyl group, $R^6$ represents a hydrogen atom, a C1–11 alkyl group, a C3–8 cycloalkyl group, a C3–12 alkenyl group or a C3–12 alkynyl group.

In the above formulae, the halogen atom represented by $X^1$, $X^2$, $X^{2'}$, $X^{2''}$, $X^3$, $X^{3'}$ and $X^4$ may include a fluorine atom, a chlorine atom, a bromine atom, etc.

The C1–8 alkyl group represented by $X^1$, $X^2$, $X^{2'}$, $X^{2''}$, $X^3$ and $X^{3'}$ may include methyl, ethyl, propyl, isopropyl, butyl, isobutyl, t-butyl, pentyl, hexyl, octyl and other groups. These alkyl groups may carry one or more substituents including a halogen atom or the like, as represented by trifluoromethyl and other groups.

The C1–4 alkyl group represented by $R^1$ may include methyl, ethyl, propyl, isopropyl, butyl, isobutyl and other groups.

The C1–6 alkyl group represented by $R^2$ may include methyl, ethyl, propyl, isopropyl, butyl, isobutyl, t-butyl, pentyl, hexyl and other groups. The aralkyl group may include benzyl, α-phenethyl, β-phenethyl, cumyl, naphthylmethyl and other groups. These aryl groups may carry a substituent including a C1–4 alkyl group as mentioned above, a C1–4 polyhaloalkyl group, a halogen atom, a C1–4 alkoxy group, a nitro group, a cyano group, etc. The C1–4 polyhaloalkyl group may include difluoro-methyl, trifluoromethyl, trifluoroethyl, 4-chlorobutyl and other groups, and the C1–4 alkoxy group may include methoxy, ethoxy, propoxy, butoxy, isobutoxy and other groups.

The C1–11 alkyl group represented by $R^3$, $R^{3'}$, $R^6$ and $R^{6'}$ may include methyl, ethyl, propyl, isopropyl, butyl, isobutyl, t-butyl, pentyl, hexyl, octyl, decyl and other groups. These alkyl groups may carry one or more substituents including a halogen atom, an aryl group, a C1–4 alkoxy group, a carboxy group, an acyl group or the like, as represented by difluoromethyl, 2,2,2-trifluoro-ethyl, 2-chloroethyl, 3-chloropropyl, benzyl, α-phenethyl, β-phenethyl, cumyl, naphthylmethyl, carboxymethyl, acetyl-methyl, 1-acetylethyl, 3-acetylpropyl, butanoylethyl and other groups.

The C3–8 cycloalkyl group represented by $R^3$, $R^{3'}$, $R^6$ and $R^{6'}$ may include cyclopropyl, cyclopentyl, cyclohexyl, cycloheptyl, cyclooctyl and other groups, which may be substituted by a C1–4 alkyl group.

The C3–12 alkenyl group represented by $R^3$, $R^{3'}$, $R^6$ and $R^{6'}$ may include methallyl, 2-propenyl, 2-butenyl, 3-butenyl, 2-pentenyl, 3-pentenyl, 2-hexenyl, 3-hexenyl, 5-octenyl, 8-decenyl and other groups.

The C3–12 alkynyl group represented by $R^3$, $R^{3'}$, $R^6$ and $R^{6'}$ may include propargyl, 1-methylpropargyl, 1,1-dimethylpropargyl, 2-butynyl, 3-butynyl, 2-pentynyl, 3-pentynyl, 3-octynyl, 5-decynyl and other groups.

The C1–8 alkoxycarbonylmethyl group represented by $R^3$, $R^{3'}$, $R^6$ and $R^{6'}$ may include methoxycarbonylmethyl, ethoxycarbonylmethyl, propoxycarbonylmethyl, isopropoxy-carbonylmethyl, butoxycarbonylmethyl, pentyloxycarbonyl-methyl, hexyloxycarbonylmethyl, octyloxycarbonylmethyl and other groups.

The C1–8 alkoxycarbonyl group represented by $R^3$, $R^{3'}$, $R^6$ and $R^{6'}$ may include methoxycarbonyl, ethoxycarbonyl, propoxycarbonyl, isopropoxycarbonyl, butoxycarbonyl, pentyloxycarbonyl, hexyloxycarbonyl, octyloxycarbonyl and other groups.

The C7–11 aralkyloxycarbonyl group represented by $R^3$, $R^{3'}$, $R^6$ and $R^{6'}$ may include benzyloxycarbonyl, β-phenethyl-oxycarbonyl, naphthylmethyloxycarbonyl and other groups. These aryl groups may carry a substituent including a C1–4 alkyl group, a C1–4 polyhaloalkyl group, a halogen atom, a C1–4 alkoxy group, a nitro group, a cyano group, etc. as mentioned above.

The C1–6 alkyl group represented by $R^4$, $R^{4'}$, $R^5$ and $R^{5'}$ may include methyl, ethyl, propyl, isopropyl, butyl, isobutyl, t-butyl, pentyl and other groups. These alkyl groups may carry one or more substituents including a halogen atom or the like, as represented by difluoromethyl, 2,2,2-trifluoroethyl, 3-chloropropyl and other groups.

The C2–6 acyl group represented by $R^4$, $R^{4'}$, $R^5$ and $R^{5'}$ may include acetyl, propionyl, butyryl, isobutyryl, valeryl, isovaleryl and other groups.

The C1–6 alkylsulfonyl group represented by $R^4$, $R^{4'}$, $R^5$ and $R^{5'}$ may include methanesulfonyl, ethanesulfonyl, propanesulfonyl, 2-propanesulfonyl and other groups. These alkylsulfonyl groups may carry one or more substituents including a halogen atom or the like, as represented by trifluoromethanesulfonyl, trichloromethanesulfonyl and other groups.

The arylsulfonyl group represented by $R^4$, $R^{4'}$, $R^5$ and $R^{5'}$ may carry one or more substituents including a halogen atom, a C1–4 alkyl group, a C1–4 polyhaloalkyl group, a C1–4 alkoxy group, a cyano group, a nitro group or the like, as represented by toluenesulfonyl, bromo-benzenesulfonyl, chlorobenzenesulfonyl, fluorobenzenesulfonyl, nitrobenzenesulfonyl, methoxybenzenesulfonyl, trifluoromethylbenzenesulfonyl, trifluoromethoxybenzenesulfonyl and other groups.

The C1–6 alkyl group represented by $R^7$ may include methyl, ethyl, propyl, t-butyl, pentyl, hexyl and other groups.

The C1–8 alkyl group represented by R8 may include methyl, ethyl, propyl, isopropyl, butyl, isobutyl, t-butyl, pentyl, hexyl, octyl and other groups. The C7–11 aralkyl group may include benzyl, α-phenethyl, β-phenethyl, cumyl, naphthylmethyl and other groups.

The substituent A may include those mentioned above for $R^3$. The C1–8 acyl group, C1–6 alkylsulfonyl group or arylsulfonyl group represented by the substituent B may include the same substituents as mentioned above for the acyl group, alkylsulfonyl group or arylsulfonyl group represented by $R^4$ or $R^5$.

The leaving group represented by Y in A—L, B—L and $R^{6'}$—L may include chlorine, bromine and iodine atoms, and trifluoroacetyloxy, methanesulfonyloxy, benzenesulfonyloxy, toluenesulfonyloxy and trifluoromethanesulfonyloxy groups, etc.

Some aryl isocyanate derivatives of the general formula (2) for use in the preparation of hydantoin derivatives of the general formula (1), the compounds of the present invention, are commercially available. Alternatively, they can be prepared easily by reacting aniline derivatives with phosgene or phosgene equivalents in the customary manner. The corresponding aniline derivatives can be produced, for example, by the method described in EP-0496347-A.

Dehydropipecolic acid derivatives of the general formula (3) can be prepared by reacting N-chlorinating agents with pipecolic acid derivatives of the general formula (20), followed by reaction with a base to eliminate hydrogen chloride.

Preferably, the above reaction is performed in an organic solvent. Its examples are aromatic hydrocarbons such as benzene, toluene and xylene, aliphatic hydrocarbons such as hexane, pentane and heptane, ethers such as diethyl ether, tetrahydrofuran, dioxane and 1,2-dimethoxyethane, halogenated hydrocarbons such as methylene chloride, chloroform and carbon tetrachloride, alcohols such as methanol and ethanol, and mixtures of these solvents.

As the N-chlorinating agent, t-butyl hypochlorite can be exemplified. Examples of the usable base are organic amines such as triethylamine, tributylamine, N-methyl-morpholine, pyridine, N,N-dimethylaniline, 1,5-diazabicyclo[5,4,0]-7-undecene, and 1,4-diazabicyclo-[2,2,2]octane; alkali metal bases such as sodium hydride and sodium amide; and alcoholates such as sodium methoxide and sodium ethoxide.

The reaction temperature is selected from the range of from −30° C. to 150° C., and a temperature of 0° to 100° C. is preferred because of a high yield.

The dehydropipecolic acid derivatives of the general formula (3) comprise 1,2-dehydro compounds and 2,3-dehydro compounds in equilibrium condition, and individual isomers and their mixtures are also included in the present invention.

The hydantoin derivatives of the general formula (1) according to the present invention can be prepared, for example, by methods indicated as Step-1 to Step-8. Step-1 shows a method for producing the hydantoin derivative (4) by the addition cyclization reaction between the arylisocyanate derivative or arylisothiocyanate derivative(2) and the dehydropipecolic acid derivative (3).

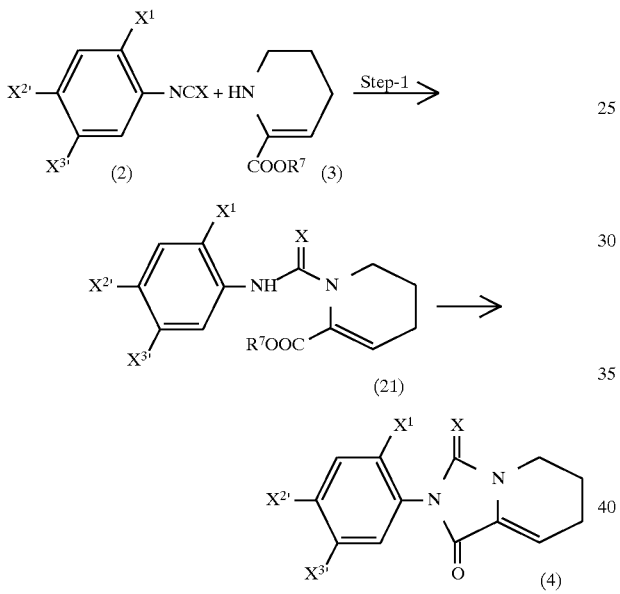

Where $R^7$, X, $X^1$, $X^{2'}$ and $X^{3'}$ are as defined previously.

The process of formation of the hydantoin derivative (4), as revealed above, is such that the amino group of the dehydropipecolic acid derivative (3) is added to the isocyanate group or isothiocyanate group to form a urea intermediate (21), whereafter the amidic nitrogen is cyclized with the carboxyl group in the molecule to give the hydantoin derivative (4). The cyclization reaction of the urea intermediate (21) into the hydantoin derivative (4) is so rapid that the desired product can be obtained in a single step without the isolation of the urea intermediate (21). This reaction is preferably performed in the presence of a base, because that would quicken the reaction and increase the yield. The base, however, is not absolutely necessary, since the dehydropipecolic acid derivative itself is a base. Usable bases include, for example, organic amines such as triethylamine, tributylamine, N-methylmorpholine, pyridine and N,N-dimethylaniline; and alkali metal bases such as potassium carbonate, sodium carbonate, potassium hydrogencarbonate, sodium hydrogencarbonate, sodium hydride and sodium amide.

The amount of the base used is not restricted, but preferably, 0.01 to 2.0 equivalents, more preferably 0.1 to 0.5 equivalent, based on the reaction substrate. Such an amount will increase the yield.

The addition cyclization reaction can be carried out without any solvents, but may employ solvents which will not harm the reaction. Examples of the solvents are aromatic hydrocarbons such as benzene, toluene, xylene and chlorobenzene, aliphatic hydrocarbons such as hexane, pentane and heptane, ethers such as diethyl ether, tetrahydrofuran, dioxane and 1,2-dimethoxyethane, halogenated hydrocarbons such as methylene chloride, chloroform and carbon tetrachloride, ketones such as acetone and methyl ethyl ketone, nitriles such as acetonitrile and propionitrile, esters such as ethyl acetate and ethyl propionate, amides such as N,N-dimethylformamide and N-methylpyrrolidone, and mixtures of these.

The reaction temperature is selected from the range of from −30° C. to 150° C., and a temperature of 0° to 100° C. is preferred because of a high yield.

After completion of the reaction, the desired product can be obtained by an ordinary extraction procedure, but if desired, can be purified by column chromatography.

Step-2 and Step-3 show a method for producing the hydantoin derivative (8). This method comprises hydrolyzing the alkoxycarbonyloxy group at the 5-position of the phenyl ring of the hydantoin derivative (5), i.e., the hydantoin derivative (4) having OCOOR8 as $X^{3'}$ producible by the method shown in Step-1, thereby forming the hydantoin derivative (6), and then reacting this compound with A—L (7) under basic conditions to introduce the substituent A onto the oxygen atom, thereby preparing the hydantoin derivative (8).

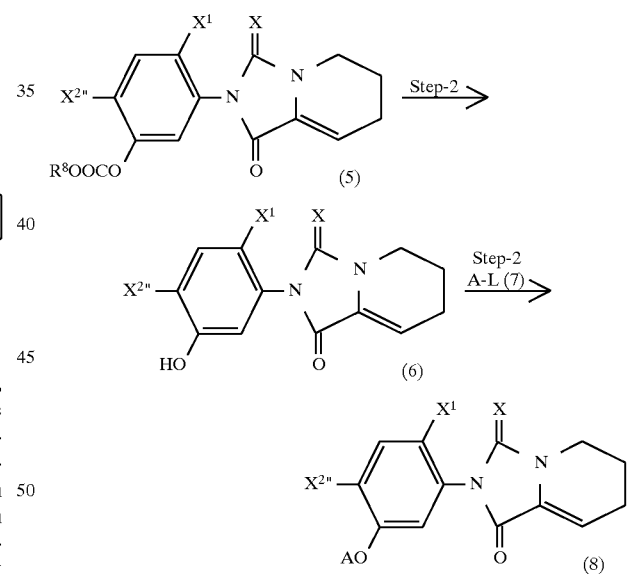

Where A, Y, R8, X, $X^1$ and $X^{2''}$ are as defined previously.

The hydrolysis reaction easily proceeds under acidic or basic conditions. Examples of the usable acid are mineral acids such as hydrochloric acid, sulfuric acid and phosphoric acid. Examples of the usable base are inorganic bases such as potassium hydroxide, sodium hydroxide, potassium carbonate, sodium hydrogencarbonate and potassium hydrogencarbonate, alcoholates such as sodium methoxide and sodium ethoxide.

The amount of the acid or base used is not restricted. Preferably, however, the acid or base is used in at least an equivalent amount based on the reaction substrate. Such an amount will increase the reaction rate and the yield.

The reaction normally uses any solvent which will do no harm to the reaction. Examples of such a solvent are methanol, ethanol, propanol, butanol, toluene, benzene, tetrahydrofuran, acetonitrile, dioxane, water, and mixtures of them.

The reaction temperature is selected from the range of from −10° C. to 150° C. Preferably, the reaction is performed at room temperature to the reflux temperature of the reaction mixture.

After completion of the reaction, the desired product can be obtained by an ordinary isolation procedure, but if desired, can be purified by column chromatography.

The reaction between the hydantoin derivative (6) and the A—L (7) must be performed in the presence of a base. Examples of the usable base are organic amines such as triethylamine, tributylamine, N-methylmorpholine, pyridine and N,N-dimethylaniline; and alkali metal bases such as potassium carbonate, sodium carbonate, potassium hydrogen-carbonate, sodium hydrogencarbonate, sodium hydride and sodium amide. The use of potassium carbonate or sodium carbonate, in particular, can give the desired product in a high yield. The amount of the base used is not restricted. Preferably, however, the base is used in at least an equivalent amount based on the reaction substrate. Such an amount will increase the yield.

The reaction is preferably performed in an organic solvent, and the solvent which will not harm the reaction may be employed. Examples of the solvent are aromatic hydrocarbons such as benzene, toluene, xylene and chlorobenzene, ethers such as diethyl ether, tetrahydrofuran, dioxane and 1,2-dimethoxyethane, halogenated hydrocarbons such as methylene chloride, chloroform and carbon tetrachloride, ketones such as acetone and methyl ethyl ketone, nitriles such as acetonitrile and propionitrile, esters such as ethyl acetate and ethyl propionate, amides such as N,N-dimethylformamide and N-methylpyrrolidone, and mixtures of these.

The reaction proceeds at room temperature. Preferably, however, the reaction is performed with heating at about 50° to 150° C. By so heating, the reaction is completed in a short time, and the yield of the desired product is satisfactory.

After completion of the reaction, the desired product can be obtained by an ordinary isolation procedure, but if desired, can be purified by column chromatography.

Step-4 and Step-5 show a method for producing the hydantoin derivative (12). This method comprises reducing the nitro group to an amino group at the 5-position of the phenyl ring of the hydantoin derivative (9), i.e., the hydantoin derivative (4) having $NO_2$ as $X^{3'}$ producible by the method shown in Step-1, thereby forming the hydantoin derivative (10), and then reacting this compound with B—L (11) to introduce the substituent B onto the nitrogen atom, thereby preparing the hydantoin derivative (12).

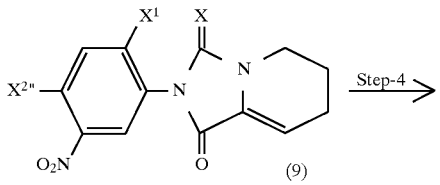

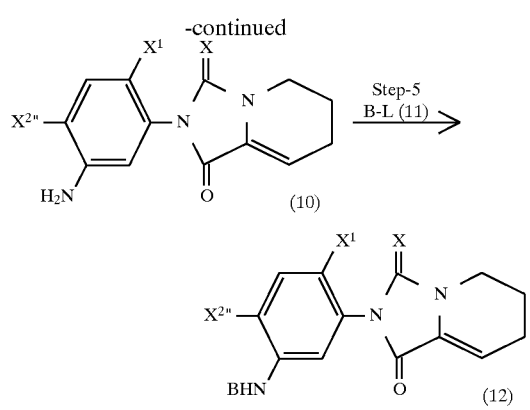

Where B, L, X, $X^1$ and $X^2$ " are as defined previously.

The reduction reaction can employ a reducing agent which will do no harm to other functional groups. For example, metallic reducing agents such as reduced iron, zinc and tin may be used. The reaction is preferably performed in an acetic acid solvent, but can be carried out in a solvent mixture with other solvent such as ethyl acetate. The reaction temperature is selected from the range of from room temperature to 150° C. Preferably, the reaction is performed at the reflux temperature of acetic acid.

After completion of the reaction, the desired product can be obtained by an ordinary extraction procedure, but if desired, can be purified by column chromatography.

The reaction between the hydantoin derivative (10) and the B—L (11) is preferably performed in the presence of a base, because the reaction rate is high and the yield is good. However, the hydantoin derivative (10) is itself a base, so that the use of the base is not compulsory. Examples of the usable base are organic amines such as triethylamine, tributylamine, N-methylmorpholine, pyridine and N,N-dimethylaniline; and alkali metal bases such as potassium carbonate, sodium carbonate, potassium hydrogencarbonate, sodium hydrogencarbonate, sodium hydride and sodium amide. The amount of the base used is not restricted. Preferably, however, the base is used in at least an equivalent amount based on the reaction substrate. Such an amount will increase the yield. When used in an excess amount, the base can also serve as a solvent.

The reaction can be performed in an organic solvent. Examples of the solvent are aromatic hydrocarbons such as benzene, toluene, xylene and chlorobenzene, ethers such as diethyl ether, tetrahydrofuran, dioxane and 1,2-dimethoxyethane, halogenated hydrocarbons such as methylene chloride, chloroform and carbon tetrachloride, ketones such as acetone and methyl ethyl ketone, nitrites such as acetonitrile and propionitrile, esters such as ethyl acetate and ethyl propionate, amides such as N,N-dimethylformamide and N-methylpyrrolidone, and mixtures of these.

The reaction temperature is selected from the range of from −10° to 150° C. Preferably, the reaction is performed at 0° C. to the reflux temperature of the reaction mixture.

After completion of the reaction, the desired product can be obtained by an ordinary extraction procedure, but if desired, can be purified by column chromatography.

Step-6 is a step for producing the hydantoin derivative (15) by the reaction between the hydantoin derivative (13) and a glycolic or thioglycolic acid derivative (14).

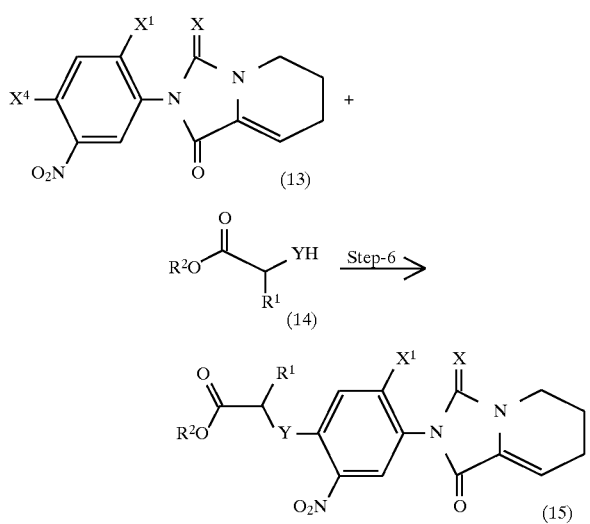

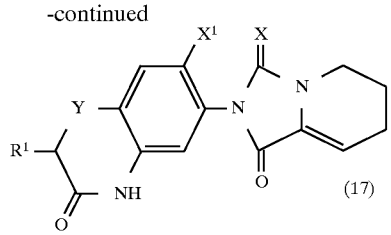

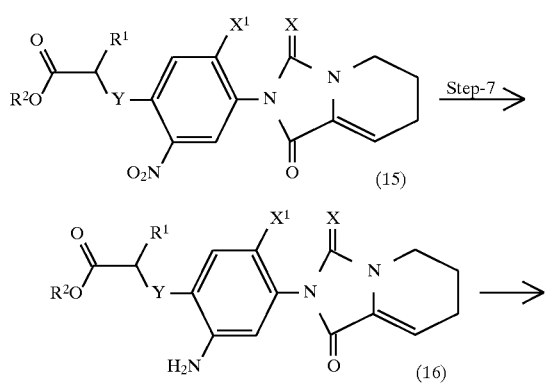

Where $R^1$, $R^2$, $X$, $X^1$, $X^4$ and $Y$ are as defined previously.

This step must be performed in the presence of a base. Examples of the usable base are organic amines such as triethylamine, tributylamine, N-methylmorpholine, pyridine and lutidine; and alkali metal bases such as potassium carbonate, sodium carbonate, sodium acetate, potassium acetate, sodium hydride and sodium amide. The use of sodium hydride or sodium amide, in particular, can give the desired product in a high yield. The amount of the base used is not restricted. Preferably, however, the base is used in at least an equivalent amount based on the reaction substrate. Such an amount will increase the yield.

The reaction may be performed in the absence of a solvent, but can be carried out in an ordinary organic solvent. The usable organic solvent is one which will not harm the reaction. Examples are benzene, toluene, chlorobenzene, ether, dimethoxyethane, dioxane, tetrahydrofuran, N,N-dimethylformamide, and mixtures of these.

The reaction temperature is selected from the range of from −10° to 150° C. After completion of the reaction, the desired product can be obtained by an ordinary extraction procedure, but if desired, can be purified by column chromatography or recrystallization.

Step-7 is a step for producing a bicyclic hydantoin derivative (17) by selectively reducing the nitro group of a bicyclic hydantoin derivative (15) to an amino group.

Where $R^1$, $R^2$, $X$, $X^1$ and $Y$ are as defined previously.

The process of formation of the hydantoin derivative (17), as revealed above, is such that the nitro group of the hydantoin derivative (15) is reduced to an amino group to form a hydantoin derivative (16), whereafter the intramolecular amidation reaction proceeds to give the hydantoin derivative (17). The cyclization reaction of the hydantoin derivative (16), an intermediate, into the hydantoin derivative (17) is so rapid that the desired product can be obtained in a single step without the isolation of the hydantoin derivative (16).

The reduction reaction of the nitro group can employ a reducing agent which will do no harm to other functional groups present. For example, metallic reducing agents such as reduced iron, zinc and tin may be used. The reaction is preferably performed in an aliphatic carboxylic acid solvent, such as acetic acid or propionic acid, but can be carried out in a solvent mixture with other solvent such as ethyl acetate. The reaction temperature is selected from the range of from room temperature to 150° C. Preferably, the reaction is performed at the reflux temperature of the solvent used.

After completion of the reaction, the desired product can be obtained by an ordinary isolation procedure, but if desired, can be purified by column chromatography or recrystallization.

Step-8 is a step for producing a bicyclic hydantoin derivative (19) by introducing a substituent, $R^{6'}$, on the amidic nitrogen atom of the bicyclic hydantoin derivative (17).

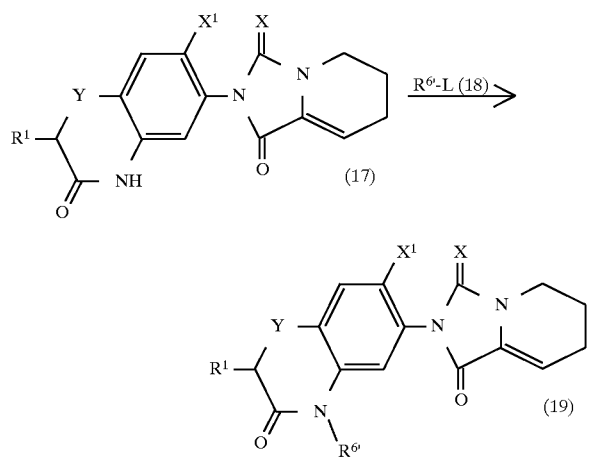

Where $R^1$, $R^{6'}$, $X$, $X^1$, $Y$ and $L$ are as defined previously.

This step must be performed in the presence of a base. Examples of the usable base are organic amines such as triethylamine, tributylamine, N-methylmorpholine, pyridine and lutidine; and alkali metal bases such as potassium carbonate, sodium carbonate, sodium hydride and sodium amide. The use of potassium carbonate, sodium carbonate or sodium hydride, in particular, can give the desired product in a high yield. The amount of the base used is not restricted. Preferably, however, the base is used in at least an equivalent amount based on the reaction substrate. Such an amount will increase the yield.

The reaction is preferably performed in an organic solvent, and the solvent which will not harm the reaction may be employed. Examples of the solvent are aromatic hydrocarbons such as benzene, toluene, xylene and chlorobenzene, ethers such as diethyl ether, tetrahydrofuran, dioxane and 1,2-dimethoxyethane, ketones such as acetone and methyl ethyl ketone, nitriles such as acetonitrile and propionitrile, esters such as ethyl acetate and ethyl propionate, amides such as N,N-dimethyl-formamide and N-methylpyrrolidone, and mixtures of these.

The reaction temperature is selected from the range of −10° to 150° C. Preferably, the reaction is performed at 0° C. to the reflux temperature of the reaction mixture.

After completion of the reaction, the desired product can be obtained by an ordinary isolation procedure, but if desired, can be purified by column chromatography or recrystallization.

BEST MODE FOR CARRYING OUT THE INVENTION

The present invention is further illustrated in detail by the following Examples, Preparation Examples and Test Examples, but these examples are not construed as limiting the present invention.

EXAMPLE-1

Synthesis of ethyl dehydropipecolate

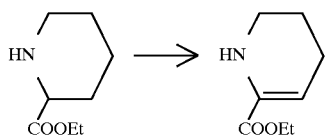

Ethyl pipecolate (7.81 mL, 0.05 mol) and benzene (60 mL) was put in a glass flask under Argon atmosphere, to which a benzene (23 mL) solution of tert-butyl hypochlorite (6.45 mL, 0.06 mol) was added dropwise under cooling in an ice-water bath and stirred for one hour at 0° C. After addition of triethylamine (8.36 mL, 0.06 mol), the reaction mixture was stirred for one hour at room temperature and stirred for further 7 hours at 50° C. The resulting mixture was filtered and the filtrate was evaporated under reduced pressure to give crude product which was purified by distillation under reduced pressure (55°–62° C./0.35 mmHg) to obtain a colorless oil of ethyl dehydropipecolate (5.08 g, yield:65.5%).

$^1$H-NMR(CDCl$_3$ TMS, ppm): δ1.29(t, J=7.25 Hz, 3H), 1.61–1.97(m, 2H), 2.05–2.34(m, 2H), 3.17–3.30(m, 2H), 4.22(q, J=7.25 Hz, 2H), 5.69(t, J=4.17 Hz, 1H).

EXAMPLE-2

Synthesis of 2-(4-chloro-5-cyclopentyloxy-2-fluorophenyl)-5,6-dihydroimidazo [1,5-a] pyridine-1,3[2H, 7H]-dione

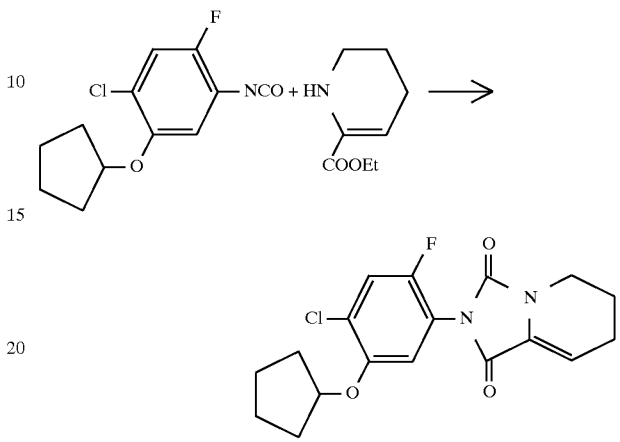

To a toluene (10 mL) solution of ethyl dehydro-pipecolate (0.47 g, 3 mmol) was added a toluene (8 mL) solution of 4-chloro-5-cyclopentyloxy-2-fluorophenyl-isocyanate (0.88 g, 3 mmol) and triethylamine (0.2 mL, 1.5 mmol) under cooling in an ice-water bath. The mixture was stirred for 30 minutes at ambient temperature, for 7 hours at room temperature and for one hour at 60° C., and further stirred for one hour at 80° C. A saturated ammonium chloride solution (30 mL) was added to the resulting mixture, and the organic layer was separated and the aqueous layer was extracted with diethyl ether (20 mL×2 times). The organic layer combined was washed with a saturated sodium chloride solution (50 mL) and dried over anhydrous magnesium sulfate. After removal of magnesium sulfate by filtration, the filtrate was evaporated to give crude product, which was purified by silica gel column (Wakogel C-200, ethyl acetate/hexane=1/2) to obtain a pale yellow oil of 2-(4-chloro-5-cyclopentyloxy-2-fluoro-phenyl)-5,6-dihydroimidazo [1,5-a] pyridine-1,3[2H, 7H]-dione (0.56 g, yield:45.6%).

$^1$H-NMR(CDCl$_3$, TMS, ppm): δ1.70–2.20(m, 10H), 2.23–2.57(m, 2H), 3.75(t, J=5.63 Hz, 2H), 4.62–4.85(m, 1H), 6.22(t, J=4.38 Hz, 1H), 6.87(d, J$_{HF}$=6.30 Hz, 1H), 7.27(d, J$_{HF}$=8.82 Hz, 1H).

EXAMPLE-3

Synthesis of 2-(4-chloro-2-fluoro-5-methoxycarbonyloxyphenyl)-5,6-dihydroimidazo [1, 5-a] pyridine-1,3[2H, 7H]-dione

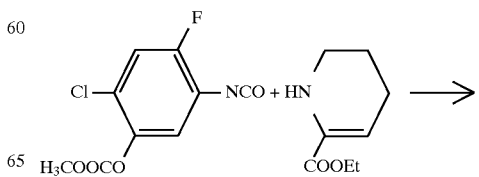

-continued

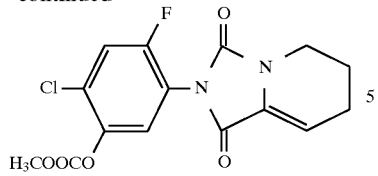

To a toluene (70 mL) solution of ethyl dehydro-pipecolate (2.4 g, 0.02 mol) was dropwise added a toluene (30 mL) solution of 4-chloro-2-fluoro-5-methoxycarbonyl-oxyphenylisocyanate (3.68 g, 0.02 mol) and triethylamine (1.05 mL, 7.5 mmol) under cooling in an ice-water bath. The mixture was stirred for 30 minutes at 0° C. and further stirred for 3 hour at 80° C. A saturated ammonium chloride solution (50 mL) was added to the resulting mixture, and the organic layer was separated and then the aqueous layer was extracted with diethyl ether (50 mL×2 times). The organic layer combined was washed with a saturated sodium chloride solution (30 mL) and dried over anhydrous magnesium sulfate. After removal of magnesium sulfate by filtration, the filtrate was evaporated to give crude product, which was purified by silica gel column (Wakogel C-200, ethyl acetate/hexane=1/1) to obtain a white solid of 2-(4-chloro-2-fluoro-5-methoxycarbonyloxyphenyl)-5,6-dihydroimidazo [1,5-a] pyridine-1,3[2H, 7H]-dione (3.13 g, yield:58.8%).

mp:158°–160° C.;

$^1$H-NMR(CDCl$_3$, TMS, ppm): δ1.81–2.13(m, 2H), 2.23–2.55(m, 2H), 3.64–3.85(m, 2H), 3.92(s, 3H), 6.23(t, J=4.17 Hz, 1H), 7.31(d, J$_{HF}$=6.30 Hz, 1H), 7.37(d, J$_{HF}$=8.82 Hz, 1H).

EXAMPLE-4

Synthesis of 2-(4-chloro-2-fluoro-5-hydroxyphenyl)-5,6-dihydroimidazo [1,5-a] pyridine-1,3[2H, 7H]-dione

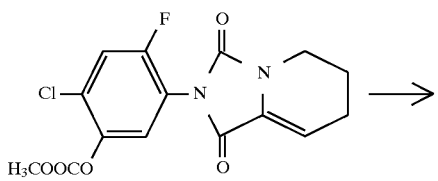

A methanol (40 mL) solution of 2-(4-chloro-2-fluoro-5-methoxycarbonyloxyphenyl)-5,6-dihydroimidazo [1,5-a] pyridine-1,3[2H, 7H]-dione (3.13 g, 8.8 mmol) and potassium carbonate (1.22 g, 8.8 mmol) was stirred at 50°–60° C. for 8 hours. Diethyl ether (20 mL) and 1N hydrochloric acid (30 mL) were added to the resulting mixture, and the organic layer was separated and then the aqueous layer was extracted with diethyl ether (20 mL×2 times). The organic layer combined was washed with a saturated sodium chloride solution (30 mL) and dried over anhydrous magnesium sulfate. After removal of magnesium sulfate by filtration, the filtrate was evaporated to give crude product, which was purified by silica gel column (Wakogel C-200, ethyl acetate/hexane=1/1) to obtain a white solid of 2-(4-chloro-2-fluoro-5-hydroxyphenyl)-5,6-dihydroimidazo [1,5-a] pyridine-1,3 [2H, 7H]-dione (0.93 g, yield:5.8%).

$^1$H-NMR(CDCl$_3$, TMS, ppm): δ1.80–2.13(m, 2H), 2.23–2.55(m, 2H), 3.73(t, J=5.63 Hz, 2H), 6.26(t, J=4.38 Hz, 1H), 6.90(d, J$_{HF}$=6.30 Hz, 1H), 7.20(d, J$_{HF}$=8.82 Hz, 1H).

EXAMPLE-5

Synthesis of 2-(4-chloro-2-fluoro-5-methyloxyphenyl)-5,6-dihydroimidazo [1,5-a] pyridine-1,3[2H, 7H]-dione

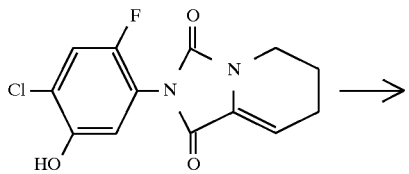

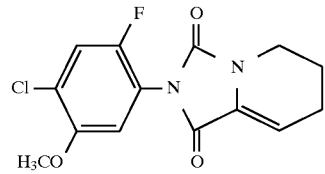

An acetonitrile (15 mL) solution of 2-(4-chloro-2-fluoro-5-hydroxyphenyl)-5,6-dihydroimidazo [1,5-a] pyridine-1,3 [2H, 7H]-dione (0.78 g, 2.63 mmol), potassium carbonate (0.27 g, 1.97 mmol) and methyliodide (0.33 mL, 5.26 mmol) was stirred for 6.5 hours under reflux. A saturated ammonium chloride solution (15 mL) and diethyl ether (15 mL) were added to the resulting mixture, and the organic layer was separated and then the aqueous layer was extracted with diethyl ether (15 mL×2 times). The organic layer combined was washed with a saturated sodium chloride solution (20 mL) and dried over anhydrous magnesium sulfate. After removal of magnesium sulfate by filtration, the filtrate was evaporated to give crude product, which was purified by silica gel column (Wakogel C-200, ethyl acetate/hexane=1/1) to obtain a white solid of 2-(4-chloro-2-fluoro-5-methyloxyphenyl)-5,6-dihydroimidazo [1,5-a] pyridine-1,3 [2H, 7H]-dione (0.36 g, yield:44.3%).

$^1$H-NMR(CDCl$_3$, TMS, ppm): δ1.90–2.15(m, 2H), 2.30–2.55(m, 2H), 3.76(t, J=5.63 Hz, 2H), 3.88(s, 3H), 6.25(t, J=4.38 Hz, 1H), 6.87(d, J$_{HF}$=6.30 Hz, 1H), 7.30(d, J$_{HF}$=8.82 Hz, 1H).

mp:134°–137° C.

EXAMPLE-6

Synthesis of 2-(5-allyloxy-4-chloro-2-fluorophenyl)-5,6-dihydroimidazo [1,5-a] pyridine-1,3[2H, 7H]-dione

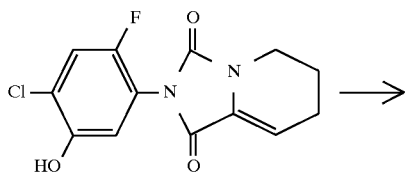

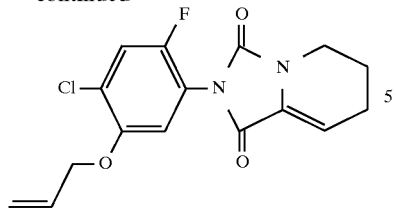

An acetonitrile (10 mL) solution of 2-(4-chloro-2-fluoro-5-hydroxyphenyl)-5,6-dihydroimidazo [1,5-a] pyridine-1,3 [2H, 7H]-dione (0.69 g, 2.33 mmol), potassium carbonate (0.24 g, 1.74 mmol) and allylbromide (0.22 mL, 2.56 mmol) was stirred for 4.5 hours under reflux. A saturated ammonium chloride solution (10 mL) and diethyl ether (10 mL) were added to the resulting mixture, and the organic layer was separated and then the aqueous layer was extracted with diethyl ether (10 mL×2 times). The organic layer combined was washed with a saturated sodium chloride solution (15 mL) and dried over anhydrous magnesium sulfate. After removal of magnesium sulfate by filtration, the filtrate was evaporated to give crude product, which was purified by silica gel column (Wakogel C-200, ethyl acetate/hexane=1/2) to obtain a white solid of 2-(5-allyloxy-4-chloro-2-fluorophenyl)-5,6-dihydroimidazo [1,5-a] pyridine-1,3[2H, 7H]-dione (0.47 g, yield:62.9%).

$^1$H-NMR(CDCl$_3$, TMS, ppm): δ1.80–2.20(m, 2H), 2.20–2.60(m, 2H), 3.75(t, J=5.63 Hz, 2H), 4.60(d, J=5.0 Hz, 2H), 5.20–5.70(m, 2H), 5.80–6.16(m, 1H), 6.23(t, J=4.38 Hz, 1H), 6.90(d, J$_{HF}$=6.30 Hz, 1H), 7.31(d, J$_{HF}$=8.82 Hz, 1H).

mp:159°–162° C.

EXAMPLE-7

Synthesis of 2-(4-chloro-2-fluoro-5-propargyloxyphenyl)-5,6-dihydroimidazo [1,5-a] pyridine-1,3[2H, 7H]-dione

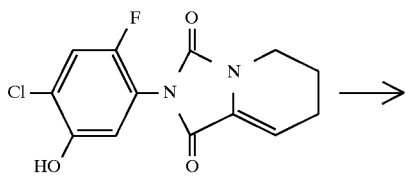

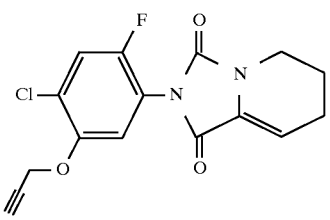

An acetonitrile (15 mL) solution of 2-(4-chloro-2-fluoro-5-hydroxyphenyl)-5,6-dihydroimidazo [1,5-a] pyridine-1,3 [2H, 7H]-dione (0.82 g, 2.76 mmol), potassium carbonate (0.29 g, 2.07 mmol) and propargylbromide (0.27 mL, 3.04 mmol) was stirred fir 4.5 hours under reflux. A saturated ammonium chloride solution (15 mL) and diethyl ether (15 mL) were added to the resulting mixture, and the organic layer was separated and then the aqueous layer was extracted with diethyl ether (15 mL×2 times). The organic layer combined was washed with a saturated sodium chloride solution (20 mL) and dried over anhydrous magnesium sulfate. After removal of magnesium sulfate by filtration, the filtrate was evaporated to give crude product, which was purified by silica gel column (Wakogel C-200, ethyl acetate/hexane=1/2) to obtain a pale yellow solid of 2-(4-chloro-2-fluoro-5-propargyloxyphenyl)-5,6-dihydroimidazo [1,5-a] pyridine-1,3[2H, 7H]-dione (0.50 g, yield:56.6%).

$^1$H-NMR(CDCl$_3$, TMS, ppm): δ1.73–2.17(m, 2H), 2.30–2.53(m, 2H), 2.58(t, J=2.50 Hz, 1H), 3.75(t, J=5.63 Hz, 2H), 4.75(d, J=2.50 Hz, 2H), 6.23(t, J=4.38 Hz, 1H), 7.05(d, J$_{HF}$=6.30 Hz, 1H), 7.31(d, J$_{HF}$=8.82 Hz, 1H).

mp:161°–164° C.

EXAMPLE-8

Synthesis of 2-(4-chloro-2-fluoro-5-methylpropargyloxyphenyl)-5,6-dihydroimidazo [1,5-a] pyridine-1,3[2H, 7H]-dione

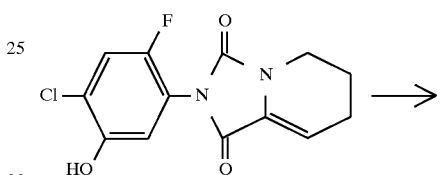

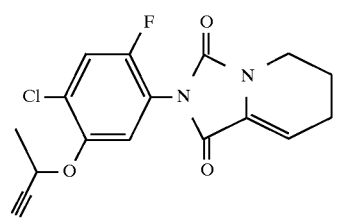

An acetonitrile (10 mL) solution of 2-(4-chloro-2-fluoro-5-hydroxyphenyl)-5,6-dihydroimidazo [1,5-a] pyridine-1,3 [2H, 7H]-dione (0.21 g, 0.70 mmol), potassium carbonate (0.01 g, 0.7 mmol) and methylpropargyltosylate (0.17 g, 0.77 mmol) was stirred for 2.5 hours under reflux. A saturated ammonium chloride solution (10 mL) and diethyl ether (10 mL) were added to the resulting mixture, and the organic layer was separated and then the aqueous layer was extracted with diethyl ether (150 mL×2 times). The organic layer combined was washed with a saturated sodium chloride solution (15 mL) and dried over anhydrous magnesium sulfate. After removal of magnesium sulfate by filtration, the filtrate was evaporated to give crude product, which was purified by silica gel column (Wakogel C-200, ethyl acetate/hexane=1/2) to obtain a white solid of 2-(4-chloro-2-fluoro-5-methylpropargyloxyphenyl)-5,6-dihydroimidazo [1,5-a] pyridine-1,3[2H, 7H]-dione (0.08 g, yield:32.9%).

$^1$H-NMR(CDCl$_3$, TMS, ppm): δ1.70(d, J=6.88 Hz, 3H), 1.80–2.20(m, 2H), 2.26–2.50(m, 2H), 2.55(d, J=2.55 Hz, 1H), 3.75(t, J=5.63 Hz, 2H), 4.86(dq, J=6.88 and 2.55 Hz, 1H), 6.23(t, J=4.38 Hz, 1H), 7.13(d, J$_{HF}$=6.30 Hz, 1H), 7.30(d, J$_{HF}$=8.82 Hz, 1H).

mp:130°–132° C.

EXAMPLE-9

Synthesis of 2-(4-chloro-5-cyclopentyloxy-2-fluorophenyl)-5,6-dihydroimidazo [1,5-a] pyridine-1,3[2H, 7H]-dione

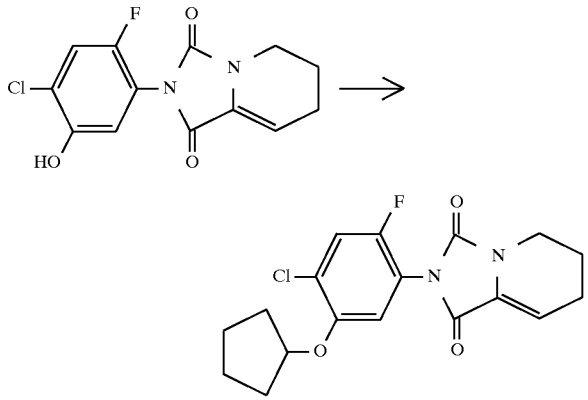

An acetonitrile (20 mL) solution of 2-(4-chloro-2-fluoro-5-hydroxyphenyl)-5,6-dihydroimidazo [1,5-a] pyridine-1,3 [2H, 7H]-dione (0.46 g, 1.54 mmol), potassium carbonate (0.16 g, 1.16 mmol) and cyclopentylbromide (0.18 mL, 1.69 mmol) was stirred for 2 hours under reflux. A saturated ammonium chloride solution (20 mL) and diethyl ether (20 mL) were added to the resulting mixture, and the organic layer was separated and then the aqueous layer was extracted with diethyl ether (20 mL×2 times). The organic layer combined was washed with a saturated sodium chloride solution (25 mL) and dried over anhydrous magnesium sulfate. After removal of magnesium sulfate by filtration, the filtrate was evaporated to give crude product, which was purified by silica gel column (Wakogel C-200, ethyl acetate/hexane=1/1) to obtain a pale yellow oil of 2-(4-chloro-5-cyclopentyloxy-2-fluorophenyl)-5,6-dihydroimidazo [1,5-a] pyridine-1,3[2H, 7H]-dione (0.49 g, yield:87.5%).

$^1$H-NMR(CDCl$_3$, TMS, ppm): δ1.70–2.20(m, 10H), 2.23–2.57(m, 2H), 3.75(t, J=5.63 Hz, 2H), 4.62–4.85(m, 1H), 6.22(t, J=4.38 Hz, 1H), 6.87(d, J$_{HF}$=6.30 Hz, 1H), 7.27(d, J$_{HF}$=8.82 Hz, 1H).

EXAMPLE-10

Synthesis of 2-(4-chloro-2-fluoro-5-pentyloxycarbonyl-methoxyphenyl)-5,6-dihydroimidazo [1,5-a] pyridine-1,3[2H, 7H]-dione

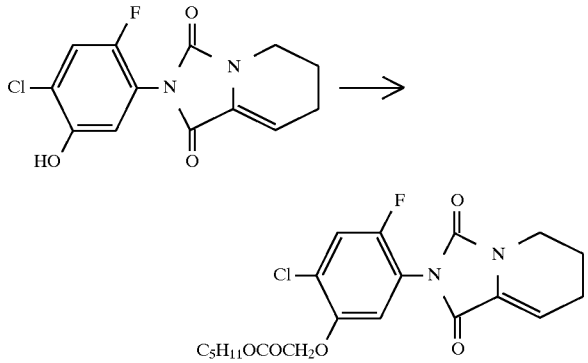

To an acetonitrile (7 mL) solution of 2-(4-chloro-2-fluoro-5-hydroxyphenyl)-5,6-dihydroimidazo [1,5-a] pyridine-1,3 [2H, 7H]-dione (0.59 g, 2.0 mmol), potassium carbonate (0.21 g, 1.50 mmol) and potassium iodide (0.03 g, 0.2 mmol) was dropwise added an acetonitrile (3 mL) solution of pentyl chloroacetate (0.36 g, 2.2 mmol) at room temperature and the mixture was stirred for 3 hours under reflux. A saturated ammonium chloride solution (10 mL) and diethyl ether (10 mL) were added to the resulting mixture, and the organic layer was separated and then the aqueous layer was extracted with diethyl ether (10 mL×2 times). The organic layer combined was washed with a saturated sodium chloride solution (15 mL) and dried over anhydrous magnesium sulfate. After removal of magnesium sulfate by filtration, the filtrate was evaporated to give crude product, which was purified by silica gel column (Wakogel C-200, ethyl acetate/hexane=1/1) to obtain a white solid of 2-(4-chloro-2-fluoro-5-(pentyloxycarbonyl-methoxy)- 5,6-dihydroimidazo [1,5-a] pyridine-1,3[2H, 7H]-dione (0.77 g, yield:90.6%).

$^1$H-NMR(CDCl$_3$, TMS, ppm): δ0.90(t, J=7.25 Hz, 3H), 1.10–1.50(m, 6H), 1.90–2.23(m, 2H), 2.25–2.55(m, 2H), 3.76(t, J=5.63 Hz, 2H), 4.22(t, J=7.25 Hz, 2H), 4.68(s, 2H), 6.23(t, J=4.38 Hz, 1H), 6.91(d, J$_{HF}$=6.30 Hz, 1H), 7.32(d, J$_{HF}$=8.82 Hz, 1H).

mp:134°–136° C.

EXAMPLE-11

Synthesis of 2-(2,4-difluoro-5-nitrophenyl)-5,6-dihydroimidazo [1,5-a] pyridine-1,3[2H, 7H]-dione

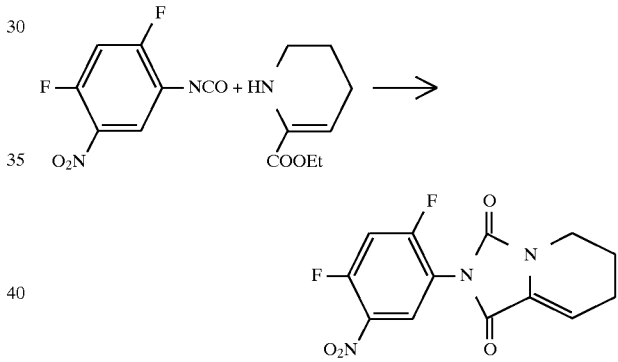

To a toluene (200 mL) solution of ethyl dehydropipecolate (10.7 g, 0.07 mol) was added a toluene (100 mL) solution of 2,4-difluoro-5-nitrophenylisocyanate (13.9 g, 0.07 mol) and then triethylamine (4.8 mL, 0.04 mol) under cooling in an ice-water bath. The reaction mixture was stirred for 30 minutes at ambient temperature and for 3 hours at room temperature, and further stirred at 80° C. for 6 hours. A saturated ammonium chloride solution (250 mL) was added to the resulting mixture, and the organic layer was separated and then the aqueous layer was extracted with diethyl ether (200 mL×2 times). The organic layer combined was washed with a saturated sodium chloride solution (300 mL) and dried over anhydrous magnesium sulfate. After removal of magnesium sulfate by filtration, the filtrate was evaporated to give crude product, which was purified by crystallization from a mixed-solvent of dichloromethane and hexane to obtain white crystals of 2-(2, 4-difluoro-5-nitrophenyl)-5,6-dihydroimidazo [1,5-a] pyridine-1,3[2H, 7H]-dione (16.8 g, yield:78.8%).

$^1$H-NMR(CDCl$_3$, TMS, ppm): δ1.83–2.09(m, 2H), 2.31–2.69(m, 2H), 3.79(t, J=5.94 Hz, 2H), 6.30(t, J=4.38 Hz, 1H), 7.24(t, J$_{HF}$=9.38 Hz, 1H), 8.21(t, J$_{HF}$=7.50 Hz, 1H).

mp:138°–140° C.

EXAMPLE-12

Synthesis of 2-(4-chloro-2-fluoro-5-nitrophenyl)-5,6-dihydroimidazo [1,5-a] pyridine-1,3[2H, 7H]-dione

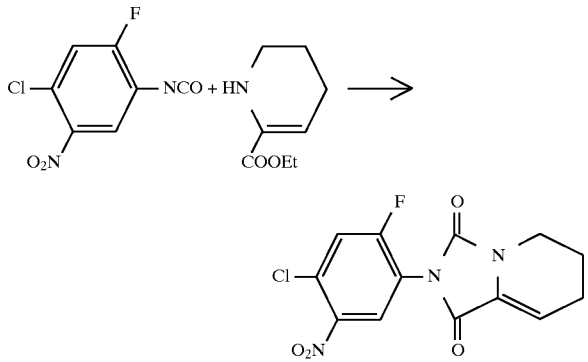

To a toluene (100 mL) solution of ethyl dehydropipecolate (3.85 g, 0.025 mol) was dropwise added a toluene (60 mL) solution of 4-chloro-2-fluoro-5-nitrophenyl-isocyanate (5.37 g, 0.025 mol) and triethylamine (1.74 mL, 0.013 mol) under cooling in an ice-water bath. The reaction mixture was stirred for 30 minutes at 0° C. and for 3 hours at room temperature, and further stirred at 80° C. for 5 hours. A saturated ammonium chloride solution (150 mL) was added to the resulting mixture, and the organic layer was separated and then the aqueous layer was extracted with diethyl ether (100 mL×2 times). The organic layer combined was washed with a saturated sodium chloride solution (150 mL) and dried over anhydrous magnesium sulfate. After removal of magnesium sulfate by filtration, the filtrate was evaporated to give crude product, which was purified by crystallization from a mixed-solvent of dichloromethane and hexane to obtain white crystals of 2-(4-chloro-2-fluoro-5-nitrophenyl)-5,6-dihydroimidazo [1,5-a] pyridine-1,3[2H, 7H]-dione (5.14 g, yield:63.1%).

$^1$H-NMR(CDCl$_3$, TMS, ppm): δ1.80–2.20(m, 2H), 2.30–2.60(m, 2H), 3.79(t, J=5.68 Hz, 2H), 6.30(t, J=4.23 Hz, 1H), 7.50(d, J$_{HF}$=8.82 Hz, 1H), 8.08(d, J$_{HF}$=6.30 Hz, 1H).

mp:145°–147° C.

EXAMPLE-13

Synthesis of 2-(5-amino-4-chloro-2-fluorophenyl)-5,6-dihydroimidazo [1,5-a] pyridine-1,3[2H, 7H]-dione

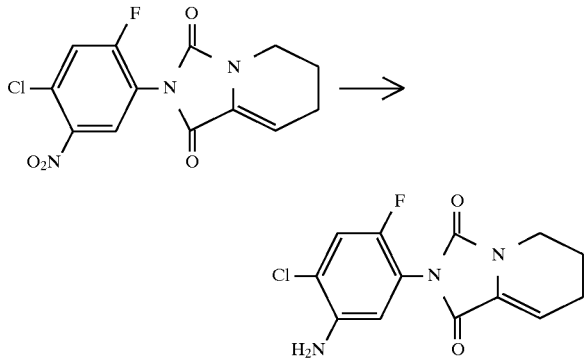

After an acetic acid (172 mL) solution of reduced iron (21.0 g) was stirred for one hour under reflux, an ethyl acetate (113 mL) solution of 2-(4-chloro-2-fluoro-5-nitrophenyl)-5,6-dihydroimidazo [1,5-a] pyridine-1,3[2H, 7H]-dione (5.14 g, 0.016 mol) was dropwise added to the mixture at the same temperature. The reaction mixture was stirred for 2 hours under reflux and cooled down to room temperature. After filtration of the resulting mixture, 1N hydrochloric acid (250 mL) was added to the filtrate, and the organic layer was separated and the aqueous layer was extracted with ethyl acetate (100 mL×2 times). The organic layer combined was washed with water (300 mL) and dried over anhydrous magnesium sulfate. After removal of magnesium sulfate by filtration, the filtrate was evaporated to give crude product, which was purified by silica gel column (Wakogel C-200, ethyl acetate/hexane =1/1) to obtain a white solid of 2-(5-amino-4-chloro-2-fluorophenyl)-5,6-dihydroimidazo [1,5-a] pyridine-1,3[2H, 7H]-dione (2.81 g, yield:59.4%).

$^1$H-NMR(CDCl$_3$, TMS, ppm): δ1.76–2.18(m, 2H), 2.25–2.60(m, 2H), 3.75(t, J=5.68 Hz, 2H), 4.03(brs, 2H), 6.23(t, J=4.38 Hz, 1H), 6.72(d, J$_{HF}$=6.25 Hz, 1H), 7.19(d, J$_{HF}$=9.75 Hz, 1H).

mp:153°–155° C.

EXAMPLE-14

Synthesis of 2-(5-acetylamino-4-chloro-2-fluorophenyl)-5,6-dihydroimidazo [1,5-a] pyridine-1,3[2H, 7H]-dione

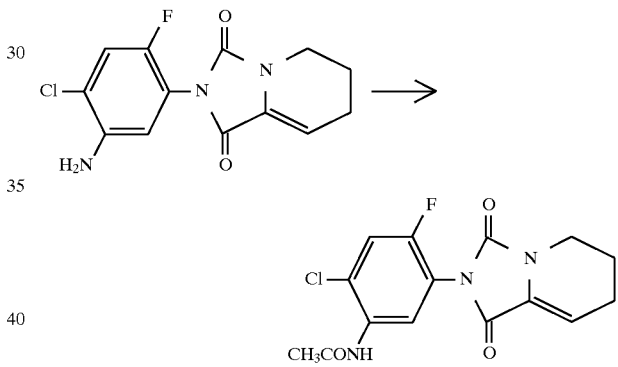

To an tetrahydrofuran (5 mL) solution of 2-(5-amino-4-chloro-2-fluorophenyl)-5,6-dihydroimidazo [1,5-a] pyridine-1,3[2H, 7H]-dione (0.50 g, 1.69 mmol) were dropwise added acetic anhydride (0.18 mL, 1.86 mmol) and pyridine (8 drops) with stirring at room temperature. The reaction mixture was stirred for 8 hours at room temperature and further stirred for 13 hours at 80° C. 1N Hydrochloric acid (20 mL) and ethyl acetate (20 mL) were added to the resulting mixture, and the organic layer was separated and the aqueous layer was extracted with ethyl acetate (20 mL×2 times). The organic layer combined was washed with saturated sodium chloride solution (30 mL) and dried over anhydrous magnesium sulfate. After removal of magnesium sulfate by filtration, the filtrate was evaporated to give crude product, which was purified by silica gel column (Wakogel C-200, ethyl acetate/hexane =1/1) to obtain a white solid of 2-(5-acetylamino-4-chloro-2-fluorophenyl)-5,6-dihydroimidazo [1,5-a] pyridine-1,3[2H, 7H]-dione (0.34 g, yield:59.6%).

$^1$H-NMR(CDCl$_3$, TMS, ppm): δ1.85–2.10(m, 2H), 2.20 (s, 3H), 2.30–2.55(m, 2H), 3.76(t, J=5.63 Hz, 2H), 6.24(t, J=4.38 Hz, 1H), 7.26(d, J$_{HF}$=8.82 Hz, 1H), 7.74(brs, 1H), 8.45(d, J$_{HF}$=7.56 Hz, 1H).

mp:196°–198° C.

EXAMPLE-15

Synthesis of 2-(4-chloro-2-fluoro-5-methanesulfonyl-aminophenyl)-5,6-dihydroimidazo [1,5-a] pyridine-1,3[2H, 7H]-dione

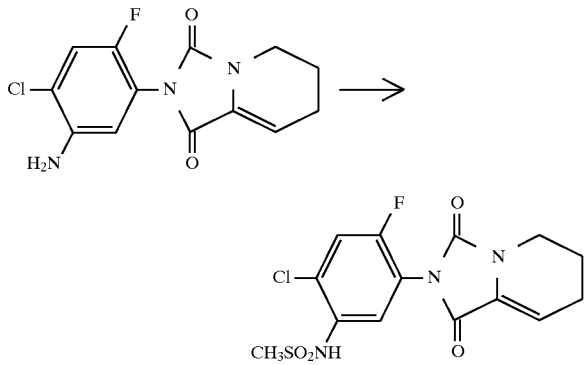

To a pyridine (5 mL) solution of 2-(5-amino-4-chloro-2-fluorophenyl)-5,6-dihydroimidazo [1,5-a] pyridine-1, 3[2H, 7H]-dione (0.50 g, 1.69 mmol) was added methanesulfonyl chloride (0.14 mL, 1.86 mmol) with stirring under cooling in an ice-water bath and the reaction mixture was stirred for 2 hours at 0° C. The resulting mixture was quenched with 1N hydrochloric acid (60 mL) and extracted with ethyl acetate (20 mL×3 times). The organic layer combined was washed with saturated sodium chloride solution (20 mL) and dried over anhydrous magnesium sulfate. After removal of magnesium sulfate by filtration, the filtrate was evaporated to give crude product, which was purified by silica gel column (Wakogel C-200, ethyl acetate/hexane=1/1) to obtain a white solid of 2-(4-chloro-2-fluoro-5-methanesulfonylaminophenyl)-5,6-dihydroimidazo [1,5-a] pyridine-1,3[2H, 7H]-dione (0.46 g, yield:73.0%).

$^1$H-NMR(CDCl$_3$, TMS, ppm): δ1.85–2.18(m, 2H), 2.30–2.58(m, 2H), 3.05(s, 3H), 3.78(t, J=5.68 Hz, 2H), 6.27(t, J=4.38 Hz, 1H), 6.96(bs, 1H), 7.38(d, J$_{HF}$=8.82 Hz, 1H), 7.69(d, J$_{HF}$=6.30 Hz, 1H).

mp:106°–108° C.

EXAMPLE-16

Synthesis of 2-[4-chloro-2-fluoro-5-(3-oxo-2-butyloxy)-phenyl]-5,6-dihydroimidazo [1,5-a] pyridine-1,3[2H, 7H]-dione

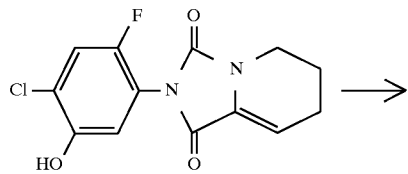

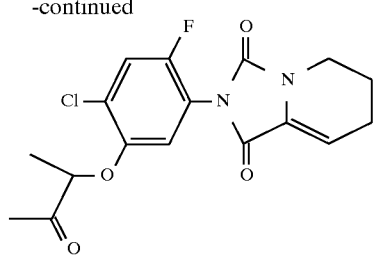

An acetonitrile (10 mL) solution of 2-(4-chloro-2-fluoro-5-hydroxyphenyl)-5,6-dihydroimidazo [1,5-a] pyridine-1,3 [2H, 7H]-dione (0.57 g, 1.9 mmol), potassium carbonate (0.29 g, 2.1 mmol) and 3-chloro-2-butanone (0.21 mL, 2.1 mmol) was stirred for 5 hours under reflux. A saturated ammonium chloride solution (10 mL) was added to the resulting mixture, and the organic layer was separated and then the aqueous layer was extracted with diethyl ether (10 mL×2 times). The organic layer combined was washed with a saturated sodium chloride solution (20 mL) and dried over anhydrous magnesium sulfate. After removal of magnesium sulfate by filtration, the filtrate was evaporated to give crude product, which was purified by silica gel column (Wakogel C-200, ethyl acetate/hexane =1/2) to obtain a white solid of 2-[4-chloro-2-fluoro-5-(3-oxo-2-butyloxy)phenyl]-5,6-dihydroimidazo [1,5-a] pyridine-1,3[2H, 7H]-dione (0.64 g, yield:86.5%).

$^1$H-NMR(CDCl$_3$, TMS, ppm): δ1.54(d, J=7.56 Hz, 3H), 1.90–2.20(m, 2H), 2.27(s, 3H), 2.21–2.60(m, 2H), 3.73(t, J=6.30 Hz, 2H), 4.62(q, J=6.30 Hz, 1H), 6.25(t, J=3.78 Hz, 1H), 6.76(d, J$_{HF}$=6.30 Hz, 1H), 7.32(d, J$_{HF}$=10.08 Hz, 1H).

mp:93°–95° C.

EXAMPLE-17

Synthesis of 2-(5-acetonyloxy-4-chloro-2-fluorophenyl)-5,6-dihydroimidazo [1,5-a] pyridine-1,3[2H, 7H]-dione

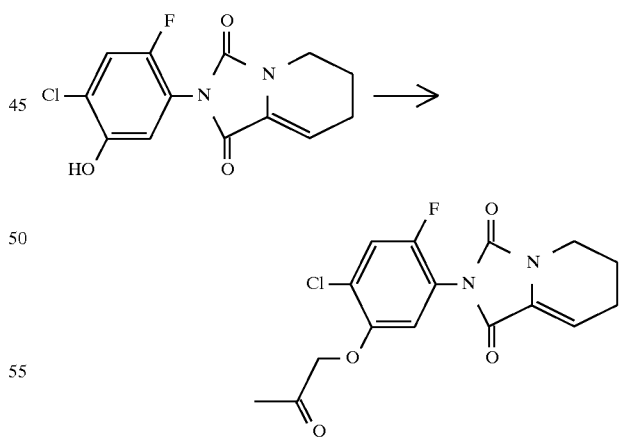

An acetonitrile (10 mL) solution of 2-(4-chloro-2-fluoro-5-hydroxyphenyl)-5,6-dihydroimidazo [1,5-a] pyridine-1,3 [2H, 7H]-dione (0.59 g, 2.0 mmol), potassium carbonate (0.2 g, 2.2 mmol) and chloroacetone (0.18 mL, 2.2 mmol) was stirred for 5 hours under reflux. A saturated ammonium chloride solution (10 mL) was added to the resulting mixture, and the organic layer was separated and then the aqueous layer was extracted with diethyl ether (10 mL×2 times). The organic layer combined was washed with a saturated sodium chloride solution (20 mL) and dried over anhydrous magnesium sulfate. After removal of magnesium sulfate by filtration, the filtrate was evaporated to give crude product, which was purified by silica gel column (Wakogel C-200, ethyl acetate/hexane =1/2) to obtain a white solid of 2-(5-acetonyloxy-4-chloro-2-fluorophenyl)-5,6-dihydroimidazo [1,5-a] pyridine-1, 3[2H, 7H]-dione (0.50 g, yield:70.4%).

$^1$H-NMR(CDCl$_3$, TMS, ppm): δ1.85–2.18(m, 2H), 2.34 (s, 3H), 2.27–2.55(m, 2H), 3.74(t, J=6.30 Hz, 2H), 4.53(s, 2H), 6.22(t, J=5.04 Hz, 1H), 6.79(d, $J_{HF}$=6.30 Hz, 1H), 7.33(d, $J_{HF}$=8.82 Hz, 1H).

mp:168°–170° C.

EXAMPLE-18

Synthesis of 2-(4-chloro-2-fluoro-5-methoxycarbonyl-methoxyphenyl)-5,6-dihydroimidazo [1,5-a] pyridine-1,3[2H, 7H]-dione

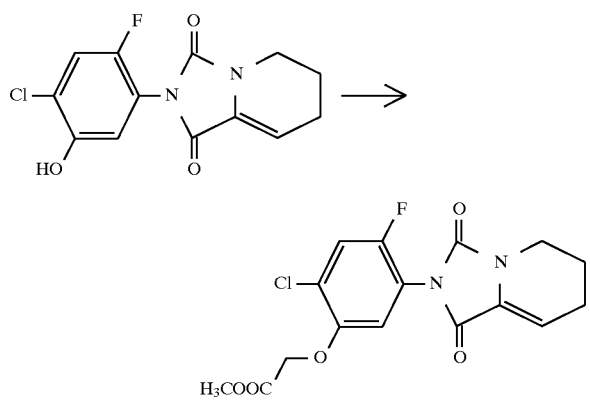

An acetonitrile (10 mL) solution of 2-(4-chloro-2-fluoro-5-hydroxyphenyl)-5,6-dihydroimidazo [1,5-a] pyridine-1,3 [2H, 7H]-dione (0.59 g, 2.0 mmol), potassium carbonate (0.2 g, 2.2 mmol) and methyl chloroacetate (0.2 mL, 2.2 mmol) was stirred for 5 hours under reflux. A saturated ammonium chloride solution (10 mL) was added to the resulting mixture, and the organic layer was separated and then the aqueous layer was extracted with diethyl ether (10 mL×2 times). The organic layer combined was washed with a saturated sodium chloride solution (20 mL) and dried over anhydrous magnesium sulfate. After removal of magnesium sulfate by filtration, the filtrate was evaporated to give crude product, which was purified by silica gel column (Wakogel C-200, ethyl acetate/hexane =1/2) to obtain 2-(4-chloro-2-fluoro-5-methoxycarbonyl-methoxyphenyl)-5,6-dihydroimidazo [1,5-a] pyridine-1,3[2H, 7H]-dione (0.64 g, yield:86.5%).

$^1$H-NMR(CDCl$_3$, TMS, ppm): δ1.85–2.17(m, 2H), 2.30–2.60(m, 2H), 3.68–3.91(m, 5H), 4.70(s, 2H), 6.25(t, J=3.78 Hz, 1H), 6.91(d, $J_{HF}$=6.30 Hz, 1H), 7.35(d, $J_{HF}$=8.82 Hz, 1H).

mp:148°–150° C.

EXAMPLE-19

Synthesis of 2-(2-chloro-4-methyl-5-methoxycarbonyloxyphenyl)-5,6-dihydroimidazo [1, 5-a] pyridine-1,3[2H, 7H]-dione

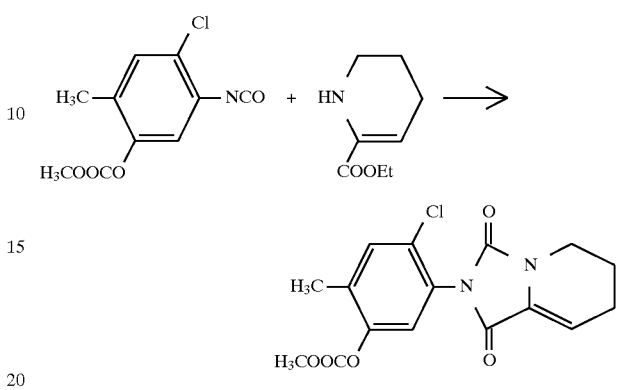

To a toluene (55 mL) solution of ethyl dehydropipecolate (1.81 g, 12 mmol) was dropwise added a toluene (25 mL) solution of 2-chloro-4-methyl-5-methoxycarbonyl-oxyphenylisocyanate (2.98 g, 12 mmol) and triethylamine (0.84 mL, 6 mmol) under cooling in an ice-water bath. The mixture was stirred for 30 minutes at ambient temperature and for 16 hour at room temperature, and further stirred for 5 hour at 80° C. A saturated ammonium chloride solution (80 mL) was added to the resulting mixture, and the organic layer was separated and then the aqueous layer was extracted with ethyl acetate (40 mL×2 times). The organic layer combined was washed with a saturated sodium chloride solution (160 mL) and dried over anhydrous magnesium sulfate. After removal of magnesium sulfate by filtration, the filtrate was evaporated to give crude product, which was purified by silica gel column (Wakogel C-200, ethyl acetate/hexane=1/3-1/1) to obtain a white solid of 2-(2-chloro-4-methyl-5-methoxycarbonyloxyphenyl)-5,6-dihydroimidazo [1,5-a] pyridine-1,3[2H, 7H]-dione (2.22 g, yield:50.7%).

$^1$H-NMR(CDCl$_3$, TMS, ppm): δ1.85–2.15(m, 2H), 2.22 (s, 3H), 2.30–2.58(m, 2H), 3.76(t, J=5.04 Hz, 2H), 3.95(s, 3H), 6.25(t, J=3.78 Hz, 1H), 7.18(s, 1H), 7.45(s, 1H).

EXAMPLE-20

Synthesis of 2-(2-chloro-4-methyl-5-hydroxyphenyl)-5,6-dihydroimidazo [1,5-a] pyridine-1,3[2H, 7H]-dione

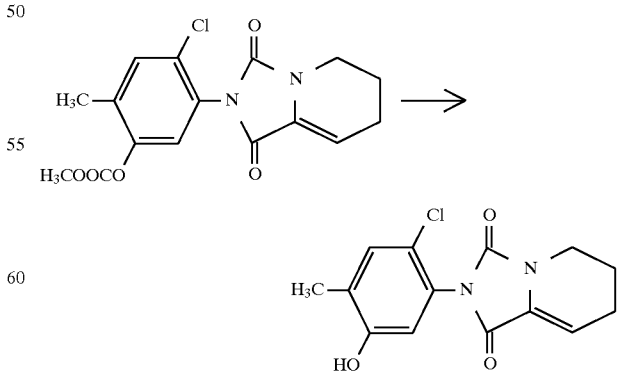

A methanol (45 mL) solution of 2-(2-chloro-4-methyl-5-methoxycarbonyloxyphenyl)-5,6-dihydroimidazo [1,5-a]

pyridine-1,3[2H, 7H]-dione (2.22 g, 6.08 mmol) and potassium carbonate (0.84 g, 6.08 mmol) was stirred at 50°–60° C. for 7 hours. 1N Hydrochloric acid (60 mL) was added to the resulting mixture, and the organic layer was separated and the aqueous layer was extracted with ethyl acetate (30 mL×2 times). The organic layer combined was washed with a saturated sodium chloride solution (100 mL) and dried over anhydrous magnesium sulfate. After removal of magnesium sulfate by filtration, the filtrate was evaporated to give a white solid of 2-(2-chloro-4-methyl-5-hydroxyphenyl)-5,6-dihydroimidazo [1,5-a] pyridine-1,3 [2H, 7H]-dione (1.74 g, yield:93.0%).

$^1$H-NMR(CDCl$_3$, TMS, ppm): δ1.70–2.20(m, 2H), 2.12 (s, 3H), 2.30–2.55(m, 2H), 3.76(t, J=5.04 Hz, 2H), 6.23(t, J=5.04 Hz, 1H), 6.86(s, 1H), 7.29(s, 1H).

EXAMPLE-21

Synthesis of 2-(2-chloro-4-methyl-5-methoxyphenyl)-5,6-dihydroimidazo [1,5-a] pyridine-1,3[2H, 7H]-dione

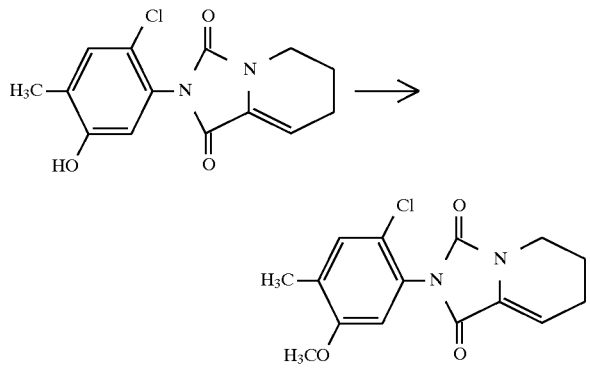

An acetonitrile (10 mL) solution of 2-(2-chloro-4-methyl-5-hydroxyphenyl)-5,6-dihydroimidazo [1,5-a] pyridine-1,3 [2H, 7H]-dione (0.34 g, 1.11 mmol), methyliodide (0.08 mL, 1.22 mmol) and potassium carbonate (0.15 g, 1.11 mmol) was stirred for 30 minutes under reflux. A saturated ammonium chloride solution (20 mL) was added to the resulting mixture and the organic layer was separated. The aqueous layer was extracted with diethyl ether (10 mL×2 times), and the organic layer combined was washed with a saturated sodium chloride solution (40 mL) and dried over anhydrous magnesium sulfate. After removal of magnesium sulfate by filtration, the filtrate was evaporated to give crude product, which was purified by silica gel column (Wakogel C-200, ethyl acetate/hexane=1/2) to obtain a white solid of 2-(2-chloro-4-methyl-5-methoxyphenyl)-5,6-dihydroimidazo [1,5-a] pyridine-1,3[2H, 7H]-dione (0.22 g, yield:61.1%).

$^1$H-NMR(CDCl$_3$, TMS, ppm): δ1.85–2.20(m, 2H), 2.14 (s, 3H), 2.30–2.55(m, 2H), 3.65–3.95(m, 5H), 6.25(t, J=5.04 Hz, 1H), 6.79(s, 1H), 7.38(s, 1H).

mp:180°–182° C.

EXAMPLE-22

Synthesis of 2-(5-allyloxy-2-chloro-4-methylphenyl)-5,6-dihydroimidazo [1,5-a] pyridine-1,3[2H, 7H]-dione

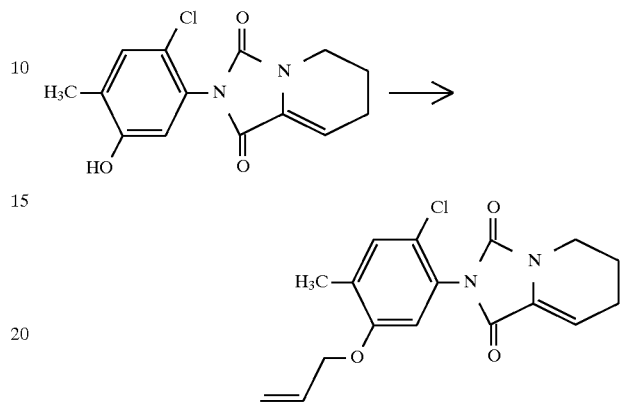

An acetonitrile (10 mL) solution of 2-(2-chloro-4-methyl-5-hydroxyphenyl)-5,6-dihydroimidazo [1,5-a] pyridine-1,3 [2H, 7H]-dione (0.34 g, 1.11 mmol), allylbromide (0.11 mL, 1.22 mmol) and potassium carbonate (0.15 g, 1.11 mmol) was stirred for one hour under reflux. A saturated ammonium chloride solution (20 mL) was added to the resulting mixture and the organic layer was separated. The aqueous layer was extracted with diethyl ether (10 mL×2 times), and the organic layer combined was washed with a saturated sodium chloride solution (40 mL) and dried over anhydrous magnesium sulfate. After removal of magnesium sulfate by filtration, the filtrate was evaporated to give crude product, which was purified by silica gel column (Wakogel C-200, ethyl acetate/hexane =1/2) to obtain a white solid of 2-(5-allyloxy-2-chloro-4-methylphenyl)-5,6-dihydroimidazo [1,5-a] pyridine-1,3[2H, 7H]-dione (0.24 g, yield:61.5%).

$^1$H-NMR(CDCl$_3$, TMS, ppm): δ1.90–2.20(m, 2H), 2.15 (s, 3H), 2.30–2.60(m, 2H), 3.79(t, J=5.04 Hz, 2H), 4.50–4.70(m, 2H), 5.25–5.61(m, 2H), 5.90–6.35(m, 2H), 6.79(s, 1H)7.37(s, 1H).

mp:105°–107° C.

EXAMPLE-23

Synthesis of 2-(2-chloro-4-methyl-5-propargyloxyphenyl)-5,6-dihydroimidazo [1,5-a] pyridine-1,3[2H, 7H]-dione

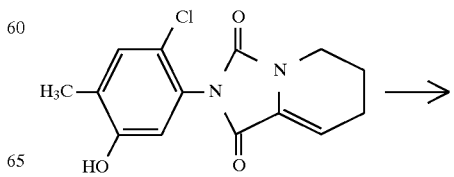

-continued

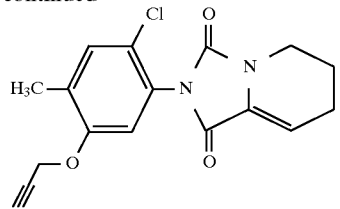

An acetonitrile (10 mL) solution of 2-(2-chloro-4-methyl-5-hydroxyphenyl)-5,6-dihydroimidazo [1,5-a] pyridine-1,3 [2H, 7H]-dione (0.34 g, 1.11 mmol), propargylbromide (0.11 mL, 1.22 mmol) and potassium carbonate (0.15 g, 1.11 mmol) was stirred for 30 minutes under reflux. A saturated ammonium chloride solution (20 mL) was added to the resulting mixture and the organic layer was separated. The aqueous layer was extracted with diethyl ether (10 mL×2 times), and the organic layer combined was washed with a saturated sodium chloride solution (40 mL) and dried over anhydrous magnesium sulfate. After removal of magnesium sulfate by filtration, the filtrate was evaporated to give crude product, which was purified by silica gel column (Wakogel C-200, ethyl acetate/hexane=1/4–1/2) to obtain a white solid of 2-(2-chloro-4-methyl-5-propargyloxyphenyl)-5,6-dihydroimidazo [1,5-a] pyridine-1,3[2H, 7H]-dione (0.24 g, yield:63.2%).

$^1$H-NMR(CDCl$_3$, TMS, ppm): δ1.80–2.22(m, 2H), 2.15 (s, 3H), 2.25–2.66(m, 3H), 3.78(t, J=5.04 Hz, 2H), 4.78(d, J=2.52 Hz, 2H), 6.24(t, J=5.04 Hz, 1H), 6.91(s, 1H), 7.35(s, 1H).

mp:177°–179° C.

EXAMPLE-24

Synthesis of 2-(2-chloro-4-methyl-5-methylpropargyloxyphenyl)-5,6-dihydroimidazo [1,5-a] pyridine-1,3[2H, 7H]-dione

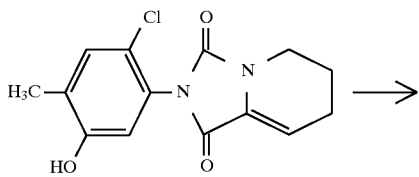

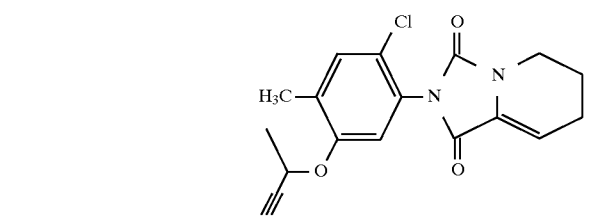

An acetonitrile (10 mL) solution of 2-(2-chloro-4-methyl-5-hydroxyphenyl)-5,6-dihydroimidazo [1,5-a] pyridine-1,3 [2H, 7H]-dione (0.34 g, 1.11 mmol), methyl-propargyl tosylate (0.27 g, 1.22 mmol) and potassium carbonate (0.15 g, 1.11 mmol) was stirred for 6.5 hours under reflux. A saturated ammonium chloride solution (20 mL) was added to the resulting mixture and the organic layer was separated. The aqueous layer was extracted with diethyl ether (10 mL×2 times), and the organic layer combined was washed with a saturated sodium chloride solution (40 mL) and dried over anhydrous magnesium sulfate. After removal of magnesium sulfate by filtration, the filtrate was evaporated to give crude product, which was purified by silica gel column (Wakogel C-200, ethyl acetate/hexane=1/2) to obtain a white solid of 2-(2-chloro-4-methyl-5-methylpropargyloxyphenyl)-5,6-dihydroimidazo [1,5-a] pyridine-1,3[2H, 7H]-dione (0.15 g, yield:37.5%).

$^1$H-NMR(CDCl$_3$, TMS, ppm): δ1.70(d, J=6.30, 3H), 1.90–2.25(m, 2H), 2.15(s, 3H), 2.30–2.60(m, 3H), 3.78(t, J=5.04 Hz, 2H), 4.87(dq, J=2.55 and 6.30 Hz, 1H), 6.22(t, J=5.04 Hz, 1H), 7.00(s, 1H), 7.35(s, 1H).

mp:120°–122° C.

EXAMPLE-25

Synthesis of 2-(2-chloro-5-cyclopentyloxy-4-methylphenyl)-5,6-dihydroimidazo [1,5-a] pyridine-1,3[2H, 7H]-dione

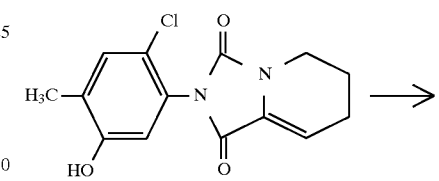

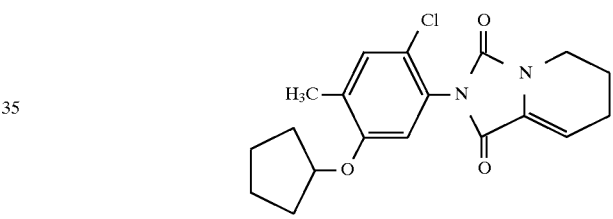

An acetonitrile (10 mL) solution of 2-(2-chloro-4-methyl-5-hydroxyphenyl)-5,6-dihydroimidazo [1,5-a] pyridine-1,3 [2H, 7H]-dione (0.34 g, 1.11 mmol), cyclopentylbromide (0.13 mL, 1.22 mmol) and potassium carbonate (0.15 g, 1.11 mmol) was stirred for 4 hours under reflux. A saturated ammonium chloride solution (20 mL) was added to the resulting mixture and the organic layer was separated. The aqueous layer was extracted with diethyl ether (10 mL×2 times), and the organic layer combined was washed with a saturated sodium chloride solution (40 mL) and dried over anhydrous magnesium sulfate. After removal of magnesium sulfate by filtration, the filtrate was evaporated to give crude product, which was purified by silica gel column (Wakogel C-200, ethyl acetate/hexane=1/2) to obtain a white solid of 2-(2-chloro-5-cyclopentyloxy-4-methylphenyl)-5,6-dihydroimidazo [1,5-a] pyridine-1,3[2H, 7H]-dione (0.27 g, yield:64.3%).

$^1$H-NMR(CDCl$_3$, TMS, ppm): δ1.50–2.20(m, 10H), 2.11 (s, 3H), 2.28–2.60(m, 2H), 3.77(t, J=6.30 Hz, 2H), 4.65–4.87(m, 1H), 6.22(t, J=5.04 Hz, 1H), 6.85(s, 1H), 7.32(s, 1H).

mp:105°–107° C.

EXAMPLE-26

Synthesis of 2-(2,4-dichloro-5-methoxycarbonyloxyphenyl)-5,6-dihydroimidazo [1,5-a] pyridine-1,3[2H, 7H]-dione

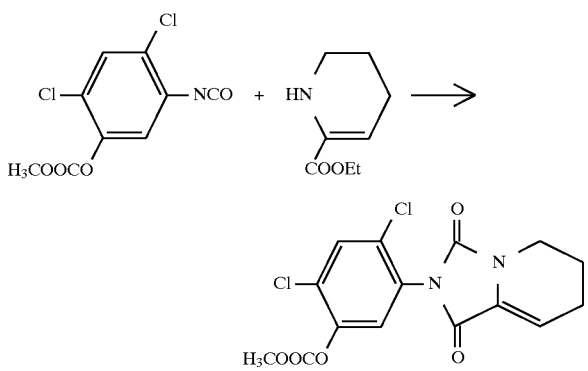

To a toluene (70 mL) solution of ethyl dehydropipecolate (2.33 g, 15 mmol) was dropwise added a toluene (30 mL) solution of 2,4-dichloro-5-methoxycarbonyloxyphenylisocyanate (3.90 g, 15 mmol) and triethylamine (1.05 mL, 7.5 mmol) under cooling in an ice-water bath. The mixture was stirred for 30 minutes at 0° C. and for 17 hours at room temperature, and further stirred for 5.5 hour at 80° C. A saturated ammonium chloride solution (100 mL) was added to the resulting mixture, and the organic layer was separated and then the aqueous layer was extracted with ethyl acetate (50 mL×2 times). The organic layer combined was washed with a saturated sodium chloride solution (200 mL) and dried over anhydrous magnesium sulfate. After removal of magnesium sulfate by filtration, the filtrate was evaporated to give crude product, which was purified by silica gel column (Wakogel C-200, ethyl acetate/hexane=1/2) to obtain a white solid of 2-(2,4-dichloro-5-methoxycarbonyloxyphenyl)-5,6-dihydroimidazo [1,5-a] pyridine-1,3[2H, 7H]-dione (3.45 g, yield:62.3%).

$^1$H-NMR(CDCl$_3$, TMS, ppm): δ1.90–2.15(m, 2H), 2.30–2.55(m, 2H), 3.75(t, J=5.04 Hz, 2H), 3.95(s, 3H), 6.25(t, J=5.04 Hz, 1H), 7.32(s, 1H), 7.69(s, 1H).

EXAMPLE-27

Synthesis of 2-(2,4-dichloro-5-hydroxyphenyl)-5,6-dihydroimidazo [1,5-a] pyridine-1,3[2H, 7H]-dione

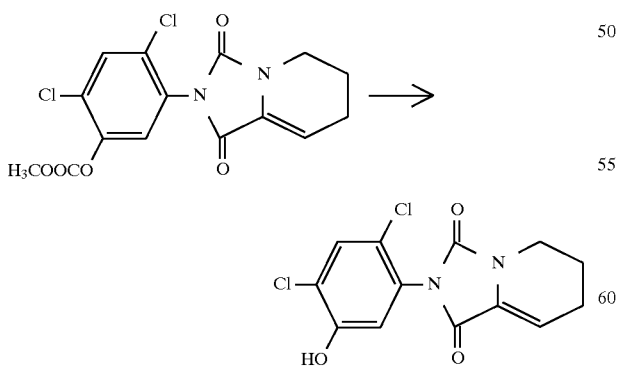

A methanol (10 mL) solution of 2-(2,4-dichloro-5-methoxycarbonyloxyphenyl)-5,6-dihydroimidazo [1,5-a] pyridine-1,3[2H, 7H]-dione (0.50 g, 1.35 mmol) and potassium carbonate (0.19 g, 1.35 mmol) was stirred at 50°–60° C. for 2 hours. 1N Hydrochloric acid (20 mL) was added to the resulting mixture, and the organic layer was separated and then the aqueous layer was extracted with ethyl acetate (10 mL×2 times). The organic layer combined was washed with a saturated sodium chloride solution (30 mL) and dried over anhydrous magnesium sulfate. After removal of magnesium sulfate by filtration, the filtrate was evaporated to give a white solid of 2-(2,4-dichloro-5-hydroxyphenyl)-5,6-dihydroimidazo [1,5-a] pyridine-1,3[2H, 7H]-dione (0.34 g, yield:81.0%).

$^1$H-NMR(CDCl$_3$, TMS, ppm): δ1.90–2.18(m, 2H), 2.30–2.57(m, 2H), 3.75(t, J=5.04 Hz, 2H), 6.29(t, J=5.04 Hz, 1H), 6.95(s, 1H), 7.50(s, 1H).

EXAMPLE-28

Synthesis of 2-(2,4-dichloro-5-methoxyphenyl)-5,6-dihydroimidazo [1,5-a] pyridine-1,3[2H, 7H]-dione

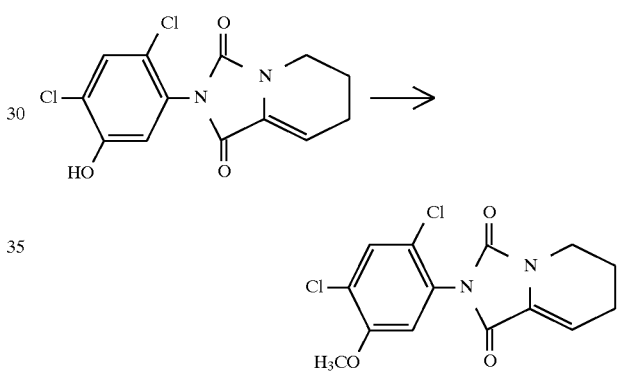

An acetonitrile (10 mL) solution of 2-(2,4-dichloro-5-hydroxyphenyl)-5,6-dihydroimidazo [1,5-a] pyridine-1,3 [2H, 7H]-dione (0.62 g, 2.0 mmol), methyliodide (0.25 mL, 4 mmol) and potassium carbonate (0.21 g, 1.5 mmol) was stirred for 2 hours under reflux. A saturated ammonium chloride solution (20 mL) was added to the resulting mixture and the organic layer was separated. The aqueous layer was extracted with diethyl ether (10 mL×2 times), and the organic layer combined was washed with a saturated sodium chloride solution (40 mL) and dried over anhydrous magnesium sulfate. After removal of magnesium sulfate by filtration, the filtrate was evaporated to give crude product, which was purified by crystallization from dichloromethane to obtain a white solid of 2-(2,4-dichloro-5-methyloxyphenyl)-5,6-dihydroimidazo [1,5-a] pyridine-1,3 [2H, 7H]-dione (0.65 g, yield:100%).

$^1$H-NMR(CDCl$_3$, TMS, ppm): δ1.87–2.19(m, 2H), 2.32–2.58(m, 2H), 3.79(t, J=6.30 Hz, 2H), 3.91(s, 3H), 6.27(t, J=5.04 Hz, 1H), 6.89(s, 1H), 7.58(s, 1H).

mp:180°–182° C.

EXAMPLE-29

Synthesis of 2-(5-allyloxy-2,4-dichlorophenyl)-5,6-dihydroimidazo [1,5-a] pyridine-1,3[2H, 7H]-dione

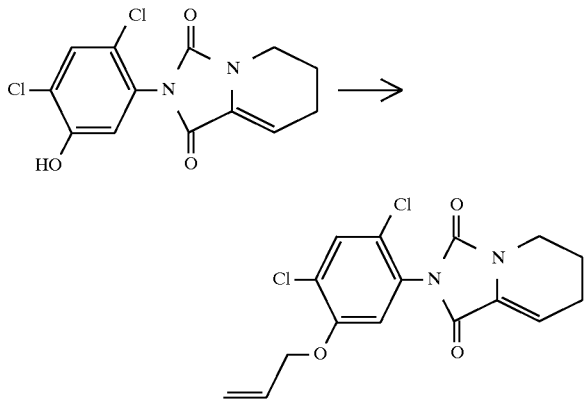

An acetonitrile (10 mL) solution of 2-(2,4-dichloro-5-hydroxyphenyl)-5,6-dihydroimidazo [1,5-a] pyridine-1,3 [2H, 7H]-dione (0.50 g, 1.61 mmol), allylbromide (0.15 mL, 1.77 mmol) and potassium carbonate (0.22 g, 1.61 mmol) was stirred for 2 hours under reflux. A saturated ammonium chloride solution (20 mL) was added to the resulting mixture and the organic layer was separated. The aqueous layer was extracted with diethyl ether (10 mL×2 times), and the organic layer combined was washed with a saturated sodium chloride solution (40 mL) and dried over anhydrous magnesium sulfate. After removal of magnesium sulfate by filtration, the filtrate was evaporated to give crude product, which was purified by silica gel column (Wakogel C-200, ethyl acetate/hexane =1/2) to obtain a white solid of 2-(5-allyloxy-2,4-dichlorophenyl)-5,6-dihydroimidazo [1,5-a] pyridine-1,3[2H, 7H]-dione (0.42 g, yield:73.7%).

$^1$H-NMR(CDCl$_3$, TMS, ppm): δ1.80–2.20(m, 2H), 2.30–2.55(m, 2H), 3.75(t, J=5.04 Hz, 2H), 4.60(d, J=5.04 Hz, 2H), 5.25–5.60(m, 2H), 5.87–6.15(m, 1H), 6.23(t, J=5.04 Hz, 1H), 6.86(s, 1H), 7.55(s, 1H).

mp:116°–118° C.

EXAMPLE-30

Synthesis of 2-(2,4-dichloro-5-propargyloxyphenyl)-5,6-dihydroimidazo [1,5-a] pyridine-1,3[2H, 7H]-dione

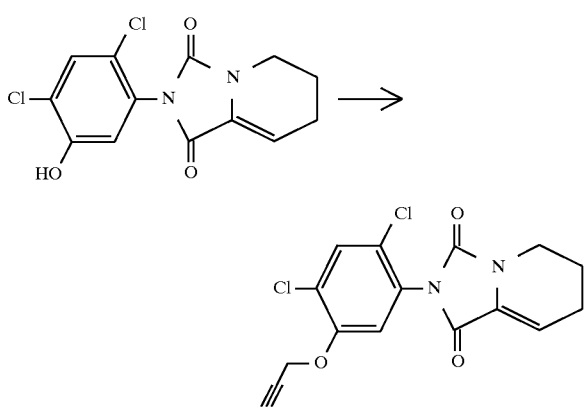

An acetonitrile (10 mL) solution of 2-(2,4-dichloro-5-hydroxyphenyl)-5,6-dihydroimidazo [1,5-a] pyridine-1,3 [2H, 7H]-dione (0.50 g, 1.61 mmol), propargylbromide (0.16 mL, 1.77 mmol) and potassium carbonate (0.22 g, 1.61 mmol) was stirred for 3 hours under reflux. A saturated ammonium chloride solution (20 mL) was added to the resulting mixture and the organic layer combined was washed with a saturated sodium chloride solution (40 mL) and dried over anhydrous magnesium sulfate. After removal of magnesium sulfate by filtration, the filtrate was evaporated to give crude product, which was purified by silica gel column (Wakogel C-200, ethyl acetate/hexane=1/2) to obtain a white solid of 2-(2,4-dichloro-5-propargyloxyphenyl)-5,6-dihydroimidazo [1,5-a] pyridine-1,3[2H, 7H]-dione (0.41 g, yield:73.2%).

$^1$H-NMR(CDCl$_3$, TMS, ppm): δ1.85–2.25(m, 2H), 2.30–2.60(m, 2H), 2.61(t, J=2.52 Hz, 1H), 3.79(t, J=6.30 Hz, 2H), 4.80(d, J=2.52 Hz, 2H), 6.26(t, J=5.04 Hz, 1H), 7.05(s, 1H), 7.59(s, 1H).

mp:172°–174° C.

EXAMPLE-31

Synthesis of 2-(2,4-dichloro-5-methylpropargyloxyphenyl)-5,6-dihydroimidazo [1,5-a] pyridine-1,3[2H, 7H]-dione

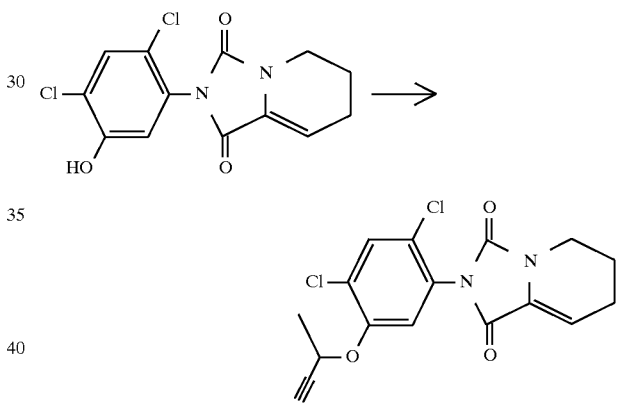

An acetonitrile (10 mL) solution of 2-(2,4-dichloro-5-hydroxyphenyl)-5,6-dihydroimidazo [1,5-a] pyridine-1,3 [2H, 7H]-dione (0.50 g, 1.61 mmol), methyl-propargyl tosylate (0.40 g, 1.77 mmol) and potassium carbonate (0.22 g, 1.61 mmol) was stirred for 5 hours under reflux. A saturated ammonium chloride solution (20 mL) was added to the resulting mixture and the organic layer was separated. The aqueous layer was extracted with diethyl ether (10 mL×2 times), and the organic layer combined was washed with a saturated sodium chloride solution (40 mL) and dried over anhydrous magnesium sulfate. After removal of magnesium sulfate by filtration, the filtrate was evaporated to give crude product, which was purified by silica gel column (Wakogel C-200, ethyl acetate/hexane=1/4–1/2) to obtain a white solid of 2-(2,4-dichloro-5-methylpropargyloxyphenyl)-5,6-dihydroimidazo [1,5-a] pyridine-1,3[2H, 7H]-dione (0.31 g, yield:52.5%).

$^1$H-NMR(CDCl$_3$, TMS, ppm): δ1.72(d, J=6.30, 3H), 1.85–2.18(m, 2H), 2.30–2.60(m, 2H), 2.58(d, J=2.52 Hz, 1H), 3.78(t, J=6.30 Hz, 2H), 4.97(dq, J=2.52 and 6.30 Hz, 1H), 6.25(t, J=5.04 Hz, 1H), 7.12(s, 1H), 7.58(s, 1H).

mp:127°–129° C.

EXAMPLE-32

Synthesis of 2-(5-cyclopentyloxy-2,4-dichlorophenyl)-5,6-dihydroimidazo [1,5-a] pyridine-1,3[2H, 7H]-dione

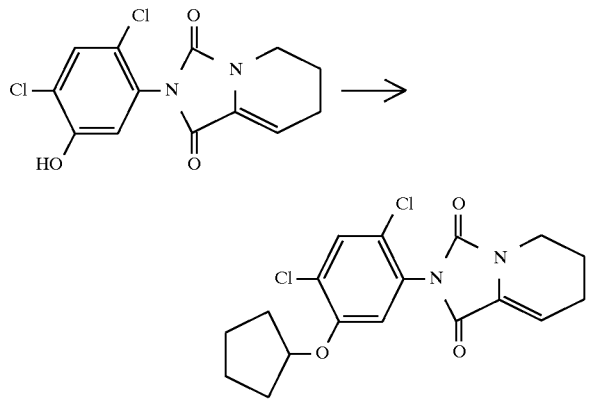

An acetonitrile (10 mL) solution of 2-(2,4-dichloro-5-hydroxyphenyl)-5,6-dihydroimidazo [1,5-a] pyridine-1,3 [2H, 7H]-dione (0.50 g, 1.61 mmol), cyclopentylbromide (0.19 mL, 1.77 mmol) and potassium carbonate (0.22 g, 1.61 mmol) was stirred for 2 hours under reflux. A saturated ammonium chloride solution (20 mL) was added to the resulting mixture and the organic layer was separated. The aqueous layer was extracted with diethyl ether (10 mL×2 times), and the organic layer combined was washed with a saturated sodium chloride solution (40 mL) and dried over anhydrous magnesium sulfate. After removal of magnesium sulfate by filtration, the filtrate was evaporated to give crude product, which was purified by silica gel column (Wakogel C-200, ethyl acetate/hexane=1/4–1/2) to obtain a white solid of 2-(5-cyclopentyloxy-2,4-dichlorophenyl)-5,6-dihydroimidazo [1,5-a] pyridine-1,3[2H, 7H]-dione (0.37 g, yield:60.7%).

$^1$H-NMR(CDCl$_3$, TMS, ppm): δ1.41–2.20(m, 10H), 2.30–2.67(m, 2H), 3.75(t, J=6.30 Hz, 1H), 4.68–4.90(m, 1H), 6.24(t, J=5.04 Hz, 1H), 6.85(s, 1H), 7.52(s, 1H).

mp:112°–114° C.

EXAMPLE-33

Synthesis of 2-(4-chloro-2-fluoro-5-methylthiophenyl)-5,6-dihydroimidazo [1,5-a] pyridine-1,3[2H, 7H]-dione

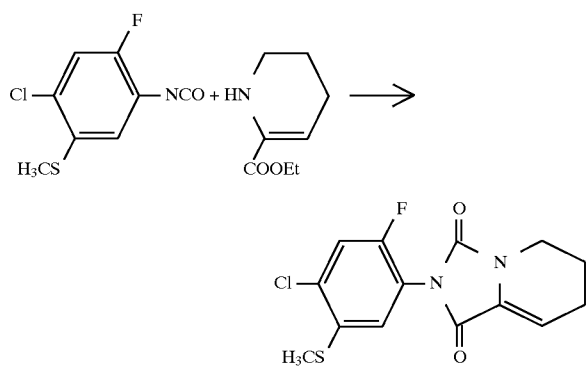

To a toluene (20 mL) solution of ethyl dehydropipecolate (666 mg, 4.29 mmol) was added a toluene (10 mL) solution of 4-chloro-2-fluoro-5-methylthiophenylisocyanate (934 mg, 4.29 mmol) and triethylamine (0.229 mL, 2.15 mmol) under cooling in an ice-water bath. The mixture was stirred for 0.5 hours at 0° C. and warmed up to room temperature, and further stirred for 3 hour at 80° C. 1N Hydrochloric acid (40 mL) was added to the resulting mixture which was extracted with ethyl acetate (20 mL×3 times). The organic layer combined was washed with a saturated sodium chloride solution (40 mL) and dried over anhydrous magnesium sulfate. After removal of magnesium sulfate by filtration, the filtrate was evaporated to give crude product, which was purified by silica gel column (Wakogel C-200, hexane/ethyl acetate=3/2) to obtain a white solid of 2-(4-chloro-2-fluoro-5-methylthiophenyl)-5,6-dihydroimidazo [1,5-a] pyridine-1, 3[2H, 7H]-dione (434 mg, yield:31.0%).

$^1$H-NMR(CDCl$_3$, TMS, ppm): δ1.85–2.20(m, 2H), 2.25–2.60(m, 5H), 3.74(t, J=5.71 Hz, 2H), 6.23(t, J=4.50 Hz, 1H), 7.10(d, J$_{HF}$=7.04 Hz, 1H), 7.29(d, J$_{HF}$=9.23 Hz, 1H).

mp:148°–149° C.

EXAMPLE-34

Synthesis of 2-(4-chloro-2-fluoro-5-isopropylthiophenyl)-5,6-dihydroimidazo [1,5-a] pyridine-1,3[2H, 7H]-dione

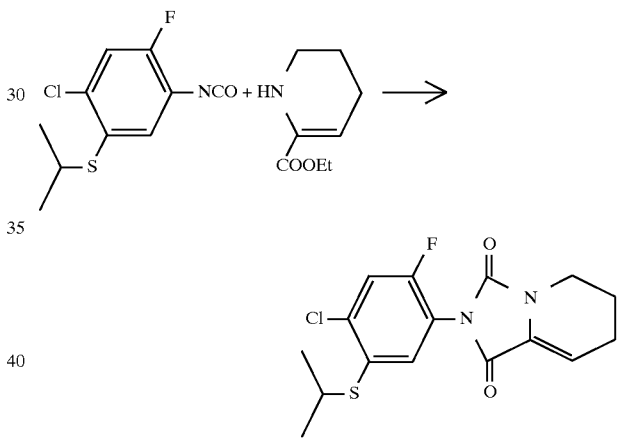

To a toluene (16 mL) solution of ethyl dehydropipecolate (528 mg, 3.40 mmol) was added a toluene (8 mL) solution of 4-chloro-2-fluoro-5-isopropylthiophenyl-isocyanate (835 mg, 3.40 mmol) and triethylamine (0.237 mL, 1.70 mmol) under cooling in an ice-water bath. The mixture was stirred for 0.5 hours at 0° C. and warmed up to room temperature, and further stirred for 4 hour at 80° C. 1N Hydrochloric acid (40 mL) was added to the resulting mixture which was extracted with ethyl acetate (20 mL×3 times). The organic layer combined was washed with a saturated sodium chloride solution (40 mL) and dried over anhydrous magnesium sulfate. After removal of magnesium sulfate by filtration, the filtrate was evaporated to give crude product, which was purified by silica gel column (Wakogel C-200, hexane/ethyl acetate=3/2) to obtain a white solid of 2-(4-chloro-2-fluoro-5-isopropylthio-phenyl)-5,6-dihydroimidazo [1,5-a] pyridine-1,3[2H, 7H]-dione (844 mg, yield:70.4%).

$^1$H-NMR(CDCl$_3$, TMS, ppm): δ1.45(d, J=6.59 Hz, 6H), 1.90–2.20(m, 2H), 2.30–2.60(m, 2H), 3.44(sep, J=6.59 Hz, 1H), 3.77(t, J=5.71 Hz, 2H), 6.25(t, J=4.50 Hz, 1H), 7.36(d, J$_{HF}$=8.75 Hz, 1H), 7.41(d, J$_{HF}$=7.25 Hz, 1H).

mp:126°–127° C.

EXAMPLE-35

Synthesis of 2-(5-allylthio-4-chloro-2-fluorophenyl)-5,6-dihydroimidazo [1,5-a] pyridine-1,3[2H, 7H]-dione

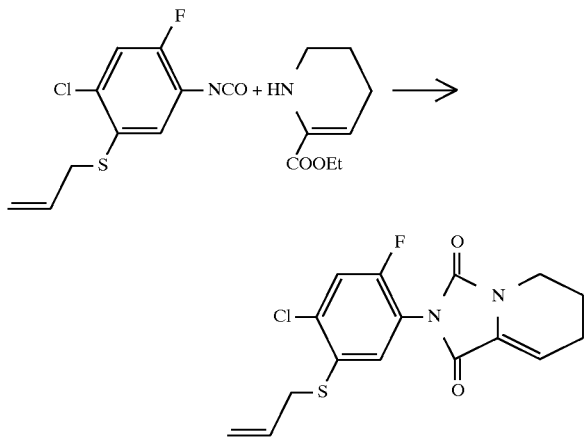

To a toluene (10 mL) solution of ethyl dehydropipecolate (0.52 g, 3.34 mmol) was dropwise added a toluene (5 mL) solution of 5-allylthio-4-chloro-2-fluorophenylisocyanate (0.74 g, 3.04 mmol) under cooling in an ice-water bath, and then triethylamine (0.21 mL, 1.52 mmol) was dropwise added under the same conditions. The mixture was stirred for 30 minutes at 0° C. and further stirred for 3 hour at room temperature. A saturated ammonium chloride solution (20 mL) was added to the resulting mixture and the organic layer was separated. The aqueous layer was extracted with diethyl ether (15 mL×2 times), and the organic layer combined was washed with a saturated sodium chloride solution (20 mL) and dried over anhydrous magnesium sulfate. After removal of magnesium sulfate by filtration, the filtrate was evaporated to give crude product, which was purified by silica gel column (Wakogel C-200, ethyl acetate/hexane =1/2) to obtain a white solid of 2-(5-allylthio-4-chloro-2-fluorophenyl)-5,6-dihydroimidazo [1,5-a] pyridine-1,3[2H, 7H]-dione(19a) (0.73 g, yield:70.9%).

$^1$H-NMR(CDCl$_3$, TMS, ppm): δ1.80–2.20(m, 2H), 2.30–2.60(m, 2H), 3.61(d, J=6.30 Hz, 2H), 3.79(t, J=6.30 Hz, 2H), 5.13(s, 1H), 5.30(d, J=7.56 Hz, 1H), 6.30(t, J=3.78 Hz, 1H), 7.25–7.40(m, 2H).

mp:98°–100° C.

EXAMPLE-36

Synthesis of 2-(4-chloro-2-fluoro-5-propargylthiophenyl)-5,6-dihydroimidazo [1,5-a] pyridine-1,3[2H, 7H]-dione

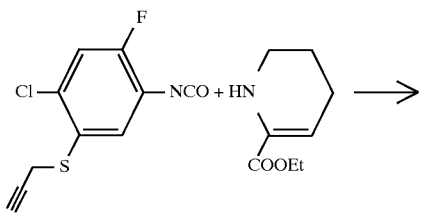

-continued

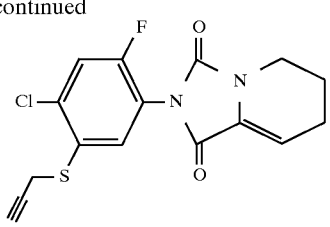

To a toluene (3 mL) solution of ethyl dehydropipecolate (0.17 g, 1.1 mmol) was dropwise added a toluene (2 mL) solution of 4-chloro-2-fluoro-5-propargylthiophenylisocyanate (0.27 g, 1.1 mmol) under cooling in an ice-water bath, and then triethylamine (0.08 mL, 0.55 mmol) was dropwise added under the same conditions. The mixture was stirred for 30 minutes at 0° C. and further stirred for 3 hour at room temperature. A saturated ammonium chloride solution (5 mL) was added to the resulting mixture and the organic layer was separated. The aqueous layer was extracted with diethyl ether (5 mL×2 times), and the organic layer combined was washed with a saturated sodium chloride solution (10 mL) and dried over anhydrous magnesium sulfate. After removal of magnesium sulfate by filtration, the filtrate was evaporated to give crude product, which was purified by silica gel column (Wakogel C-200, ethyl acetate/hexane=1/1) to obtain a white solid of 2-(4-chloro-2-fluoro-5-propargylthiophenyl)-5,6-dihydroimidazo [1,5-a] pyridine-1,3[2H, 7H]-dione (0.3 g, yield:81.0%).

$^1$H-NMR(CDCl$_3$, TMS, ppm): δ1.80–2.19(m, 2H), 2.29(t, J=2.52 Hz, 1H), 2.35–2.60(m, 2H), 3.64(d, J=2.52 Hz, 2H), 3.78(t, J=6.30 Hz, 2H), 6.25(t, J=5.04 Hz, 1H), 7.35(d, 1H, J$_{HF}$=7.56 Hz), 7.50(d, 1H, J$_{HF}$=8.82 Hz).

mp:163°–166° C.

EXAMPLE-37

Synthesis of 2-(4-chloro-2-fluoro-5-methylpropargylthiophenyl)-5,6-dihydroimidazo [1,5-a] pyridine-1,3[2H, 7H]-dione

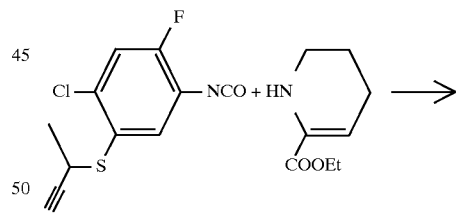

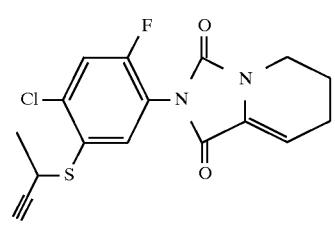

To a toluene (10 mL) solution of ethyl dehydropipecolate (291 mg, 1.87 mmol) was added a toluene (5 mL) solution of 4-chloro-2-fluoro-5-methylpropargylthiophenylisocyanate (479 mg, 1.87 mmol) and triethylamine (0.13 mL, 0.94 mmol) at 0° C. The mixture was stirred for 0.5 hours at 0° C. and further stirred for 3 hour at 80° C. 1N Hydrochloric acid (20 mL) was added to the resulting mixture which was extracted with ethyl acetate (10 mL×3 times). The organic layer combined was washed with a saturated sodium chloride solution (20 mL) and dried over anhydrous magnesium sulfate. After removal of magnesium sulfate by filtration, the filtrate was evaporated to give crude product, which was purified by silica gel column (Wakogel C-200, ethyl acetate/hexane=2/1) to obtain a white solid of 2-(4-chloro-2-fluoro-5-methylpropargylthiophenyl)-5,6-dihydroimidazo [1,5-a] pyridine-1,3[2H, 7H]-dione (421 mg, yield:61.7%).

$^1$H-NMR(CDCl$_3$, TMS, ppm): δ1.58(d, J=7.03 Hz, 3H), 1.85–2.20(m, 2H), 2.25–2.60(m, 3H), 3.77(t, J=5.25 Hz, 2H), 3.99(dq, J=2.42and7.03 Hz, 1H), 6.22(t, J=4.50 Hz, 1H), 7.35(d, J$_{HF}$=9.23 Hz, 1H), 7.59(d, J$_{HF}$=7.48 Hz, 1H).

EXAMPLE-38

Synthesis of 2-(4-chloro-2-fluoro-5-methoxycarbonylmethylthiophenyl)-5,6-dihydroimidazo [1,5-a] pyridine-1,3[2H, 7H]-dione

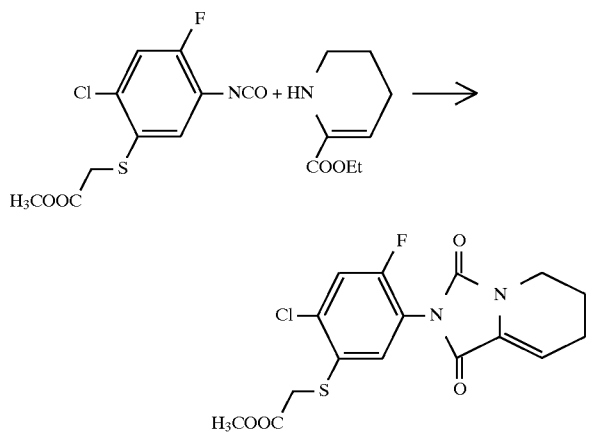

To a toluene (30 mL) solution of ethyl dehydropipecolate (940 mg, 6.06 mmol) was added a toluene (15 mL) solution of 4-chloro-2-fluoro-5-(methoxycarbonyl-methylthio) phenylisocyanate (1.67 g, 6.06 mmol) and triethylamine (0.422 mL, 3.03 mmol) at 0° C. The mixture was stirred for 0.5 hours at 0° C. and warmed up to room temperature, and further stirred for 3 hour at 80° C. 1N Hydrochloric acid (40 mL) was added to the resulting mixture which was extracted with ethyl acetate (20 mL×3 times). The organic layer combined was washed with a saturated sodium chloride solution (40 mL) and dried over anhydrous magnesium sulfate. After removal of magnesium sulfate by filtration, the filtrate was evaporated to give crude product, which was purified by silica gel column (Wakogel C-200, hexane/ethyl acetate=3/2) to obtain a white solid of 2-(4-chloro-2-fluoro-5-methoxycarbonyl-methylthiophenyl)-5,6-dihydroimidazo [1,5-a] pyridine-1,3[2H, 7H]-dione (1.34 g, yield:57.2%).

$^1$H-NMR(CDCl$_3$, TMS, ppm): δ1.85–2.20(m, 2H), 2.25–2.60(m, 2H), 3.68(s, 2H), 3.75(s, 3H), 3.78(t, J=5.25 Hz, 2H), 6.28(t, J=4.50 Hz, 1H), 7.38(d, J$_{HF}$=8.75 Hz, 1H), 7.52(d, J$_{HF}$=7.25 Hz, 1H).

mp:90°–91° C.

EXAMPLE-39

Synthesis of 2-(4-chloro-5-cyclopentylthio-2-fluorophenyl)-5,6-dihydroimidazo [1,5-a] pyridine-1,3 [2H, 7H]-dione

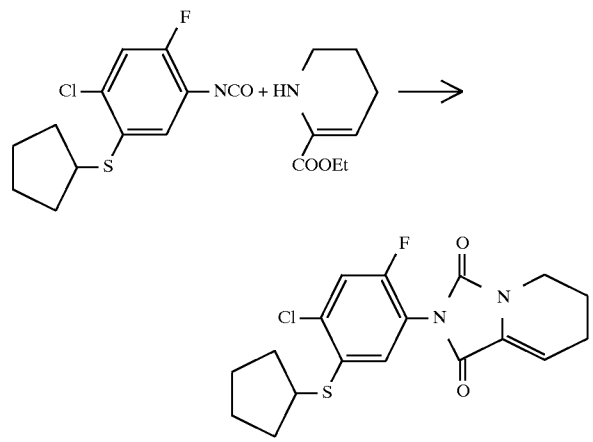

To a toluene (15 mL) solution of ethyl dehydropipecolate (0.69 g, 4.48 mmol) was dropwise added a toluene (8 mL) solution of 4-chloro-5-cyclopentylthio-2-fluorophenylisocyanate (18c) (1.10 g, 4.48 mmol) under cooling in an ice-water bath, and then triethylamine (0.31 mL, 2.24 mmol) was dropwise added under the same conditions. The mixture was stirred for 30 minutes at 0° C. and for 3 hours at room temperature, and further stirred for 7 hours at 80° C. A saturated ammonium chloride solution (20 mL) was added to the resulting mixture and the organic layer was separated. The aqueous layer was extracted with diethyl ether (15 mL×2 times). The organic layer combined was washed with a saturated sodium chloride solution (20 mL) and dried over anhydrous magnesium sulfate. After removal of magnesium sulfate by filtration, the filtrate was evaporated to give crude product, which was purified by silica gel column (Wakogel C-200, ethyl acetate/hexane=1/2) to obtain a white solid of 2-(4-chloro-5-cyclopentylthio-2-fluorophenyl)-5,6-dihydroimidazo [1,5-a] pyridine-1,3 [2H, 7H]-dione (0.63 g, yield:36.8%).

$^1$H-NMR(CDCl$_3$, TMS, ppm): δ1.40–1.90(m, 8H), 1.90–2.28(m, 2H), 2.30–2.58(m, 2H), 3.40–3.90(m, 3H), 6.25(t, J=5.04 Hz, 1H), 7.20–7.45(m, 2H).

mp:118°–121° C.

EXAMPLE 40

Synthesis of 2-{4-chloro-2-fluoro-5-(p-toluenesulfonyl-amino) phenyl} -5,6-dihydroimidazo [1,5-a] pyridine-1,3[2H, 7H]-dione

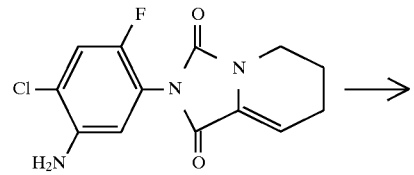

-continued

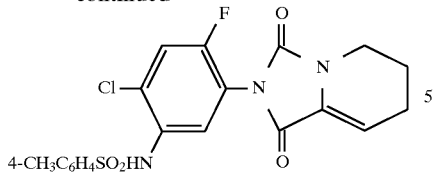

To a pyridine (5 mL) solution of 2-(5-amino-4-chloro-2-fluorophenyl)-5,6-dihydroimidazo [1,5-a] pyridine-1, 3[2H, 7H]-dione (0.35 g, 1.2 mmol) was dropwise added p-toluenesulfonyl chloride (0.25 g, 1.3 mmol) under cooling in an ice-water bath, and the mixture was stirred for 2.5 hours at the ambient temperature. 1N Hydrochloric acid (60 mL) and ethyl acetate (40 mL) were added to the resulting mixture and the organic layer was separated. The aqueous layer was extracted with ethyl acetate (20 mL×2 times), and the organic layer combined was washed with a saturated sodium chloride solution (100 mL) and dried over anhydrous magnesium sulfate. After removal of magnesium sulfate by filtration, the filtrate was evaporated to give crude product, which was purified by silica gel column (Wakogel C-200, ethyl acetate/hexane =1/2) to obtain a white solid of 2-[4-chloro-2-fluoro-5-(p-toluenesulfonylamino)phenyl]-5,6-dihydroimidazo [1,5-a] pyridine-1,3[2H, 7H]-dione (0.32 g, yield:59.3%).

$^1$H-NMR(CDCl$_3$, TMS, ppm): δ1.85–2.20(m, 2H), 2.28–2.60(m, 5H), 3.80(t, J=6.30 Hz, 2H), 6.38(t, 1H, J=5.04 Hz), 6.92(brs, 1H), 7.10–7.38(m, 3H), 7.60–7.91(m, 3H).

mp:225°–227° C.

EXAMPLE-41

Synthesis of 2-(4-chloro-2-fluoro-5-methoxycarbonylmethylthiophenyl)-5,6-dihydroimidazo [1,5-a] pyridine-1-oxo-3[2H, 7H]-thione

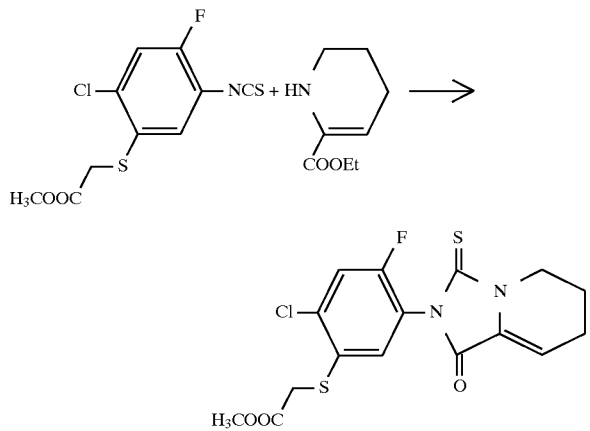

To a toluene (18 mL) solution of 4-chloro-2-fluoro-5-(methoxycarbonylmethylthio)phenylisothiocyanate (1.03 g, 3.52 mmol) and triethylamine (0.245 mL, 1.76 mmol) was dropwise added a toluene (7 mL) solution of ethyl dehydropipecolate (546 mg, 3.52 mmol) under cooling in an ice-water bath. The mixture was stirred for 30 minutes at 0° C. and for 2 hour at room temperature, and further stirred for 2 hours at 80° C. A saturated ammonium chloride solution (20 mL) was added to the resulting mixture and the organic layer was separated. The aqueous layer was extracted with ethyl acetate (20 mL×2 times). The organic layer combined was washed with a saturated sodium chloride solution and dried over anhydrous magnesium sulfate. After removal of magnesium sulfate by filtration, the filtrate was evaporated to give crude product, which was purified by silica gel column (Wakogel C-200, ethyl acetate/hexane=1/2) to obtain 2-(4-chloro-2-fluoro-5-methoxycarbonylmethylthiophenyl)-5,6-dihydroimidazo [1,5-a] pyridine-1-oxo-3[2H, 7H]-thione (763 mg, yield:54.1%).

$^1$H-NMR(CDCl$_3$, TMS, ppm): δ1.95–2.25(m, 2H), 2.25–2.60(m, 2H), 3.67(s, 2H), 3.73(s, 3H), 3.95–4.15(m, 2H), 6.37(t, J=4.5 Hz, 1H), 7.39(d, J$_{HF}$=9.0 Hz, 1H), 7.51(d, J$_{HF}$=7.5 Hz, 1H).

EXAMPLE-42

Synthesis of 2-(4-chloro-2-fluoro-5-methylpropargyloxyphenyl)-5,6-dihydroimidazo [1,5-a] pyridine-1-oxo-3[2H, 7H]-thione

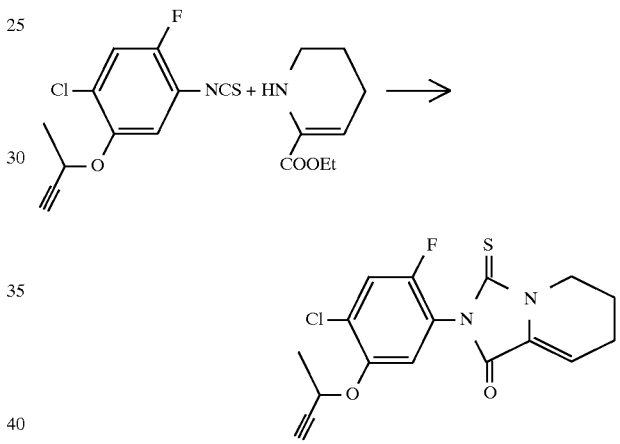

To a toluene (15 mL) solution of ethyl dehydropipecolate (0.37 g, 2.36 mmol) was added a toluene (5 mL) solution of 4-chloro-2-fluoro-5-methylpropargyloxyphenyl-isocyanate (0.60 g, 2.36 mmol) and triethylamine (0.16 mL, 1.18 mmol) at 0° C. The mixture was stirred for 0.5 hours at 0° C. and warmed up to room temperature, and further stirred for 14.5 hour at 80° C A saturated ammonium chloride solution (20 mL) was added to the resulting mixture and the organic layer was separated. The aqueous layer was extracted with ethyl acetate (15 mL×2 times). The organic layer combined was washed with a saturated sodium chloride solution (20 mL) and dried over anhydrous magnesium sulfate. After removal of magnesium sulfate by filtration, the filtrate was evaporated to give crude product, which was purified by silica gel column (Wakogel C-200, hexane/ethyl acetate=2/1) to obtain a white solid of 2-(4-chloro-2-fluoro-5-methylpropargyloxyphenyl)-5,6-dihydroimidazo [1,5-a] pyridine-1-oxo-3[2H, 7H]-thione (200 mg, yield:23.3%).

$^1$H-NMR(CDCl$_3$, TMS, ppm): δ1.71(d, J=6.3 Hz, 3H), 2.00–2.25(m, 2H), 2.35–2.60(m, 3H), 4.05(t, J=6.0 Hz, 2H), 4.70–5.05(m, 1H), 6.35(t, J=5.04 Hz, 1H), 7.17(d, J$_{HF}$=6.3 Hz, 1H), 7.33(d, J$_{HF}$=8.8 Hz, 1H).

mp:80°–90° C.

EXAMPLE-43

Synthesis of 2-(4-ethoxycarbonylmethoxy-2-fluoro-5-nitrophenyl)-5,6-dihydroimidazo [1,5-a] pyridine-1,3[2H, 7H]-dione

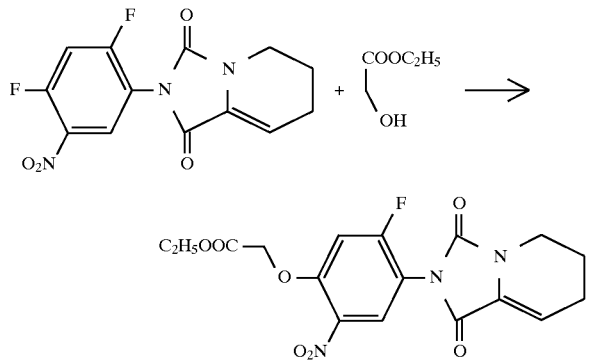

Sodium hydride (0.06 g, 2.4 mmol) was put in to a flask, to which 1,4-dioxane (5 mL) and ethyl glycolate (0.12 mL, 1.32 mmol) was added with stirring under cooling in an ice-water bath after replacing the inside of flask throughly with argon gas, and the mixture was stirred for 15 minutes at the ambient temperature. Then, 2-(2,4-difluoro-5-nitrophenyl)-5,6-dihydroimidazo [1,5-a] pyridine-1,3[2H, 7H]-dione (0.37 g, 1. mmol) was added to the mixture at the same temperature. The reaction mixture was wormed up to room temperature and stirred for 3 hours, and further stirred for 13 hours at 80° C. 1N Hydrochloric acid (10 mL) and ethyl acetate (10 mL) were added to the resulting mixture and the organic layer was separated. The aqueous layer was extracted with ethyl acetate (10 mL ×2 times). The organic layer combined was washed with a saturated sodium bicarbonate (20 mL) and a saturated sodium chloride solution (20 mL), and dried over anhydrous magnesium sulfate. After removal of magnesium sulfate by filtration, the filtrate was evaporated to give crude product, which was purified by silica gel column (Wakogel C-200, ethyl acetate/hexane=1/2) to obtain a white solid of 2-(4-ethoxycarbonylmethoxy-2-fluoro-5-nitrophenyl)-5,6-dihydroimidazo [1,5-a] pyridine-1,3[2H, 7H]-dione (0.23 g, yield:48.9%).

$^1$H-NMR(CDCl$_3$, TMS, ppm): δ1.30(t, J=6.30 Hz, 3H), 1.90–2.17(m, 2H), 2.30–2.55(m, 2H), 3.75(t, J=6.30 Hz, 2H), 4.30(q, J=6.30 Hz, 2H), 4.90(s, 2H), 6.26(t, J=5.04 Hz, 1H), 6.87(d, J$_{HF}$=6.30 Hz, 1H), 8.03(d, J$_{HF}$=7.56 Hz, 1H).

mp:171°–174° C.

EXAMPLE-44

Synthesis of 2-(7-fluoro-2H-3(4H)-oxo-1,4-benzoxazine-6-yl)-5,6-dihydroimidazo [1,5-a] pyridine-1,3[2H, 7H]-dione

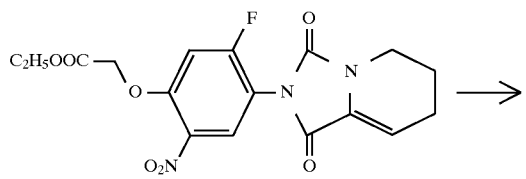

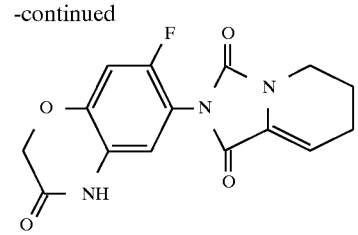

An acetic acid (194 mL) solution of reduced iron (24.4 g) was refluxed for one hour, to which an ethyl acetate (127 mL) solution of 2-(4-ethoxycarbonylmethoxy-2-fluoro-5-nitrophenyl)-5,6-dihydroimidazo [1,5-a] pyridine-1,3[2H, 7H]-dione (7.18 g, 0.02 mol) was dropwise added. The reaction mixture was stirred under reflux for 2 hours. After the reaction was completed, an insoluble solid deposited was separated by filtration and the filtrate was washed with 1N hydrochloric acid (250 mL) and then water (300 mL), and dried over anhydrous magnesium sulfate. After removal of magnesium sulfate by filtration, the filtrate was evaporated to give crude product, which was purified by crystallization from dichloromethane to obtain a white solid of 2-(7-fluoro-2H-3(4H)-oxo-1,4-benzoxazine-6-yl)-5,6-dihydroimidazo [1,5-a] pyridine-1,3[2H, 7H]-dione (2.20 g, yield:38.4%).

$^1$H-NMR(CDCl$_3$, TMS, ppm): δ1.80–2.18(m, 2H), 2.30–2.56(m, 2H), 3.76(t, J=6.30 Hz, 2H), 4.63(s, 2H), 6.25(t, J=5.04 Hz, 1H), 6.80(d, J$_{HF}$=6.30 Hz, 1H), 6.90(d, J$_{HF}$=8.82 Hz, 1H), 9.15(bs, 1H).

mp:214°–216° C.

EXAMPLE-45

Synthesis of 2-(4-allyl-7-fluoro-2H-3(4H)-oxo-1,4-benzoxazine-6-yl)-5,6-dihydroimidazo [1,5-a] pyridine- 1,3[2H, 7H]-dione

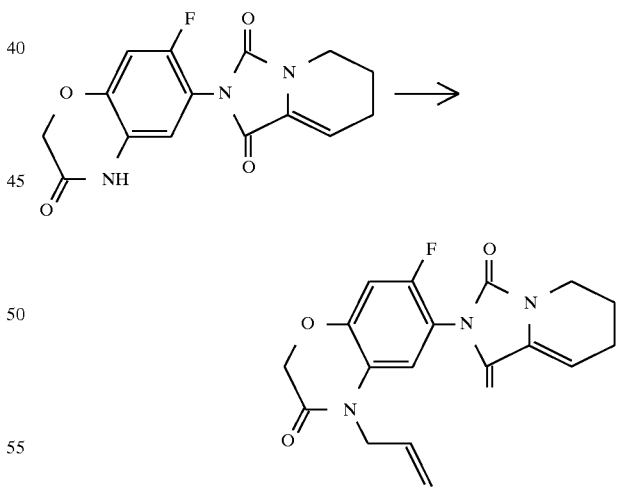

To an N,N-dimethylformamide (10 mL) solution of 2-(7-fluoro-2H-3(4H)-oxo-1,4-benzoxazine-6-yl)-5,6-dihydroimidazo [1,5-a] pyridine-1,3[2H, 7H]-dione (0.32 g, 1.0 mmol) and potassium carbonate (0.14 g, 1.0 mmol) was dropwise added allylbromide (0.1 mL, 1.1 mmol) at room temperature, and the mixture was stirred at the ambient temperature over night. 1N Hydrochloric acid (10 mL) and ethyl acetate (10 mL) were added to the resulting mixture and the organic layer was separated. The aqueous layer was

47 extracted with ethyl acetate (10 mL×2 times). The organic layer combined was washed with a saturated sodium chloride solution (10 mL) and dried over anhydrous magnesium sulfate. After removal of magnesium sulfate by filtration, the filtrate was evaporated to give crude product, which was purified by silica gel column (Wakogel C-200, ethyl acetate/hexane=1/1) to obtain a white solid of 2-(4-allyl-7-fluoro-2H-3(4H)-oxo-1,4-benzoxazine-6-yl)-5,6-dihydroimidazo [1,5-a] pyridine-1,3[2H, 7H]-dione (0.16 g, yield:45.1%).

$^1$H-NMR(CDCl$_3$, TMS, ppm): δ1.80–2.18(m, 2H), 2.31–2.60(m, 2H), 3.76(t, J=5.04 Hz, 2H), 4.45–4.65(m, 2H), 4.70(s, 2H), 5.10–5.40(m, 2H), 5.65–6.05(m, 1H), 6.23(t, J=3.78 Hz, 1H), 6.88(d, J$_{HF}$=7.65 Hz, 1H), 6.90(d, J$_{HF}$=10.1 Hz, 1H).

mp:194°–196° C.

EXAMPLE-46

Synthesis of 2-(7-fluoro-4-methyl-2H-3(4H)-oxo-1,4-benzoxazine-6-yl)-5,6-dihydroimidazo [1,5-a] pyridine-1,3[2H, 7H]-dione

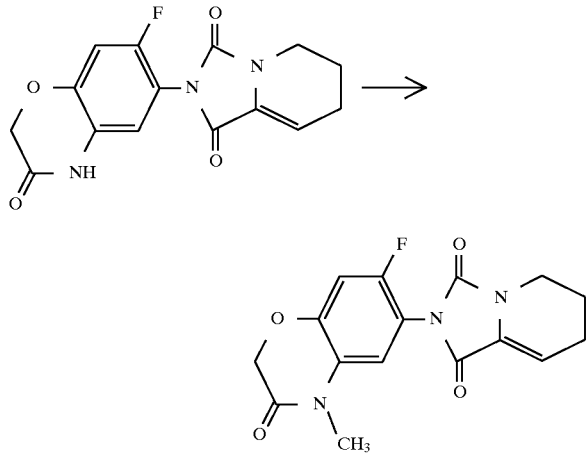

To an N,N-dimethylformamide (10 mL) solution of 2-(7-fluoro-2H-3(4H)-oxo-1,4-benzoxazine-6-yl)-5,6-dihydroimidazo [1,5-a] pyridine-1,3[2H, 7H]-dione (0.32 g, 1.0 mmol) and potassium carbonate (0.14 g, 1.0 mmol) was dropwise added methyliodide (0.07 mL, 1.1 mmol) at room temperature, and the mixture was stirred for 24 hours at the ambient temperature. 1N Hydrochloric acid (10 mL) and ethyl acetate (10 mL) were added to the resulting mixture and the organic layer was separated. The aqueous layer was extracted with ethyl acetate (10 mL×2 times). The organic layer combined was washed with a saturated sodium chloride solution (10 mL) and dried over anhydrous magnesium sulfate. After removal of magnesium sulfate by filtration, the filtrate was evaporated to give crude product, which was purified by silica gel column (Wakogel C-200, ethyl acetate/hexane=1/1) to obtain a white solid of 2-(7-fluoro-4-methyl-2H-3(4H)-oxo-1,4-benzoxazine-6-yl)-5,6-dihydroimidazo [1,5-a] pyridine-1,3[2H, 7H]-dione (0.12 g, yield:36.5%).

$^1$H-NMR(CDCl$_3$, TMS, ppm): δ1.80–2.15(m, 2H), 2.28–2.55(m, 2H), 3.32(s, 3H), 3.75(t, J=6.30 Hz, 2H), 4.66(s, 2H), 6.24(t, J=5.04 Hz, 1H), 6.88(d, J$_{HF}$=7.56 Hz, 1H), 6.90(d, J$_{HF}$=10.1 Hz, 1H).

mp:263°–266° C.

48

EXAMPLE-47

Synthesis 2-(7-fluoro-4-propargyl-2H-3(4H)-oxo-1,4-benzoxazine-6-yl)-5,6-dihydroimidazo [1,5-a] pyridine-1,3[2H, 7H]-dione

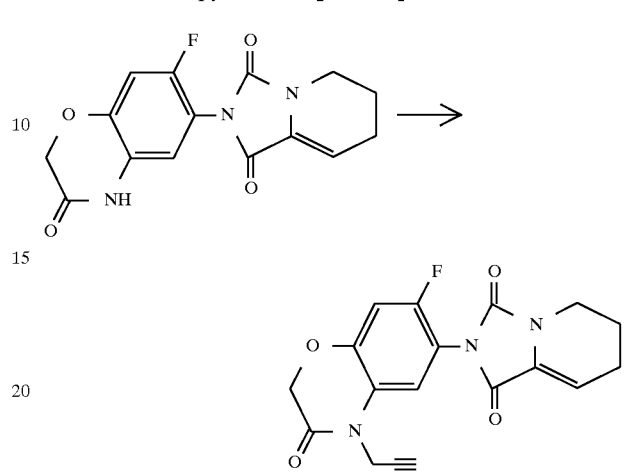

To an N,N-dimethylformamide (10 mL) solution of 2-(7-fluoro-2H-3(4H)-oxo-1,4-benzoxazine-6-yl)-5,6-dihydroimidazo [1,5-a] pyridine-1,3[2H, 7H]-dione (0.31 g, 0.98 mmol) and potassium carbonate (0.14 g, 0.98 mmol) was dropwise added propargylbromide (0.1 mL, 1.08 mmol) at room temperature, and the mixture was stirred for 24 hours at the ambient temperature. 1N Hydrochloric acid (10 mL) and ethyl acetate (10 mL) were added to the resulting mixture and the organic layer was separated. The aqueous layer was extracted with ethyl acetate (10 mL×2 times). The organic layer combined was washed with a saturated sodium chloride solution (10 mL) and dried over anhydrous magnesium sulfate. After removal of magnesium sulfate by filtration, the filtrate was evaporated to give crude product, which was purified by silica gel column (Wakogel C-200, ethyl acetate/hexane=1/1) to obtain a white solid of 2-(7-fluoro-4-propargyl-2H-3(4H)-oxo-1,4-benzoxazine-6-yl)-5,6-dihydroimidazo [1,5-a] pyridine-1,3[2H, 7H]-dione (0.29 g, yield:87.9%).

$^1$H-NMR(CDCl$_3$, TMS, ppm): δ1.90–2.20(m, 2H), 2.24–2.55(m, 3H), 3.79(t, J=6.30 Hz, 2H), 4.61–4.79(m, 4H), 6.26(t, J=5.04 Hz, 1H), 6.93(d, J$_{HF}$=10.1 Hz, 1H), 7.15(d, J$_{HF}$=8.82 Hz, 1H).

mp:232°–235° C.

EXAMPLE-48

Synthesis 2-(4-ethoxycarbonylmethylthio-2-fluoro-5-nitrophenyl)-5,6-dihydroimidazo [1,5-a] pyridine-1,3[2H, 7H]-dione

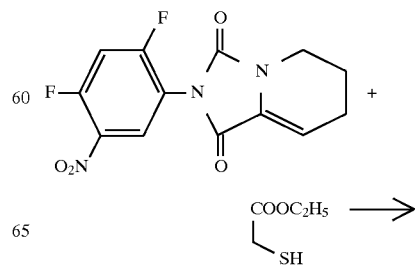

-continued

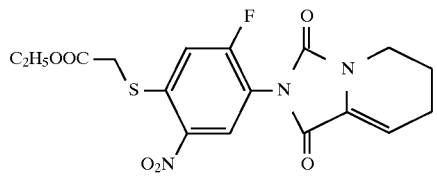

Sodium hydride (1.20 g, 0.03 mol) was put in to a flask, to which 1,4-dioxane (100 mL) and ethyl thioglycolate (1.83 mL, 0.017 mol) was added with stirring under cooling in an ice-water bath after replacing the inside of flask throughly with argon gas, and the mixture was stirred for 15 minutes at the ambient temperature. Then, 2-(2,4-difluoro-5-nitrophenyl)-5,6-dihydroimidazo [1,5-a] pyridine-1,3[2H, 7H]-dione (4.7 g, 0.015 mol) was added to the mixture at the same temperature. The reaction mixture was wormed up to room temperature and stirred for 24 hours. 1N Hydrochloric acid (100 mL) and ethyl acetate (100 mL) were added to the resulting mixture and the organic layer was separated. The aqueous layer was extracted with ethyl acetate (50 mL×2 times). The organic layer combined was washed with a saturated sodium bicarbonate (100 mL) and a saturated sodium chloride solution (100 mL), and dried over anhydrous magnesium sulfate. After removal of magnesium sulfate by filtration, the filtrate was evaporated to give crude product, which was purified by silica gel column (Wakogel C-200, ethyl acetate/hexane=1/1) to obtain a white solid of 2-(4-ethoxycarbonylmethylthio-2-fluoro-5-nitrophenyl)-5,6-dihydroimidazo [1,5-a] pyridine-1,3[2H, 7H]-dione (1.83 g, yield:29.8%).

$^1$H-NMR(CDCl$_3$, TMS, ppm): δ1.30(t, J=7.56 Hz, 3H), 1.90–2.20(m, 2H), 2.35–2.60(m, 2H), 3.68–3.90(m, 4H), 4.28(q, J=7.56 Hz, 2H), 6.30(t, J=5.04 Hz, 1H), 7.45(d, J$_{HF}$=10.1 Hz, 1H), 8.35(d, J$_{HF}$=6.30 Hz, 1H).

EXAMPLE-49

Synthesis of 2-(7-fluoro-2H-3(4H)-oxo-1,4-benzthioxazine-6-yl)-5,6-dihydroimidazo [1,5-a] pyridine-1,3[2H, 7H]-dione

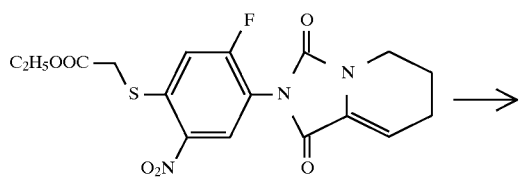

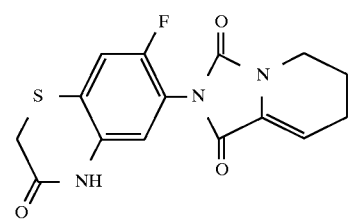

An acetic acid (90 mL) solution of reduced iron (11.25 g) was refluxed for one hour, to which an ethyl acetate (59 mL) solution of 2-(4-ethoxycarbonylmethylthio-2-fluoro-5-nitrophenyl)-5,6-dihydroimidazo [1,5-a] pyridine-1,3[2H, 7H]-dione (3.39 g, 8.3 mol) was dropwise added. The reaction mixture was stirred under reflux for 2 hours. After the reaction was completed, an insoluble solid deposited was separated by filtration and the filtrate was washed with 1N hydrochloric acid (100 mL) and then water (100 mL×3 times), and dried over anhydrous magnesium sulfate. After removal of magnesium sulfate by filtration, the filtrate was evaporated to give crude product, which was purified by crystallization from a mixed solution of dichloromethane and hexane to obtain a white solid of 2-(7-fluoro-2H-3(4H)-oxo-1,4-benzthioxazine-6-yl)-5,6-dihydroimidazo [1,5-a] pyridine-1,3[2H, 7H]-dione (1.29 g, yield:46.9%).

$^1$H-NMR(CDCl$_3$, TMS, ppm): δ1.70–2.19(m, 2H), 2.30–2.69(m, 2H), 3.39(s, 2H), 3.74(t, J=6.30 Hz, 2H), 6.22(t, J=5.04 Hz, 1H), 6.91(d, J$_{HF}$=6.30 Hz, 1H), 7.19(d, J$_{HF}$=8.82 Hz, 1H), 9.62(bs, 1H).

mp:248°–251° C.

EXAMPLE-50

Synthesis of 2-(4-allyl-7-fluoro-2H-3(4H)-oxo-1,4-benzthioxazine-6-yl)-5,6-dihydroimidazo [1,5-a] pyridine-1,3[2H, 7H]-dione

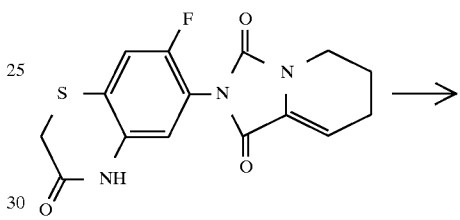

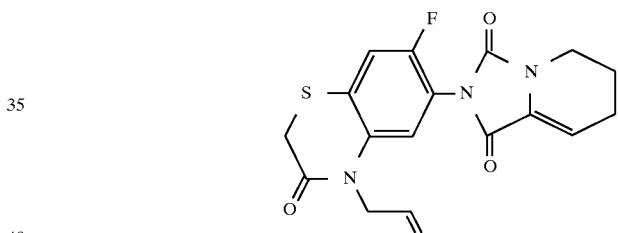

To an N,N-dimethylformamide (10 mL) solution of 2-(7-fluoro-2H-3(4H)-oxo-1,4-benzthioxazine-6-yl)-5,6-dihydroimidazo [1,5-a] pyridine-1,3[2H, 7H]-dione (0.33 g, 1.0 mmol) and potassium carbonate (0.14 g, 1.0 mmol) was dropwise added allylbromide (0.1 mL, 1.1 mmol) at room temperature, and the mixture was stirred at the ambient temperature for 16 hours. 1N Hydrochloric acid (10 mL) and ethyl acetate (10 mL) were added to the resulting mixture and the organic layer was separated. The aqueous layer was extracted with ethyl acetate (10 mL×2 times). The organic layer combined was washed with a saturated sodium chloride solution (10 mL) and dried over anhydrous magnesium sulfate. After removal of magnesium sulfate by filtration, the filtrate was evaporated to give crude product, which was purified by silica gel column (Wakogel C-200, ethyl acetate/hexane=1/1) to obtain a white solid of 2-(4-allyl-7-fluoro-2H-3(4H)-oxo-1,4-benzthioxazine-6-yl)-5,6-dihydroimidazo [1,5-a] pyridine-1,3[2H, 7H]-dione (0.1 g, yield:27.1%).

$^1$H-NMR(CDCl$_3$, TMS, ppm): δ1.81–2.11(m, 2H), 2.30–2.60(m, 2H), 3.49(s, 2H), 3.78(t, J=6.30 Hz, 2H), 4.50–4.70(m, 2H), 5.00–5.38(m, 2H), 5.70–6.02(m, 1H), 6.25(t, J=5.04 Hz, 1H), 7.09(d, J$_{HF}$=6.30 Hz, 1H), 7.28(d, J$_{HF}$=8.82 Hz, 1H).

mp:205°–208° C.

EXAMPLE-51

Synthesis of 2-(7-fluoro-4-methyl-2H-3(4H)-oxo-1,4-benzthioxazine-6-yl)-5,6-dihydroimidazo [1,5-a] pyridine-1,3[2H, 7H]-dione

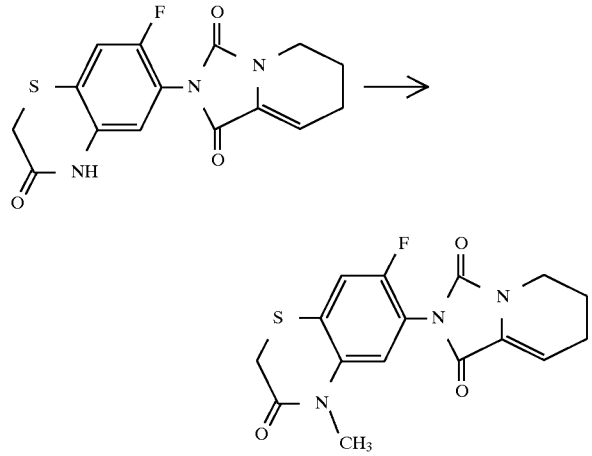

To an N,N-dimethylformamide (10 mL) solution of 2-(7-fluoro-2H-3(4H)-oxo-1,4-benzthioxazine-6-yl)-5,6-dihydroimidazo [1,5-a] pyridine-1,3[2H, 7H]-dione (0.33 g, 1.0 mmol) and potassium carbonate (0.14 g, 1.0 mmol) was dropwise added methyliodide (0.07 mL, 1.1 mmol) at room temperature, and the mixture was stirred for 18 hours at the ambient temperature. 1N Hydrochloric acid (10 mL) and ethyl acetate (10 mL) were added to the resulting mixture and the organic layer was separated. The aqueous layer was extracted with ethyl acetate (10 mL×2 times). The organic layer combined was washed with a saturated sodium chloride solution (10 mL) and dried over anhydrous magnesium sulfate. After removal of magnesium sulfate by filtration, the filtrate was evaporated to give crude product, which was purified by silica gel column (Wakogel C-200, ethyl acetate/hexane=1/1) to obtain a white solid of 2-(7-fluoro-4-methyl-2H-3(4H)-oxo-1,4-benzthioxazine-6-yl)-5,6-dihydroimidazo [1,5-a] pyridine-1,3[2H, 7H]-dione (0.08 g, yield:22.9%).

$^1$H-NMR(CDCl$_3$, TMS, ppm): δ1.83–2.19(m, 2H), 2.30–2.68(m, 2H), 3.41(s, 3H), 3.45(s, 2H), 3.78(t, J=6.30 Hz, 2H), 6.28(t, J=5.04 Hz, 1H), 7.01(d, J$_{HF}$=6.30 Hz, 1H), 7.28(d, J$_{HF}$=8.82 Hz, 1H).

mp:255°–280° C.

EXAMPLE-52

Synthesis of 2-(7-fluoro-4-propargyl-2H-3(4H)-oxo-1,4-benzthioxazine-6-yl)-5,6-dihydroimidazo [1,5-a] pyridine-1,3[2H, 7H]-dione

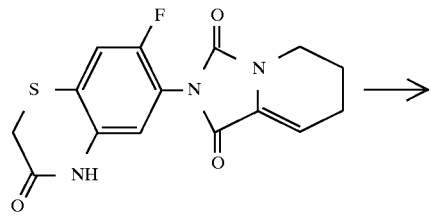

-continued

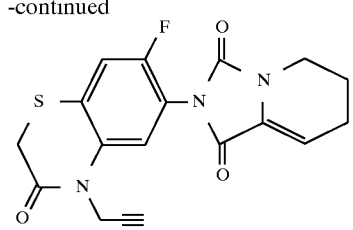

To an N,N-dimethylformamide (10 mL) solution of 2-(7-fluoro-2H-3(4H)-oxo-1,4-benzthioxazine-6-yl)-5,6-dihydroimidazo [1,5-a] pyridine-1,3[2H, 7H]-dione (0.33 g, 1.0 mmol) and potassium carbonate (0.14 g, 1.0 mmol) was dropwise added propargylbromide (0.1 mL, 1.1 mmol) at room temperature, and the mixture was stirred for 18 hours at the ambient temperature. 1N Hydrochloric acid (10 mL) and ethyl acetate (10 mL) were added to the resulting mixture and the organic layer was separated. The aqueous layer was extracted with ethyl acetate (10 mL×2 times). The organic layer combined was washed with a saturated sodium chloride solution (10 mL) and dried over anhydrous magnesium sulfate. After removal of magnesium sulfate by filtration, the filtrate was evaporated to give crude product, which was purified by silica gel column (Wakogel C-200, ethyl acetate/hexane=1/1) to obtain a white solid of 2-(7-fluoro-4-propargyl-2H-3(4H)-oxo-1,4-benzthioxazine-6-yl)-5,6-dihydroimidazo [1,5-a] pyridine-1,3[2H, 7H]-dione (0.05 g, yield:13.5%).

$^1$H-NMR(CDCl$_3$, TMS, ppm): δ1.81–2.26(m, 2H), 2.26–2.62(m, 3H), 3.50(s, 2H), 3.80(t, J=6.30 Hz, 2H), 4.71(d, J=2.52 Hz, 2H), 6.29(t, J=3.78 Hz, 1H), 7.20–7.45 (m, 2H).

mp:234°–237° C.

Examples of compounds of the present invention which can be prepared according to Process-1 to Process-8 and the processes described in Examples illustrated above are shown in Table 1 to 14 together with concrete examples of compounds described in Examples, but the present invention is not limited to these examples.

TABLE 1

| Compd. No. | Example No. | X$^1$ | X$^2$ | X$^3$ | X |
|---|---|---|---|---|---|
| 1 | | H | H | H | O |
| 2 | | H | H | Cl | O |
| 3 | | H | H | Br | S |
| 4 | | H | H | P | O |
| 5 | | H | H | CH$_3$ | O |
| 6 | | H | H | C$_2$H$_5$ | S |
| 7 | | H | H | OCH$_3$ | O |
| 8 | | H | H | NO$_2$ | O |
| 9 | | H | Cl | H | O |
| 10 | | H | Cl | Cl | S |
| 11 | | H | Cl | F | O |
| 12 | | H | Cl | CH$_3$ | S |
| 13 | | H | Cl | C$_2$H$_5$ | O |
| 14 | | H | Cl | OCH$_3$ | S |
| 15 | | H | Cl | NO$_2$ | O |
| 16 | | H | Br | H | O |
| 17 | | H | Br | CH$_3$ | S |
| 18 | | Cl | Br | H | O |
| 19 | | Br | Br | H | S |
| 20 | | Br | H | Br | O |
| 21 | | Cl | F | H | O |
| 22 | | H | F | Cl | S |
| 23 | | F | Cl | H | O |

TABLE 1-continued

| Compd. No. | Example No. | X¹ | X² | X³ | X |
|---|---|---|---|---|---|
| 24 | | F | Br | H | O |
| 25 | | Br | F | H | O |
| 26 | | Cl | CH₃ | H | O |
| 27 | | Cl | H | CH₃ | S |
| 28 | | CH₃ | Cl | H | O |
| 29 | | CH₃ | H | Cl | O |
| 30 | | F | CH₃ | H | O |
| 31 | | F | H | CH₃ | O |
| 32 | | H | CH₃ | F | S |

TABLE 2

| Compd. No. | Example No. | X¹ | X² | X³ | X |
|---|---|---|---|---|---|
| 33 | | CH₃ | F | H | O |
| 34 | | CH₃ | H | F | O |
| 35 | | Br | CH₃ | H | O |
| 36 | | H | CH₃ | Br | S |
| 37 | | Cl | H | OCH₃ | O |
| 38 | | Cl | H | NO₂ | S |
| 39 | | CH₃ | H | NO₂ | O |
| 40 | | H | CH₃ | NO₂ | O |
| 41 | | H | H | OH | S |
| 42 | | H | H | OCOOCH₃ | O |
| 43 | | H | H | OCH₃ | O |
| 44 | | H | H | OCH(CH₃)₂ | O |
| 45 | | H | H | O-cyclo-C₅H₉ | O |
| 46 | | H | H | O-cyclo-C₆H₁₁ | S |
| 47 | | H | H | OCH₂CH=CH₂ | O |
| 48 | | H | H | OCH₂C≡CH | O |
| 49 | | H | H | OCH(CH₃)C≡CH | O |
| 50 | | H | H | OCH₂COOCH₃ | O |
| 51 | | H | H | OCH₂COOC₅H₁₁ | S |
| 52 | | H | H | OCH₃C₆H₅ | O |
| 53 | | H | H | NO₂ | O |
| 54 | | H | H | NH₂ | O |
| 55 | | H | H | NHAc | O |
| 56 | | H | H | NHSO₂CH₃ | O |
| 57 | | H | H | NHSO₂C₆H₅ | S |
| 58 | | H | H | NHCOOCH₃ | S |
| 59 | | H | Cl | OH | O |
| 60 | | H | Cl | OCOOCH₃ | O |
| 61 | | H | Cl | OCH₃ | S |
| 62 | | H | Cl | OCH(CH₃)₂ | O |
| 63 | | H | Cl | O-cyclo-C₅H₉ | O |
| 64 | | H | Cl | O-cyclo-C₆H₁₁ | O |
| 65 | | H | Cl | OCH₂CH=CH₂ | O |
| 66 | | H | Cl | OCH₂C≡CH | S |
| 67 | | H | Cl | OCH(CH₃)C≡CH | O |
| 68 | | H | Cl | OCH₂COOCH₃ | O |
| 69 | | H | Cl | OCH₂COOC₅H₁₁ | O |
| 70 | | H | Cl | OCH₂C₆H₅ | O |
| 71 | | H | Cl | NO₂ | S |
| 72 | | H | Cl | NH₂ | O |
| 73 | | H | Cl | NHAc | O |
| 74 | | H | Cl | NHSO₂CH₃ | O |
| 75 | | H | Cl | NHSO₂C₆H₅ | S |
| 76 | | H | Cl | NHCOOCH₃ | O |

TABLE 3

| Compd. No. | Example No. | X¹ | X² | X³ | X |
|---|---|---|---|---|---|
| 77 | 27 | Cl | Cl | OH | O |
| 78 | 26 | Cl | Cl | OCOOCH₃ | O |
| 79 | 28 | Cl | Cl | OCH₃ | O |
| 80 | | Cl | Cl | OCH(CH₃)₂ | S |
| 81 | 32 | Cl | Cl | O-cyclo-C₅H₉ | O |
| 82 | | Cl | Cl | O-cyclo-C₆H₁₁ | S |
| 83 | 29 | Cl | Cl | OCH₂CH=CH₂ | O |
| 84 | 30 | Cl | Cl | OCH₂C≡CH | O |
| 85 | 31 | Cl | Cl | OCH(CH₃)C≡CH | O |
| 86 | | Cl | Cl | OCH₂COOCH₃ | S |
| 87 | | Cl | Cl | OCH₂COOC₅H₁₁ | O |
| 88 | | Cl | Cl | OCH₂C₆H₅ | O |
| 89 | | Cl | Cl | NO₂ | O |
| 90 | | Cl | Cl | NH₂ | O |
| 91 | | Cl | Cl | NHAc | S |
| 92 | | Cl | Cl | NHSO₂CH₃ | O |
| 93 | | Cl | Cl | NHSO₂C₆H₅ | O |
| 94 | | Cl | Cl | NHCOOCH₃ | O |
| 95 | 4 | F | Cl | OH | O |
| 96 | 3 | F | Cl | OCOOCH₃ | O |
| 97 | 5 | F | Cl | OCH₃ | O |
| 98 | | F | Cl | OCH(CH₃)₂ | S |
| 99 | 2.9 | F | Cl | O-cyclo-C₅H₉ | O |
| 100 | | F | Cl | O-cyclo-C₆H₁₁ | O |
| 101 | 6 | F | Cl | OCH₂CH=CH₂ | O |
| 102 | 7 | F | Cl | OCH₂C≡CH | O |
| 103 | 8 | F | Cl | OCH(CH₃)C₃CH | O |
| 104 | 18 | F | Cl | OCH₂COOCH₃ | O |
| 105 | 10 | F | Cl | OCH₂COOC₅H₁₁ | O |
| 106 | | F | Cl | OCH₂C₆H₅ | S |
| 107 | 12 | F | Cl | NO₂ | O |
| 108 | 13 | F | Cl | NH₂ | O |
| 109 | 14 | F | Cl | NHAc | O |
| 110 | 15 | F | Cl | NHSO₂CH₃ | O |
| 111 | 40 | F | Cl | NHSO₂C₆H₄CH₃—4 | O |
| 112 | | F | Cl | NHCOOCH₃ | S |
| 113 | | F | Br | OH | O |
| 114 | | F | Br | OCOOCH₃ | O |
| 115 | | F | Br | OCH₃ | S |
| 116 | | F | Br | OCH(CH₃)₂ | O |
| 117 | | F | Br | O-cyclo-C₅H₉ | S |
| 118 | | F | Br | O-cyclo-C₆H₁₁ | 0 |
| 119 | | F | Br | OCH₂CH=CH₂ | O |
| 120 | | F | Br | OCH₂C≡CH | O |

TABLE 4

| Compd. No. | Example No. | X¹ | X² | X³ | S |
|---|---|---|---|---|---|
| 121 | | F | Br | OCH(CH₃)C≡CH | S |
| 122 | | F | Br | OCH₂COOCH₃ | O |
| 123 | | F | Br | OCH₂COOC₅H₁₁ | O |
| 124 | | F | Br | OCH₂C₆H₅ | O |
| 125 | | F | Br | NO₂ | O |
| 126 | | F | Br | NH₂ | S |
| 127 | | F | Br | NHAc | O |
| 128 | | F | Br | NHSO₂CH₃ | O |
| 129 | | F | Br | NHSO₂C₆H₅ | O |
| 130 | | F | Br | NHCOOCH₃ | O |
| 131 | | H | F | OH | S |
| 132 | | H | F | OCOOCH₃ | O |
| 133 | | H | F | OCH₃ | O |
| 134 | | H | F | OCH(CH₃)₂ | O |
| 135 | | H | F | O-cyclo-C₅H₉ | S |
| 136 | | H | F | O-cyclo-C₆H₁₁ | O |
| 137 | | H | F | OCH₂CH=CH₂ | O |
| 138 | | H | F | OCH₂C≡CH | S |
| 139 | | H | F | OCH(CH₃)C≡CH | O |
| 140 | | H | F | OCH₂COOCH₃ | O |
| 141 | | H | F | OCH₂COOC₅H₁₁ | S |
| 142 | | H | F | OCH₂C₆H₅ | O |
| 143 | | H | F | NO₂ | O |
| 144 | | H | F | NH₂ | O |
| 145 | | H | F | NHAc | O |
| 146 | | H | F | NHSO₂CH₃ | S |
| 147 | | H | F | NHSO₂C₆H₅ | O |
| 148 | | H | F | NHCOOCH₃ | O |
| 149 | | F | F | OH | O |

TABLE 4-continued

| Compd. No. | Example No. | $X^1$ | $X^2$ | $X^3$ | S |
|---|---|---|---|---|---|
| 150 | | F | F | OCOOCH$_3$ | O |
| 151 | | F | F | OCH$_3$ | S |
| 152 | | F | F | OCH(CH$_3$)$_2$ | O |
| 153 | | F | F | O-cyclo-C$_5$H$_9$ | O |
| 154 | | F | F | O-cyclo-C$_6$H$_{11}$ | O |
| 155 | | F | F | OCH$_2$CH=CH$_2$ | S |
| 156 | | F | F | OCH$_2$C≡CH | O |
| 157 | | F | F | OCH(CH$_3$)C≡CH | O |
| 158 | | F | F | OCH$_2$COOCH$_3$ | S |
| 159 | | F | F | OCH$_2$COOC$_5$H$_{11}$ | O |
| 160 | | F | F | OCH$_2$C$_6$H$_5$ | O |
| 161 | 11 | F | F | NO$_2$ | O |
| 162 | | F | F | NH$_2$ | O |
| 163 | | F | F | NHAc | O |
| 164 | | F | F | NHSO$_2$CH$_3$ | S |

TABLE 5

| Compd. No. | Example No. | $X^1$ | $X^2$ | $X^3$ | X |
|---|---|---|---|---|---|
| 165 | | F | F | NHSO$_2$C$_6$H$_5$ | O |
| 166 | | F | F | NHCOOCH$_3$ | S |
| 167 | | H | Br | OH | O |
| 168 | | H | Br | OCOOCH$_3$ | O |
| 169 | | H | Br | OCH$_3$ | O |
| 170 | | H | Br | OCH(CH$_3$)$_2$ | O |
| 171 | | H | Br | O-cyclo-C$_5$H$_9$ | S |
| 172 | | H | Br | O-cyclo-C$_6$H$_{11}$ | O |
| 173 | | H | Br | OCH$_2$CH=CH$_2$ | O |
| 174 | | H | Br | OCH$_2$C$_2$CH | O |
| 175 | | H | Br | OCH(CH$_3$)C≡CH | S |
| 176 | | H | Br | OCH$_2$COOCH$_3$ | O |
| 177 | | H | Br | OCH$_2$COOC$_5$H$_{11}$ | O |
| 178 | | H | Br | OCH$_2$C$_6$H$_5$ | S |
| 179 | | H | Br | NO$_2$ | O |
| 180 | | H | Br | NH$_2$ | O |
| 181 | | H | Br | NHAc | S |
| 182 | | H | Br | NHSO$_2$CH$_3$ | O |
| 183 | | H | Br | NHSO$_2$C$_6$H$_5$ | O |
| 184 | | H | Br | NHCOOCH$_3$ | O |
| 185 | | Br | Br | OH | O |
| 186 | | Br | Br | OCOOCH$_3$ | S |
| 187 | | Br | Br | OCH$_3$ | O |
| 188 | | Br | Br | OCH(CH$_3$)$_2$ | O |
| 189 | | Br | Br | O-cyclo-C$_5$H$_{11}$ | O |
| 190 | | Br | Br | O-cyclo-C$_6$H$_{13}$ | O |
| 191 | | Br | Br | OCH$_2$CH=CH$_2$ | S |
| 192 | | Br | Br | OCH$_2$C≡CH | O |
| 193 | | Br | Br | OCH(CH$_3$)C≡CH | O |
| 194 | | Br | Br | OCH$_2$COOCH$_3$ | O |
| 195 | | Br | Br | OCH$_2$COOC$_5$H$_{11}$ | S |
| 196 | | Br | Br | OCH$_2$C$_6$H$_5$ | O |
| 197 | | Br | Br | NO$_2$ | O |
| 198 | | Br | Br | NH$_2$ | S |
| 199 | | Br | Br | NHAc | O |
| 200 | | Br | Br | NHSO$_2$CH$_3$ | O |
| 201 | | Br | Br | NHSO$_2$C$_6$H$_5$ | S |
| 202 | | Br | Br | NHCOOCH$_3$ | O |
| 203 | | Cl | H | OH | O |
| 204 | | Cl | H | OCOOCH$_3$ | O |
| 205 | | Cl | H | OCH$_3$ | O |
| 206 | | Cl | H | OCH(CH$_3$)$_2$ | S |
| 207 | | Cl | H | O-cyclo-C$_5$H$_9$ | O |
| 208 | | Cl | H | O-cyclo-C$_6$H$_{11}$ | O |

TABLE 6

| Compd. No. | Example No. | $X^1$ | $X^2$ | $X^3$ | X |
|---|---|---|---|---|---|
| 209 | | Cl | H | OCH$_2$CH=CH$_2$ | O |
| 210 | | Cl | H | OCH$_2$C≡CH | O |
| 211 | | Cl | H | OCH(CH$_3$)C≡CH | S |
| 212 | | Cl | H | OCH$_2$COOCH$_3$ | O |
| 213 | | Cl | H | OCH$_2$COOC$_5$H$_{11}$ | O |
| 214 | | Cl | H | OCH$_2$C$_6$H$_5$ | O |
| 215 | | Cl | H | NO$_2$ | S |
| 216 | | Cl | H | NH$_2$ | O |
| 217 | | Cl | H | NHAc | O |
| 218 | | Cl | H | NHSO$_2$CH$_3$ | S |
| 219 | | Cl | H | NHSO$_2$C$_6$H$_5$ | O |
| 220 | | Cl | H | NHCOOCH$_3$ | O |
| 221 | | Br | H | OH | S |
| 222 | | Br | H | OCOOCH$_3$ | O |
| 223 | | Br | H | OCH$_3$ | O |
| 224 | | Br | H | OCH(CH$_3$)$_2$ | O |
| 225 | | Br | H | O-cyclo-C$_5$H$_9$ | O |
| 226 | | Br | H | O-cyclo-C$_6$H$_{11}$ | S |
| 227 | | Br | H | OCH$_2$CH=CH$_2$ | O |
| 228 | | Br | H | OCH$_2$C$_2$C≡CH | O |
| 229 | | Br | H | OCH(CH$_3$)C≡CH | O |
| 230 | | Br | H | OCH$_2$COOCH$_3$ | O |
| 231 | | Br | H | OCH$_2$COOC$_5$H$_{11}$ | S |
| 232 | | Br | H | OCH$_2$C$_6$H$_5$ | O |
| 233 | | Br | H | NO$_2$ | O |
| 234 | | Br | H | NH$_2$ | O |
| 235 | | Br | H | NHAc | S |
| 236 | | Br | H | NHSO$_2$CH$_3$ | O |
| 237 | | Br | H | NHSO$_2$C$_6$H$_5$ | O |
| 238 | | Br | H | NHCOOCH$_3$ | S |
| 239 | | F | H | OH | O |
| 240 | | F | H | OCOOCH$_3$ | O |
| 241 | | F | H | OCH$_3$ | S |
| 242 | | F | H | OCH(CH$_3$)$_2$ | O |
| 243 | | F | H | O-cyclo-C$_5$H$_9$ | O |
| 244 | | F | H | O-cyclo-C$_6$H$_{11}$ | O |
| 245 | | F | H | OCH$_2$CH=CH$_2$ | O |
| 246 | | F | H | OCH$_2$C≡CH | S |
| 247 | | F | H | OCH(CH$_3$)C≡CH | O |
| 248 | | F | H | OCH$_2$COOCH$_3$ | O |
| 249 | | F | H | OCH$_2$COOC$_5$H$_{11}$ | O |
| 250 | | F | H | OCH$_2$C$_6$H$_5$ | O |
| 251 | | F | H | NO$_2$ | S |
| 252 | | F | H | NH$_2$ | O |

TABLE 7

| Compd. No. | Example No. | $X^1$ | $X^2$ | $X^3$ | X |
|---|---|---|---|---|---|
| 253 | | F | H | NHAc | O |
| 254 | | F | H | NHSO$_2$CH$_3$ | O |
| 255 | | F | H | NHSO$_2$C$_6$H$_5$ | S |
| 256 | | F | H | NHCOOCH$_3$ | O |
| 257 | | Cl | F | OH | O |
| 258 | | Cl | F | OCOOCH$_3$ | S |
| 259 | | Cl | F | OCH$_3$ | O |
| 260 | | Cl | F | OCH(CH$_3$)$_2$ | O |
| 261 | | Cl | F | O-cyclo-C$_5$H$_9$ | S |
| 262 | | Cl | F | O-cyclo-C$_6$H$_{11}$ | O |
| 263 | | Cl | F | OCH$_2$CH=CH$_2$ | O |
| 264 | | Cl | F | OCH$_2$C≡CH | O |
| 265 | | Cl | F | OCH(CH$_3$)C≡CH | O |
| 266 | | Cl | F | OCH$_2$COOCH$_3$ | S |
| 267 | | Cl | F | OCH$_2$COOC$_5$H$_{11}$ | O |
| 268 | | Cl | F | OCH$_2$C$_6$H$_5$ | O |
| 269 | | Cl | F | NO$_2$ | O |
| 270 | | Cl | F | NH$_2$ | O |
| 271 | | Cl | F | NHAc | S |
| 272 | | Cl | F | NHSO$_2$CH$_3$ | O |
| 273 | | Cl | F | NHSO$_2$C$_6$H$_5$ | O |
| 274 | | Cl | F | NHCOOCH$_3$ | O |
| 275 | | Br | F | OH | S |

TABLE 7-continued

| Compd. No. | Example No. | X$^1$ | X$^2$ | X$^3$ | X |
|---|---|---|---|---|---|
| 276 | | Br | F | OCOOCH$_3$ | O |
| 277 | | Br | F | OCH$_3$ | O |
| 278 | | Br | F | OCH(CH$_3$)$_2$ | S |
| 279 | | Br | F | O-cyclo-C$_5$H$_9$ | O |
| 280 | | Br | F | O-cyclo-C$_6$H$_{11}$ | O |
| 281 | | Br | F | OCH$_2$CH=CH$_2$ | S |
| 282 | | Br | F | OCH$_2$C≡CH | O |
| 283 | | Br | F | OCH(CH$_3$)C≡CH | O |
| 284 | | Br | F | OCH$_2$COOCH$_3$ | O |
| 285 | | Br | F | OCH$_2$COOC$_5$H$_{11}$ | O |
| 286 | | Br | F | OCH$_2$C$_6$H$_5$ | S |
| 287 | | Br | F | NO$_2$ | O |
| 288 | | Br | F | NH$_2$ | O |
| 289 | | Br | F | NHAc | O |
| 290 | | Br | F | NHSO$_2$CH$_3$ | O |
| 291 | | Br | F | NHSO$_2$C$_6$H$_5$ | S |
| 292 | | Br | F | NHCOOCH$_3$ | O |
| 293 | | Br | Cl | OH | O |
| 294 | | Br | Cl | OCOOCH$_3$ | O |
| 295 | | Br | Cl | OCOOCH$_2$C$_6$H$_5$ | O |
| 296 | | Br | Cl | OCH$_3$ | S |

TABLE 8

| Compd. No. | Example No. | X$^1$ | X$^2$ | X$^3$ | X |
|---|---|---|---|---|---|
| 297 | | Br | Cl | OCH(CH$_3$)$_2$ | O |
| 298 | | Br | Cl | OCH$_2$CH=CH$_2$ | O |
| 299 | | Br | Cl | OCH$_2$C≡CH | O |
| 300 | | Br | Cl | OCH(CH$_3$)C≡CH | S |
| 301 | | Br | Cl | OCH$_2$COOCH$_3$ | O |
| 302 | | Br | Cl | OCH$_2$COOC$_5$H$_{11}$ | O |
| 303 | | Br | Cl | OCH$_2$C$_6$H$_5$ | O |
| 304 | | Br | Cl | NO$_2$ | O |
| 305 | | Br | Cl | NH$_2$ | S |
| 306 | | Br | Cl | NHAc | O |
| 307 | | Br | Cl | NHSO$_2$CH$_3$ | O |
| 308 | | Br | Cl | NHSO$_2$C$_6$H$_5$ | O |
| 309 | | Br | Cl | NHCOOCH$_3$ | O |
| 310 | | Br | Cl | O-cyclo-C$_3$H$_5$ | O |
| 311 | | Br | Cl | O-cyclo-C$_5$H$_9$ | S |
| 312 | | Br | Cl | O-cyclo-C$_6$H$_{11}$ | O |
| 313 | 17 | F | Cl | OCH$_2$COCH$_3$ | O |
| 314 | 16 | F | Cl | OCH(CH$_3$)COCH$_3$ | O |
| 315 | | F | Cl | OCH(Et)COCH$_3$ | O |
| 316 | | F | Cl | OCH(CH$_3$)COPr | O |
| 317 | 33 | F | Cl | SCH$_3$ | O |
| 318 | | F | Cl | SCH$_2$CH$_3$ | O |
| 319 | 34 | F | Cl | SCH(CH$_3$)$_2$ | O |
| 320 | 35 | F | Cl | SCH$_2$CH=CH$_2$ | O |
| 321 | 36 | F | Cl | SCH$_2$C≡CH | O |
| 322 | 37 | F | Cl | SCH(CH$_3$)C≡CH | O |
| 323 | 38 | F | Cl | SCH$_2$COOCH$_3$ | O |
| 324 | 39 | F | Cl | SCH$_2$COOC$_5$H$_9$ | O |
| 325 | | F | Cl | SCH$_2$COOCH$_2$C$_6$H$_5$ | O |
| 326 | | F | Cl | S-cyclo-C$_3$H$_5$ | O |
| 327 | | F | Cl | S-cyclo-C$_5$H$_9$ | O |
| 328 | | F | Cl | S-cyclo-C$_6$H$_{11}$ | O |
| 329 | | F | Cl | SCH$_2$C$_6$H$_5$ | S |
| 330 | | F | Cl | SCH$_2$C$_6$H$_4$F | O |
| 331 | | F | Cl | SCH$_2$C$_6$H$_4$CH$_3$ | S |
| 332 | | F | Cl | NO$_2$ | S |
| 333 | | F | Cl | NH$_2$ | S |
| 334 | | F | Cl | NHAc | S |
| 335 | | F | Cl | NHSO$_2$CH$_3$ | S |
| 336 | 41 | F | Cl | SCH$_2$COOCH$_3$ | S |
| 337 | | F | Cl | SCH$_2$COOC$_5$H$_{11}$ | S |
| 338 | | F | Cl | SCH$_2$COOCH2C6H5 | S |
| 339 | | F | Cl | S-cyclo-C$_3$H$_5$ | S |
| 340 | | F | Cl | S-cyclo-C$_5$H$_9$ | S |

TABLE 9

| Compd. No. | Example No. | X$^1$ | X$^2$ | X$^3$ | X |
|---|---|---|---|---|---|
| 341 | | F | Cl | S-cyclo-C$_6$H$_{11}$ | S |
| 342 | | F | Cl | OCH$_2$C≡CH | S |
| 343 | 42 | F | Cl | OCH(CH$_3$)C≡CH | S |
| 344 | | F | Cl | SCH$_2$C≡CH | S |
| 345 | | F | Cl | SCH(CH$_3$)C≡CH | S |
| 346 | 20 | Cl | CH$_3$ | OH | O |
| 347 | | Cl | CH$_3$ | SH | O |
| 348 | 21 | Cl | CH$_3$ | OCH$_3$ | O |
| 349 | | Cl | CH$_3$ | OCH$_3$ | S |
| 350 | | Cl | CH$_3$ | SC$_2$H$_5$ | O |
| 351 | | Cl | CH$_3$ | OC$_2$H$_5$ | O |
| 352 | | Cl | CH$_3$ | OCH(CH$_3$)$_2$ | O |
| 353 | | Cl | CH$_3$ | OCH(CH$_3$)$_2$ | O |
| 354 | | Cl | CH$_3$ | S-cyclo-C$_3$H$_5$ | S |
| 355 | | Cl | CH$_3$ | O-cyclo-C$_3$H$_5$ | O |
| 356 | 25 | Cl | CH$_3$ | O-cyclo-C$_5$H$_9$ | O |
| 357 | | Cl | CH$_3$ | S-cyclo-C$_5$H$_9$ | O |
| 358 | | Cl | CH$_3$ | OCH$_2$NO$_2$ | O |
| 359 | | Cl | CH$_3$ | SCH$_2$NO$_2$ | S |
| 360 | | Cl | CH$_3$ | OCH$_2$CN | O |
| 361 | | Cl | CH$_3$ | OCH$_2$COOCH$_3$ | O |
| 362 | | Cl | CH$_3$ | OCH$_2$COOCH$_3$ | O |
| 363 | | Cl | CH$_3$ | SCH$_2$C$_6$H$_5$ | O |
| 364 | 22 | Cl | CH$_3$ | OCH$_2$CH=CH$_2$ | O |
| 365 | | Cl | CH$_3$ | OCH$_2$CH=CH$_2$ | O |
| 366 | 23 | Cl | CH$_3$ | OCH$_2$C≡CH | O |
| 367 | | Cl | CH$_3$ | OCH$_2$C≡CH | S |
| 368 | 24 | Cl | CH$_3$ | OCH(CH$_3$)C≡CH | O |

Examples of the bicyclic hydantoin derivatives represented by the general formula (22) are summerized in the following Table-10 to Table-14.

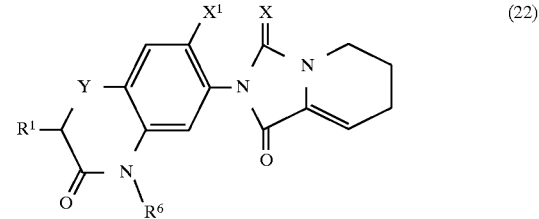

(22)

TABLE 10

| Compd. No. | Example No. | X$^1$ | R$^1$ | R$^2$ | X | Y |
|---|---|---|---|---|---|---|
| 369 | | H | H | H | O | O |
| 370 | | H | H | H | O | S |
| 371 | | H | H | CH$_3$ | O | O |
| 372 | | H | H | CH$_3$ | S | S |
| 373 | | H | H | C$_2$H$_5$ | O | O |
| 374 | | H | H | C$_2$H$_5$ | O | S |
| 375 | | H | H | CH(CH$_3$)$_2$ | O | O |
| 376 | | H | H | CH(CH$_3$)$_2$ | O | S |
| 377 | | H | H | cyclo-C$_3$H$_5$ | S | O |
| 378 | | H | H | cyclo-C$_3$H$_5$ | O | S |
| 379 | | H | H | CH$_2$NO$_2$ | O | O |
| 380 | | H | H | CH$_2$NO$_2$ | O | S |
| 381 | | H | H | CH$_2$CN | O | O |
| 382 | | H | H | CH$_2$CN | S | S |
| 383 | | H | H | CH$_2$COOCH$_3$ | O | O |
| 384 | | H | H | CH$_2$COOCH$_3$ | O | S |
| 385 | | H | H | CH$_2$C$_6$H$_5$ | O | O |
| 386 | | H | H | CH$_2$C$_6$H$_5$ | O | S |
| 387 | | H | H | CH$_2$CH=CH$_2$ | S | O |
| 388 | | H | H | CH$_2$CH=CH$_2$ | O | S |
| 389 | | H | H | CH$_2$C≡CH | O | O |
| 390 | | H | H | CH$_2$C≡CH | O | S |
| 391 | | H | CH$_3$ | H | O | O |

TABLE 10-continued

| Compd. No. | Example No. | X¹ | R¹ | R² | X | Y |
|---|---|---|---|---|---|---|
| 392 | | H | CH₃ | H | O | S |
| 393 | | H | CH₃ | CH₃ | S | O |
| 394 | | H | CH₃ | CH₃ | O | S |
| 395 | | H | CH₃ | C₂H₅ | O | O |
| 396 | | H | CH₃ | C₂H₅ | O | S |
| 397 | | H | CH₃ | CH(CH₃)₂ | O | O |
| 398 | | H | CH₃ | CH(CH₃)₂ | S | S |
| 399 | | H | CH₃ | cyclo-C₃H₅ | O | O |
| 400 | | H | CH₃ | cyclo-C₃H₅ | O | S |
| 401 | | H | CH₃ | CH₂NO₂ | O | O |
| 402 | | H | CH₃ | CH₂NO₂ | O | S |
| 403 | | H | CH₃ | CH₂CN | S | O |
| 404 | | H | CH₃ | CH₂CN | O | S |
| 405 | | H | CH₃ | CH₂COOCH₃ | O | O |
| 406 | | H | CH₃ | CH₂COOCH₃ | O | S |
| 407 | | H | CH₃ | CH₂C₆H₅ | O | O |
| 408 | | H | CH₃ | CH₂C₆H₅ | S | S |
| 409 | | H | CH₃ | CH₂CH=CH₂ | O | O |
| 410 | | H | CH₃ | CH₂CH=CH₂ | O | S |
| 411 | | H | CH₃ | CH₂C≡CH | O | O |
| 412 | | H | CH₃ | CH₂C≡CH | O | S |

TABLE 11

| Compd. No. | Example No. | X¹ | R¹ | R² | X | Y |
|---|---|---|---|---|---|---|
| 413 | | CH₃ | H | H | O | O |
| 414 | | CH₃ | H | H | S | S |
| 415 | | CH₃ | H | CH₃ | O | O |
| 416 | | CH₃ | H | CH₃ | O | S |
| 417 | | CH₃ | H | C₂H₅ | O | O |
| 418 | | CH₃ | H | C₂H₅ | O | S |
| 419 | | CH₃ | H | CH(CH₃)₂ | S | O |
| 420 | | CH₃ | H | CH(CH₃)₂ | O | S |
| 421 | | CH₃ | H | cyclo-C₃H₅ | O | O |
| 422 | | CH₃ | H | cyclo-C₃H₅ | O | S |
| 423 | | CH₃ | H | CH₂NO₂ | O | O |
| 424 | | CH₃ | H | CH₂NO₂ | S | S |
| 425 | | CH₃ | H | CH₂CN | O | O |
| 426 | | CH₃ | H | CH₂CN | O | S |
| 427 | | CH₃ | H | CH₂COOCH₃ | O | O |
| 428 | | CH₃ | H | CH₂COOCH₃ | O | S |
| 429 | | CH₃ | H | CH₂C₆H₅ | S | O |
| 430 | | CH₃ | H | CH₂C₆H₅ | O | S |
| 431 | | CH₃ | H | CH₂CH=CH₂ | O | O |
| 432 | | CH₃ | H | CH₂CH=CH₂ | O | S |
| 433 | | CH₃ | H | CH₂C≡CH | O | O |
| 434 | | CH₃ | H | CH₂C≡CH | S | S |
| 435 | | CH₃ | CH₃ | H | O | O |
| 436 | | CH₃ | CH₃ | H | O | S |
| 437 | | CH₃ | CH₃ | CH₃ | O | O |
| 438 | | CH₃ | CH₃ | CH₃ | O | S |
| 439 | | CH₃ | CH₃ | C₂H₅ | S | O |
| 440 | | CH₃ | CH₃ | C₂H₅ | O | S |
| 441 | | CH₃ | CH₃ | CH(CH₃)₂ | O | O |
| 442 | | CH₃ | CH₃ | CH(CH₃)₂ | O | S |
| 443 | | CH₃ | CH₃ | cyclo-C₃H₅ | O | O |
| 444 | | CH₃ | CH₃ | cyclo-C₃H₅ | S | O |
| 445 | | CH₃ | CH₃ | CH₂NO₂ | O | O |
| 446 | | CH₃ | CH₃ | CH₂NO₂ | O | S |
| 447 | | CH₃ | CH₃ | CH₂CN | O | O |
| 448 | | CH₃ | CH₃ | CH₂CN | O | S |
| 449 | | CH₃ | CH₃ | CH₂COOCH₃ | S | O |
| 450 | | CH₃ | CH₃ | CH₂COOCH₃ | O | S |
| 451 | | CH₃ | CH₃ | CH₂C₆H₅ | O | O |
| 452 | | CH₃ | CH₃ | CH₂C₆H₅ | O | S |
| 453 | | CH₃ | CH₃ | CH₂CH=CH₂ | O | O |
| 454 | | CH₃ | CH₃ | CH₂CH=CH₂ | O | S |
| 455 | | CH₃ | CH₃ | CH₂C≡CH | S | O |
| 456 | | CH₃ | CH₃ | CH₂C≡CH | O | S |

TABLE 12

| Compd. No. | Example No. | X¹ | R¹ | R² | X | Y |
|---|---|---|---|---|---|---|
| 457 | 44 | F | H | H | O | O |
| 458 | 49 | F | H | H | O | S |
| 459 | 46 | F | H | CH₃ | O | O |
| 460 | 51 | F | H | CH₃ | S | S |
| 461 | | F | H | C₂H₅ | O | O |
| 462 | | F | H | C₂H₅ | O | S |
| 463 | | F | H | CH(CH₃)₂ | O | O |
| 464 | | F | H | CH(CH₃)₂ | O | S |
| 465 | | F | H | cyclo-C₃H₅ | S | O |
| 466 | | F | H | cyclo-C₃H₅ | O | S |
| 467 | | F | H | CH₂NO₂ | O | O |
| 468 | | F | H | CH₂NO₂ | O | S |
| 469 | | F | H | CH₂CN | O | O |
| 470 | | F | H | CH₂CN | S | S |
| 471 | | F | H | CH₂COOCH₃ | O | O |
| 472 | | F | H | CH₂COOCH₃ | O | S |
| 473 | | F | H | CH₂C₆H₅ | O | O |
| 474 | | F | H | CH₂C₆H₅ | O | S |
| 475 | 45 | F | H | CH₂CH=CH₂ | O | O |
| 476 | 50 | F | H | CH₂CH=CH₂ | S | S |
| 477 | 47 | F | H | CH₂C≡CH | O | O |
| 478 | 52 | F | H | CH₂C≡CH | O | S |
| 479 | | F | CH₃ | H | O | O |
| 480 | | F | CH₃ | H | O | S |
| 481 | | F | CH₃ | CH₃ | S | O |
| 482 | | F | CH₃ | CH₃ | O | S |
| 483 | | F | CH₃ | C₂H₅ | O | O |
| 484 | | F | CH₃ | C₂H₅ | O | S |
| 485 | | F | CH₃ | CH(CH₃)₂ | O | O |
| 486 | | F | CH₃ | CH(CH₃)₂ | S | S |
| 487 | | F | CH₃ | cyclo-C₃H₅ | O | O |
| 488 | | F | CH₃ | cyclo-C₃H₅ | O | S |
| 489 | | F | CH₃ | CH₂NO₂ | O | O |
| 490 | | F | CH₃ | CH₂NO₂ | O | S |
| 491 | | F | CH₃ | CH₂CN | S | O |
| 492 | | F | CH₃ | CH₂CN | O | S |
| 493 | | F | CH₃ | CH₂COOCH₃ | O | O |
| 494 | | F | CH₃ | CH₂COOCH₃ | O | S |
| 495 | | F | CH₃ | CH₂C₆H₅ | O | O |
| 496 | | F | CH₃ | CH₂C₆H₅ | O | S |
| 497 | | F | CH₃ | CH₂CH=CH₂ | S | O |
| 498 | | F | CH₃ | CH₂CH=CH₂ | O | S |
| 499 | | F | CH₃ | CH₂C≡CH | O | O |
| 500 | | F | CH₃ | CH₂C≡CH | O | S |

TABLE 13

| Compd. No. | Example No. | X¹ | R¹ | R² | X | Y |
|---|---|---|---|---|---|---|
| 501 | | Cl | H | H | O | O |
| 502 | | Cl | H | H | S | S |
| 503 | | Cl | H | CH₃ | O | O |
| 504 | | Cl | H | CH₃ | O | S |
| 505 | | Cl | H | C₂H₅ | O | O |
| 506 | | Cl | H | C₂H₅ | O | S |
| 507 | | Cl | H | CH(CH₃)₂ | S | O |
| 508 | | Cl | H | CH(CH₃)₂ | O | S |
| 509 | | Cl | H | cyclo-C₃H₅ | O | O |
| 510 | | Cl | H | cyclo-C₃H₅ | O | S |
| 511 | | Cl | H | CH₂NO₂ | O | O |
| 512 | | Cl | H | CH₂NO₂ | S | S |
| 513 | | Cl | H | CH₂CN | O | O |
| 514 | | Cl | H | CH₂CN | O | S |
| 515 | | Cl | H | CH₂COOCH₃ | O | O |
| 516 | | Cl | H | CH₂COOCH₃ | O | S |
| 517 | | Cl | H | CH₂C₆H₅ | O | O |
| 518 | | Cl | H | CH₂C₆H₅ | S | S |
| 519 | | Cl | H | CH₂CH=CH₂ | O | O |
| 520 | | Cl | H | CH₂CH=CH₂ | O | S |
| 521 | | Cl | H | CH₂C≡CH | O | O |
| 522 | | Cl | H | CH₂C≡CH | O | S |
| 523 | | Cl | CH₃ | H | S | O |

TABLE 13-continued

| Compd. No. | Example No. | $X^1$ | $R^1$ | $R^2$ | X | Y |
|---|---|---|---|---|---|---|
| 524 | | Cl | $CH_3$ | H | O | S |
| 525 | | Cl | $CH_3$ | $CH_3$ | O | O |
| 526 | | Cl | $CH_3$ | $CH_3$ | O | S |
| 527 | | Cl | $CH_3$ | $C_2H_5$ | O | O |
| 528 | | Cl | $CH_3$ | $C_2H_5$ | S | S |
| 529 | | Cl | $CH_3$ | $CH(CH_3)_2$ | O | O |
| 530 | | Cl | $CH_3$ | $CH(CH_3)_2$ | O | S |
| 531 | | Cl | $CH_3$ | cyclo-$C_3H_5$ | O | O |
| 532 | | Cl | $CH_3$ | cyclo-$C_3H_5$ | O | S |
| 533 | | Cl | $CH_3$ | $CH_2NO_2$ | S | O |
| 534 | | Cl | $CH_3$ | $CH_2NO_2$ | O | S |
| 535 | | Cl | $CH_3$ | $CH_2CN$ | O | O |
| 536 | | Cl | $CH_3$ | $CH_2CN$ | O | S |
| 537 | | Cl | $CH_3$ | $CH_2COOCH_3$ | O | O |
| 538 | | Cl | $CH_3$ | $CH_2COOCH_3$ | O | S |
| 539 | | Cl | $CH_3$ | $CH_2C_6H_5$ | S | O |
| 540 | | Cl | $CH_3$ | $CH_2C_6H_5$ | O | S |
| 541 | | Cl | $CH_3$ | $CH_2CH{=}CH_2$ | O | O |
| 542 | | Cl | $CH_3$ | $CH_2CH{=}CH_2$ | O | S |
| 543 | | Cl | $CH_3$ | $CH_2C{\equiv}CH$ | O | O |
| 544 | | Cl | $CH_3$ | $CH_2C{\equiv}CH$ | S | S |

TABLE 14

| Compd. No. | Example No. | $X^1$ | $R^1$ | $R^2$ | X | Y |
|---|---|---|---|---|---|---|
| 545 | | Br | H | H | O | O |
| 546 | | Br | H | H | O | S |
| 547 | | Br | H | $CH_3$ | O | O |
| 548 | | Br | H | $CH_3$ | O | S |
| 549 | | Br | H | $C_2H_5$ | S | O |
| 550 | | Br | H | $C_2H_5$ | O | S |
| 551 | | Br | H | $CH(CH_3)_2$ | O | O |
| 552 | | Br | H | $CH(CH_3)_2$ | O | S |
| 553 | | Br | H | cyclo-$C_3H_5$ | O | O |
| 554 | | Br | H | cyclo-$C_3H_5$ | S | S |
| 555 | | Br | H | $CH_2NO_2$ | O | O |
| 556 | | Br | H | $CH_2NO_2$ | O | S |
| 557 | | Br | H | $CH_2CN$ | O | O |
| 558 | | Br | H | $CH_2CN$ | O | S |
| 559 | | Br | H | $CH_2COOCH_3$ | O | O |
| 560 | | Br | H | $CH_2COOCH_3$ | S | S |
| 561 | | Br | H | $CH_2C_6H_5$ | O | O |
| 562 | | Br | H | $CH_2C_6H_5$ | O | S |
| 563 | | Br | H | $CH_2CH{=}CH_2$ | O | O |
| 564 | | Br | H | $CH_2CH{=}CH_2$ | O | S |
| 565 | | Br | H | $CH_2C{\equiv}CH$ | S | O |
| 566 | | Br | H | $CH_2C{\equiv}CH$ | O | S |
| 567 | | Br | $CH_3$ | H | O | O |
| 568 | | Br | $CH_3$ | H | O | S |
| 569 | | Br | $CH_3$ | $CH_3$ | O | O |
| 570 | | Br | $CH_3$ | $CH_3$ | S | S |
| 571 | | Br | $CH_3$ | $C_2H_5$ | O | O |
| 572 | | Br | $CH_3$ | $C_2H_5$ | O | S |
| 573 | | Br | $CH_3$ | $CH(CH_3)_2$ | O | O |
| 574 | | Br | $CH_3$ | $CH(CH_3)_2$ | O | S |
| 575 | | Br | $CH_3$ | cyclo-$C_3H_5$ | S | O |
| 576 | | Br | $CH_3$ | cyclo-$C_3H_5$ | O | S |
| 577 | | Br | $CH_3$ | $CH_2NO_2$ | O | O |
| 578 | | Br | $CH_3$ | $CH_2NO_2$ | O | S |
| 579 | | Br | $CH_3$ | $CH_2CN$ | O | O |
| 580 | | Br | $CH_3$ | $CH_2CN$ | O | S |
| 581 | | Br | $CH_3$ | $CH_2COOCH_3$ | S | O |
| 582 | | Br | $CH_3$ | $CH_2COOCH_3$ | O | O |
| 583 | | Br | $CH_3$ | $CH_2C_6H_5$ | O | O |
| 584 | | Br | $CH_3$ | $CH_2C_6H_5$ | O | S |
| 585 | | Br | $CH_3$ | $CH_2CH{=}CH_2$ | O | O |
| 586 | | Br | $CH_3$ | $CH_2CH{=}CH_2$ | S | S |
| 587 | | Br | $CH_3$ | $CH_2C{\equiv}CH$ | O | O |
| 588 | | Br | $CH_3$ | $CH_2C{\equiv}CH$ | O | S |

The compounds of the present invention can be used solely as a herbicide, but generally they can be used in combination with one or more auxiliary agents. Generally, it is preferable to use them by incorporating various carriers, fillers, solvent, surface active agents, stabilizers, etc. as auxiliary agents, and formulating into preparations in the form of a wettable powder, an emulsion, a powder, a granule, and a flowable agent by a usual method.

As the solvent which is one of the auxiliary agents in the herbicide containing the compound of the present invention as an active ingredient, water, alcohols, ketones, ethers, aliphatic and aromatic hydrocarbons, halogenated hydrocarbons, acidamides, esters and nitrites are suitable, and one of these solvents or a mixture of two or more solvents can be used.

As the filler, mineral powders, for example, clays such as kaolin, bentonite, etc., talcs such as talc, pyrophylite, etc., and oxides such as diatomaceous earth, white carbon, etc., and vegetable powders such as soybean powder, CMC, etc. can be used. Also, a surface active agent may be used as a spreading agent, a dispersing agent, an emulsifying agent and a penetrating agent. Examples of the surface active agents include nonionic surface active agents, cationic surface agents and amphoteric surface active agents. One of these surface active agents or a mixture of two or more thereof can be used depending upon the utility thereof.

Preferred methods for using the herbicide containing the compound of the present invention as an active ingredient include a soil treatment, a water surface treatment, and stem-foliar treatment, and a particularly excellent effect can be achieved by application prior to germination to a germ stage.

Further, the herbicide containing the compound of the present invention as an active ingredient can be used in admixture with or together with other active ingredients which do not adversely affect the herbicidal activity of the present active ingredient, for example, other herbicidal agents, insecticidal agents, fungicidal agents, plant growth controlling agents, etc.

Hereinafter, the present invention is further illustrated by the preparation examples of the herbicidal agents containing the compound of the present invention as an active ingredient, and the test examples studying herbicidal effects by the present herbicide. In these examples, part is part by weight.

Preparation Example-1 (Emulsion)

20 Parts of the compound of the present invention, 35 parts of xylene, 40 parts of cyclohexanone and 5 parts of Sorbol 900A (produced by Toho Chemical Industry Co., Ltd.) were uniformly mixed to prepare an emulsion.

Preparation Example-2 (Wettable Powder)

A mixture of 50 parts of the compound of the present invention, 25 parts of diatomaceous earth, 22 parts of clay and 3 parts of Lennox R100C (produced by Toho Chemical Industry Co., Ltd.) was mixed and ground to prepare a wettable powder.

Preparation Example-3 (Granules)

A mixture of 5 parts of the compound of the present invention, 35 parts of bentnite, 55 parts of talc and 5 parts of sodium ligninsulfonate was uniformly mixed and ground, thereafter water was added thereto, followed by kneading. The mixture was granulated by an extrusion granulator, dried, and sieved to obtain granules.

The herbicidal effects of the compound of the present invention were investigated according to the methods shown in the following Test Examples using the preparations prepared in accordance with the procedure illustrated as above. The herbicidal effects on the test weeds and the crop injury were determined according to the criterions shown below (Table-15).

TABLE 15

| Rating Criterions Percent Inhibition of Growth | |
| --- | --- |
| 1 | 0% |
| 2 | 25% |
| 3 | 50% |
| 4 | 75% |
| 5 | 100% |

As referential compounds, a commercially available compounds (MO:MO-338, Lonstar:G-315) were used for each screening test by using the same preparation procedure and treating method. The herbicidal activity against the test weeds and the crop injury by the referential agents were investigated on the same rating criterions as above, and the results obtained are also shown in Tables.

Test Example-1 (Effects on Paddy Field Weeds)

Soil of a paddy field was filled in a pot of $\frac{1}{10000}$ are, and seeds of *Echinochloa oryzicola, Cyperus difformis, Monochoria vaginalis, Scirpus juncoides, Eleocharis acicularis* and other annual broadleaf weeds, and rice seedlings at a 2.5-leaf stage (Species: Koshihikari) were seeded or transplanted, and the pot was maintained in the submerged condition. After one day, the wettable powder or the emulsion of the compound of the present invention prepared according to the preparation example was diluted, and the pot was treated dropwise at a predetermined dose per are. On the 15th day after the treatment, the herbicidal effect on the test weeds and the detrimental effect by the agent on the rice plant were investigated on the rating criterions in 1 to 5 ranks, and the results shown in Tables-16 and Table-17 were obtained.

TABLE 16

| Compd. No. | Amount Applied (gai/a) | Herbicidal Activity | | | | | | Injury Rice |
| --- | --- | --- | --- | --- | --- | --- | --- | --- |
| | | Eo | Cd | BL | Mv | Sj | Ea | |
| 97 | 0.5 | 5 | 5 | 5 | 5 | 5 | 5 | 2.5 |
| | 0.25 | 5 | 5 | 5 | 5 | 4 | 5 | 2.2 |
| | 0.1 | 3 | 5 | 5 | 5 | 3 | 5 | 2.0 |
| 99 | 2 | 3 | 2 | 2 | 2 | 2 | 2 | 1.5 |
| | 1 | 2 | 1.8 | 1.8 | 1.8 | 1.8 | 1.5 | 1.2 |
| | 0.5 | 5 | 5 | 5 | 5 | 5 | 5 | 2.0 |
| 101 | 0.25 | 4.7 | 5 | 5 | 5 | 5 | 5 | 1.8 |
| | 0.1 | 3 | 4 | 4 | 4 | 2.5 | 3 | 1.5 |
| | 0.5 | 5 | 5 | 5 | 5 | 5 | 5 | 2.2 |
| 102 | 0.25 | 5 | 5 | 5 | 5 | 5 | 5 | 2.0 |
| | 0.1 | 4.8 | 5 | 5 | 5 | 4 | 5 | 1.8 |
| | 0.5 | 5 | 5 | 5 | 5 | 5 | 5 | 2.0 |
| 103 | 0.25 | 5 | 5 | 5 | 5 | 5 | 5 | 1.8 |
| | 0.1 | 4.8 | 5 | 5 | 5 | 4 | 5 | 1.5 |
| 105 | 2 | 2 | 2.5 | 2.2 | 2.2 | 2.2 | 2.2 | 1.0 |
| | 1 | 1.8 | 2 | 1.8 | 1.8 | 1.8 | 1.5 | 1.0 |
| G-315 | 0.5 | 4.8 | 5 | 4.8 | 5 | 5 | 4.8 | 1.8 |
| | 0.25 | 3.8 | 5 | 3.5 | 5 | 3 | 3.5 | 1.5 |
| | 0.1 | 2 | 4 | 3 | 3 | 2 | 2 | 1.2 |

Eo: *Echinochloa oryzicola;* Cd: *Cyperus difformis;* BL: Annual broadleaf weeds; Mv: *Monochoria vaginalis;* Sj: *Scirpus juncoides;* Ea: *Eleocharis acicularis.*

TABLE 17

| Compd. No. | Amount Applied (gai/a) | Herbicidal Activity | | | | | | Injury Rice |
| --- | --- | --- | --- | --- | --- | --- | --- | --- |
| | | Eo | Cd | BL | Mv | Sj | Ea | |
| 460 | 0.5 | 1.5 | 1.2 | 1.2 | 1.2 | 1.2 | 1.2 | 1 |
| 462 | 0.5 | 1.5 | 1.8 | 1.8 | 1.8 | 1.2 | 1.5 | 1 |
| 476 | 0.5 | 4.8 | 5 | 5 | 5 | 4 | 5 | 2 |
| | 0.25 | 3.5 | 4 | 4 | 4 | 3 | 4 | 1.8 |
| 477 | 0.5 | 2 | 2.5 | 2.5 | 2.5 | 1.8 | 2 | 1.2 |
| | 0.25 | 1.8 | 2 | 2 | 2 | 1.5 | 1.8 | 1 |
| 478 | 0.5 | 5 | 5 | 5 | 5 | 5 | 5 | 2.4 |
| | 0.25 | 4.8 | 5 | 5 | 5 | 3 | 5 | 2.2 |
| 489 | 0.5 | 2.5 | 3 | 3 | 3 | 2 | 2.5 | 1.2 |
| | 0.25 | 1.8 | 2.2 | 2.5 | 2.2 | 1.5 | 2 | 1 |
| | 0.5 | 4.8 | 5 | 4.8 | 5 | 5 | 4.8 | 1.8 |
| 315 | 0.25 | 3.8 | 5 | 3.5 | 5 | 3 | 3.5 | 1.5 |
| MO-338 | 0.5 | 3.5 | 4.9 | 3.5 | — | 1.8 | 1.5 | 1.1 |
| | 0.25 | 1.5 | 3.5 | 1.2 | — | 1.5 | 1 | 1 |

Eo: *Echinochloa oryzicola;* Cd: *Cyperus difformis;* BL: Annual broadleaf weeds; Mv: *Monochoria vaginalis;* Sj: *Scirpus juncoides;* Ea: *Eleocharis acicularis.*

Test Example-2 (Effects by Field Soil Pretreatment)

A field soil was filled in a vat having an area of 10×10 cm$^2$ and a depth of 5 cm, and seeds of *Echinochloa crus-galli, Digitaria ciliaris, Amaranthus viridis, Chenopodium album* and corn were seeded, and a covering soil of 0.5 cm was put on the seeds. Next day, the wettable powder or the emulsion of the compound of the present invention prepared according to the preparation example was diluted and applied over the covering soil at a predetermined dose per are. On the 15th day after the treatment, the herbicidal effects on the test weeds and the detrimental effects by the agent on the corn were investigated on the rating criterions in 1 to 5 ranks, and the results obtained are shown in Table-18 and Table-19

TABLE 18

| Compd. No. | Amount Applied (gai/a) | Herbicidal Activity | | | | Injury Corn |
| --- | --- | --- | --- | --- | --- | --- |
| | | Ec | Dc | Av | Ca | |
| 97 | 10 | 4.8 | 5 | 5 | 5 | 2.0 |
| | 5 | 4.5 | 3 | 5 | 5 | 1.5 |
| 99 | 10 | 1.5 | 5 | 5 | 5 | 1.2 |
| 101 | 10 | 4.5 | 4.5 | 5 | 5 | 1.5 |
| | 5 | 4.2 | 4.5 | 4.5 | 5 | 1.2 |
| | 10 | 4.9 | 5 | 5 | 5 | 2.5 |
| 102 | 5 | 4.8 | 5 | 5 | 5 | 1.8 |
| | 2.5 | 4.8 | 4.9 | 5 | 5 | 1.5 |
| | 10 | 5 | 5 | 5 | 5 | 4.5 |
| 103 | 5 | 4.9 | 4.8 | 5 | 5 | 2.2 |
| | 2.5 | 4.6 | 4.6 | 5 | 5 | 1.5 |
| G- | 5 | 4.7 | 4.8 | 5 | 4.9 | 2.5 |
| 315 | 2.5 | 4 | 4.6 | 4.2 | 4.2 | 2.0 |

Ec:*Echinochloa crus-galli;*
Dc:*Digitaria ciliaris;*
Av:*Amaranthus viridis;*
Ca:*Chenopodium album.*

TABLE 19

| Compd. No. | Amount Applied (gai/a) | Herbicidal Activity | | | | Injury Corn |
| --- | --- | --- | --- | --- | --- | --- |
| | | Ec | Dc | Av | Ca | |
| 460 | 5 | 2.2 | 1.8 | 2.8 | 4 | 1.2 |
| | 2.5 | 1.7 | 1.2 | 2.2 | 2.5 | 1.1 |

TABLE 19-continued

| Compd. No. | Amount Applied (gai/a) | Herbicidal Activity | | | | Injury Corn |
|---|---|---|---|---|---|---|
| | | Ec | Dc | Av | Ca | |
| 462 | 5 | 1.8 | 1.8 | 4.2 | 4 | 1.8 |
| | 2.5 | 1.5 | 1.5 | 2 | 1.8 | 1.5 |
| 476 | 2.5 | 4.2 | 4.7 | 5 | 5 | 3 |
| | 1.25 | 2.8 | 3.2 | 5 | 5 | 2 |
| | 0.625 | 2.2 | 1.5 | 5 | 5 | 1.5 |
| 477 | 5 | 1.8 | 1.8 | 4.6 | 4.6 | 1.8 |
| | 2.5 | 1.5 | 1.5 | 3.5 | 3.3 | 1.5 |
| 478 | 2.5 | 4.3 | 4.5 | 5 | 5 | 3 |
| | 1.25 | 3.5 | 3 | 5 | 5 | 2 |
| | 0.625 | 2.5 | 1.8 | 5 | 5 | 1.5 |
| 479 | 5 | 1.8 | 1.8 | 4.8 | 4.8 | 1.8 |
| | 2.5 | 1.5 | 1.5 | 3 | 3 | 1.5 |
| G-315 | 5 | 4.7 | 4.8 | 5 | 4.9 | 2.5 |
| | 2.5 | 4 | 4.6 | 4.2 | 4.2 | 2 |
| MO-338 | 5 | 2.2 | 1.5 | 2 | 3 | 1.6 |
| | 2.5 | 1.5 | 1 | 1.5 | 1.2 | 1.2 |

Ec:*Echinochloa crus-galli*;
Dc:*Digitaria ciliaris*;
Av:*Amaranthus viridis*;
Ca:*Chenopodium album*.

Test Example-3 (Effects by Stem-Foliar Treatment)

A field soil was packed in a vat having an surface area of 10×10 cm2, and a depth of 5 cm, and seeds of *Echinochloa crus-galli, Digitaria ciliaris, Amaranthus viridis, Chenopodium album* and corn were seeded. After 15 days, the wettable powder or the emulsion of the compound of the present invention prepared according to the preparation example was diluted, adjusted to a predetermined concentration, and the stem-foliar portion of the plant was spray treated at a liquid amount of 20 liters per are. On the 10th day after the treatment, the herbicidal effects on the tested weeds and the detrimental effects by the agent on the corn were investigated on the rating criterions in 1 to 5 ranks, and the results obtained are shown in Table-20 and Table-21.

TABLE 20

| Compd. No. | Amount Applied (gai/a) | Herbicidal Activity | | | | Injury Corn |
|---|---|---|---|---|---|---|
| | | Ec | Dc | Av | Ca | |
| 97 | 500 | 4 | 5 | 5 | 5 | 4.5 |
| | 100 | 3 | 5 | 5 | 4.5 | 3.0 |
| 99 | 500 | 5 | 5 | 5 | 5 | 4.7 |
| | 100 | 4.5 | 5 | 5 | 5 | 4.5 |
| | 25 | 4 | 5 | 5 | 4.5 | 4.0 |
| 101 | 500 | 5 | 5 | 5 | 5 | 5.0 |
| | 100 | 4 | 5 | 5 | 5 | 4.0 |
| 102 | 500 | 5 | 5 | 5 | 5 | 5.0 |
| | 100 | 4.9 | 5 | 5 | 5 | 4.0 |
| | 25 | 4 | 5 | 5 | 5 | 3.8 |
| 103 | 500 | 5 | 5 | 5 | 5 | 5.0 |
| | 100 | 4.9 | 5 | 5 | 5 | 4.5 |
| | 25 | 4.2 | 5 | 5 | 5 | 4.2 |
| 105 | 500 | 1.8 | 5 | 2.5 | 3.5 | 1.8 |
| | 100 | 1.5 | 4 | 1.5 | 2.5 | 1.5 |
| G-315 | 100 | 4.8 | 5 | 5 | 5 | 3.8 |
| | 25 | 2.5 | 4.2 | 3.8 | 4.8 | 2.5 |

Ec:*Echinochloa crus-galli*;
Dc:*Digitaria ciliaris*;
Av:*Amaranthus viridis*;
Ca:Chenopodium album.

TABLE 21

| Compd. No. | Amount Applied (gai/a) | Herbicidal Activity | | | | Injury Corn |
|---|---|---|---|---|---|---|
| | | Ec | Dc | Av | Ca | |
| 460 | 100 | 3.5 | 5 | 3.5 | 5 | 3.2 |
| | 25 | 2 | 5 | 2.5 | 4.5 | 2.0 |
| 461 | 100 | 1.5 | 1.8 | 1.8 | 1.8 | 1 |
| | 25 | 1.2 | 1.5 | 1.5 | 1.5 | 1 |
| 476 | 100 | 4.5 | 5 | 5 | 5 | 4.5 |
| | 25 | 3 | 5 | 4 | 5 | 4 |
| 477 | 100 | 2 | 5 | 4 | 4.9 | 2.5 |
| | 25 | 1.8 | 5 | 2.2 | 3.5 | 1.5 |
| 478 | 100 | 5 | 5 | 5 | 5 | 4.8 |
| | 25 | 3.8 | 5 | 4.5 | 5 | 3.5 |
| | 12.5 | 3.5 | 5 | 3.5 | 5 | 3 |
| 479 | 100 | 2 | 5 | 2.5 | 4.6 | 2.5 |
| | 25 | 1.6 | 5 | 2 | 3 | 1.5 |
| G-315 | 100 | 4.8 | 5 | 5 | 5 | 3.8 |
| | 25 | 2.5 | 4.2 | 3.8 | 4.8 | 2.5 |
| MO-338 | 25 | 1.6 | 3 | 2.3 | 2.8 | 1.8 |

Ec:*Echinochloa crus-galli*;
Dc:*Digitaria ciliaris*;
Av:*Amaranthus viridis*;
Ca:Chenopodium album.

Industrial Applicability

The bicyclic hydantoin derivatives of the present invention exhibit an excellent herbicidal activity against many kinds of weeds and are further useful as active ingredients of herbicides. These compounds are readily produced according to the processes of the present invention. The herbicides of the present invention containing these compounds as active ingredients are able to be used as agricultural herbicides in paddy filed and upland field.

We claim:

1. A hydantoin derivative represented by the formula (1):

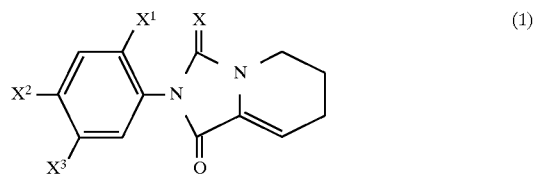

wherein X represents an oxygen atom or a sulfur atom, $X^1$ represents a hydrogen atom, a halogen atom or a C1–8 alkyl group, $X^2$ represents a hydrogen atom, a halogen atom, a C1–8 alkyl group or a group represented by the formula: —Y—CH($R^1$)C(=O)$OR^2$, $X^3$ represents a hydrogen atom, a halogen atom, a C1–8 alkyl group, $ZR^3$, a nitro group or $NR^4R^5$, or $X^2$ and $X^3$ may be combined together to form a group represented by the formula: —Y—CH($R^1$)C(=O)$NR^6$—, wherein Y and Z represent an oxygen atom or a sulfur atom, $R^1$ represents a hydrogen atom or a C1–4 alkyl group, $R^2$ represents a C1–6 alkyl group or an aralkyl group, $R^3$ represents a hydrogen atom, a C1–11 alkyl group, a C3–8 cycloalkyl group, a C3–12 alkenyl group, a C3–12 alkynyl group, a C1–8 alkoxycarbonylmethyl group, a C1–8 alkoxycarbonyl group or a C7–11 aralkyloxycarbonyl group, $R^4$ and $R^5$ independently represent a hydrogen atom, a C1–6 alkyl group, a C2–6 acyl group, a C1–6 alkylsulfonyl group or an arylsulfonyl group, $R^6$ represents a hydrogen atom, a C1–11 alkyl group, a C3–8 cycloalkyl group, a C3–12 alkenyl group or a C3–12 alkynyl group.

2. A herbicide comprising, together with an inert carrier, an herbicidally effective amount of hydantoin derivative represented by the formula (1):

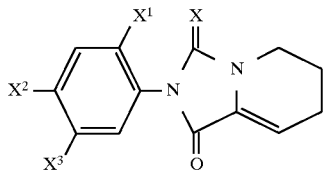

wherein X represents an oxygen atom or a sulfur atom, $X^1$ represents a hydrogen atom, a halogen atom or a C1–8 alkyl group, $X^2$ represents a hydrogen atom, a halogen atom, a C1–8 alkyl group or a group represented by the formula: —Y—CH($R^1$)C(=O)O$R^2$, $X^3$ represents a hydrogen atom, a halogen atom, a C1–8 alkyl group, Z$R^3$, a nitro group or N$R^4R^5$, or $X^2$ and $X^3$ may be combined together to form a group represented by the formula: —Y—CH($R^1$)C(=O)N$R^6$—, wherein Y and Z represent an oxygen atom or a sulfur atom, $R^1$ represents a hydrogen atom or a C1–4 alkyl group, $R^2$ represents a C1–6 alkyl group or an aralkyl group, $R^3$ represents a hydrogen atom, a C1–11 alkyl group, a C3–8 cycloalkyl group, a C3–12 alkenyl group, a C3–12 alkynyl group, a C1–8 alkoxycarbonylmethyl group, a C1–8 alkoxycarbonyl group or a C7–11 aralkyloxycarbonyl group, $R^4$ and $R^5$ independently represent a hydrogen atom, a C1–6 alkyl group, a C2–6 acyl group, a C1–6 alkylsulfonyl group or an arylsulfonyl group, $R^6$ represents a hydrogen atom, a C1–11 alkyl group, a C3–8 cycloalkyl group, a C3–12 alkenyl group or a C3–12 alkynyl group.

* * * * *

UNITED STATES PATENT AND TRADEMARK OFFICE

CERTIFICATE OF CORRECTION

PATENT NO.   : 5,883,049
DATED        : March 16, 1999
INVENTOR(S)  : HIRAI et al It is certified that error appears in the above-identified patent and that said letters patent is hereby corrected as shown below:

Title page, column 1, section [30], change "6-3245536" to read --6-324536--.

Signed and Sealed this

Twenty-seventh Day of July, 1999

*Attest:*

Q. TODD DICKINSON

*Attesting Officer*    *Acting Commissioner of Patents and Trademarks*